(12) United States Patent
Jung et al.

(10) Patent No.: US 9,548,460 B2
(45) Date of Patent: Jan. 17, 2017

(54) COMPOUND FOR ORGANIC OPTOELECTRONIC DEVICE, ORGANIC LIGHT EMITTING DIODE INCLUDING THE SAME AND DISPLAY INCLUDING THE ORGANIC LIGHT EMITTING DIODE

(71) Applicants: Ho-Kuk Jung, Uiwang-si (KR);
Dong-Min Kang, Uiwang-si (KR);
Myeong-Soon Kang, Uiwang-si (KR);
Eui-Su Kang, Uiwang-si (KR);
Nam-Soo Kim, Uiwang-si (KR);
Nam-Heon Lee, Uiwang-si (KR);
Mi-Young Chae, Uiwang-si (KR)

(72) Inventors: Ho-Kuk Jung, Uiwang-si (KR);
Dong-Min Kang, Uiwang-si (KR);
Myeong-Soon Kang, Uiwang-si (KR);
Eui-Su Kang, Uiwang-si (KR);
Nam-Soo Kim, Uiwang-si (KR);
Nam-Heon Lee, Uiwang-si (KR);
Mi-Young Chae, Uiwang-si (KR)

(73) Assignee: CHEIL INDUSTRIES, INC., Gumi-Si, Kyeongsangbuk-Do (KR)

( * ) Notice: Subject to any disclaimer, the term of this patent is extended or adjusted under 35 U.S.C. 154(b) by 531 days.

(21) Appl. No.: 13/835,341

(22) Filed: Mar. 15, 2013

(65) Prior Publication Data
US 2013/0200356 A1    Aug. 8, 2013

Related U.S. Application Data

(63) Continuation of application No. PCT/KR2011/005385, filed on Jul. 21, 2011.

(30) Foreign Application Priority Data

Dec. 31, 2010    (KR) .......................... 10-2010-0140564

(51) Int. Cl.
*H01L 51/54*    (2006.01)
*C09K 11/06*    (2006.01)
(Continued)

(52) U.S. Cl.
CPC ......... *H01L 51/0072* (2013.01); *C07D 401/10* (2013.01); *C07D 401/14* (2013.01); *C07D 403/10* (2013.01); *C07D 403/14* (2013.01); *C07D 413/14* (2013.01); *C09B 57/00* (2013.01); *C09K 11/06* (2013.01); *H01L 51/0058* (2013.01);
(Continued)

(58) Field of Classification Search
CPC ..... Y02E 10/549; C09B 57/00; C07D 235/00; C07D 235/02; C07D 235/04; C07D 235/06; C07D 235/08; C07D 235/18; C07D 235/20; C07D 401/00; C07D 401/02; C07D 401/04; C07D 401/10; C07D 401/14; C07D 403/00; C07D 403/02; C07D 403/04; C07D 403/10; C07D 403/14; C07D 413/00; C07D 413/02; C07D 413/04; C07D 413/10; C07D 413/14; C09K 11/06; C09K 2211/00; C09K 2211/1007; C09K 2211/1018; C09K 2211/1011; C09K 2211/10; C09K 2211/1029; C09K 2211/1044; C09K 2211/1059; H01L 51/0032; H01L 51/005; H01L 51/0051; H01L 51/0052; H01L 51/0054; H01L 51/0055; H01L 51/0056; H01L 51/0058; H01L 51/0062; H01L 51/0067; H01L 51/0071; H01L 51/0072; H01L 51/50; H01L 51/5012; H01L 51/5016; H01L 51/5052; H01L 51/5056; H01L 51/5072; H01L 51/5076; H05B 33/10
(Continued)

(56) References Cited

U.S. PATENT DOCUMENTS

2004/0146745 A1\* 7/2004 Ise et al. .................. 428/690
2006/0147747 A1\* 7/2006 Yamamoto et al. ........ 428/690
(Continued)

FOREIGN PATENT DOCUMENTS

JP    10-106749    4/1998
JP    2001-247858    9/2001
(Continued)

OTHER PUBLICATIONS

Y. Karzazi; "Organic Light Emitting Diodes: Devices and applications", J. Mater. Environ. Sci. 5 (1) (2014) 1-12.
(Continued)

*Primary Examiner* — Andrew K Bohaty
(74) *Attorney, Agent, or Firm* — Lee & Morse, P.C.

(57) ABSTRACT

A compound for an organic optoelectronic device is represented by Chemical Formula 1:

[Chemical Formula 1]

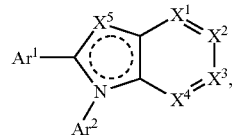

and, in Chemical Formula 1, one of $Ar^1$ or $Ar^2$ is a substituted or unsubstituted C6 to C30 aryl group, or a substituted or unsubstituted C3 to C30 heteroaryl
(Continued)

group, and the other of $Ar^1$ or $Ar^2$ is a substituent represented by the Chemical Formula 2:

[Chemical Formula 2]

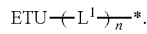

$ETU{-}(L^1)_n{-}*$.

11 Claims, 11 Drawing Sheets

(51) Int. Cl.
| H01L 51/00 | (2006.01) |
| C09B 57/00 | (2006.01) |
| H05B 33/10 | (2006.01) |
| C07D 401/14 | (2006.01) |
| C07D 413/14 | (2006.01) |
| C07D 401/10 | (2006.01) |
| C07D 403/10 | (2006.01) |
| C07D 403/14 | (2006.01) |
| H01L 51/50 | (2006.01) |

(52) U.S. Cl.
 CPC ........... *H01L 51/0067* (2013.01); *H05B 33/10* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *H01L 51/5056* (2013.01); *H01L 51/5072* (2013.01); *Y02E 10/549* (2013.01)

(58) Field of Classification Search
 USPC ....... 428/690, 691, 917, 411.4, 336; 427/58, 427/66; 313/500–512; 257/40, 88–104, 257/E51.001–E51.052; 252/301.16–301.35; 544/333
 See application file for complete search history.

(56) References Cited

U.S. PATENT DOCUMENTS

| 2007/0104977 A1 | 5/2007 | Arakane et al. |
| 2010/0066243 A1 | 3/2010 | Igarashi et al. |

FOREIGN PATENT DOCUMENTS

| JP | 2009-155300 | 7/2009 |
| KR | 10-2008-0105112 A | 12/2008 |
| KR | 10-2009-0073852 A | 7/2009 |
| KR | 10-2010-0077675 A | 7/2010 |
| KR | 10-2010-0082049 A | 7/2010 |
| WO | WO 2009051454 A2 * | 4/2009 |
| WO | WO 2010074422 A1 * | 7/2010 |
| WO | WO 2010126270 A1 * | 11/2010 |

OTHER PUBLICATIONS

Hiroko Inomata, et al., "High-Efficiency Organic Electrophosphorescent Diodes Using 1,3,5-Triazine Electron Transport Materials", Chem. Mater. 2004, 16, 1285-1291.

Hany Aziz, et al., "Degradation Phenomena in Small-Molecule Organic Light-Emitting Devices", Chem. Mater. 2004, 16, 4522-4532.

Soo Young Kim, "Dark spot formation mechanism in organic light emitting diodes", Applied Physics Letters 89, 132108 (2006).

\* cited by examiner

COMPOUND FOR ORGANIC OPTOELECTRONIC DEVICE, ORGANIC LIGHT EMITTING DIODE INCLUDING THE SAME AND DISPLAY INCLUDING THE ORGANIC LIGHT EMITTING DIODE

CROSS-REFERENCE TO RELATED APPLICATIONS

This application is a continuation under 35 U.S.C. §120 of pending International Application No. PCT/KR2011/005385, entitled "Compound for Organic Optoelectronic Device, Organic Light Emitting Diode Including the Same and Display Including the Organic Light Emitting Diode," which was filed on Jul. 21, 2011, the entire contents of which are hereby incorporated by reference.

The present application claims priority under 35 U.S.C. §119 to Korean Patent Application No. 10-2010-0140564, filed on Dec. 31, 2010, in the Korean Intellectual Property Office, and entitled: "Compound for Organic Optoelectronic Device, Organic Light Emitting Diode Including the Same and Display Including the Organic Light Emitting Diode," the entire contents of which are hereby incorporated by reference.

BACKGROUND

1. Field

Embodiments are directed to a compound for an organic optoelectronic device, an organic light emitting diode including the compound, and a display device including the organic light emitting diode.

2. Description of the Related Art

An organic optoelectronic device is, in a broad sense, a device for transforming photo-energy to electrical energy or conversely, a device for transforming electrical energy to photo-energy.

An organic optoelectronic device may be classified as follows in accordance with its driving principles. A first organic optoelectronic device is an electronic device driven as follows: excitons are generated in an organic material layer by photons from an external light source; the excitons are separated into electrons and holes, and the electrons and holes are transferred to different electrodes as a current source (voltage source). A second organic optoelectronic device is an electronic device driven as follows: a voltage or a current is applied to at least two electrodes to inject holes and/or electrons into an organic material semiconductor positioned at an interface of the electrodes, and the device is driven by the injected electrons and holes.

SUMMARY

Embodiments are directed to a compound for an organic optoelectronic device represented by Chemical Formula 1:

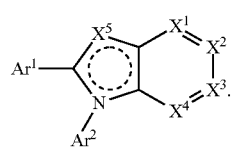

[Chemical Formula 1]

In Chemical Formula 1, $X^1$ to $X^4$ are each independently —N—, —$CR^1$—, —$CR^2$—, —$CR^3$—, or —$CR^4$—, $X^5$ is —O—, —S—, —Se—, or —N—, $R^1$ to $R^4$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof. One of $Ar^1$ or $Ar^2$ is a substituted or unsubstituted C6 to C30 aryl group, or a substituted or unsubstituted C3 to C30 heteroaryl group, and another of $Ar^1$ or $Ar^2$ is a substituent represented by Chemical Formula 2:

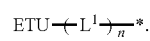

[Chemical Formula 2]

In Chemical Formula 2, * is a bonding site of the substituent represented by Chemical Formula 2 in Chemical Formula 1, $L^1$ is a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n is an integer from 0 to 2, and ETU is a substituted or unsubstituted C3 to C30 heteroaryl group having electronic properties.

The substituent represented by Chemical Formula 2 may be a substituent represented by Chemical Formula 3:

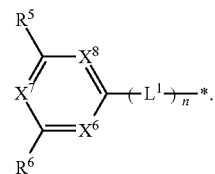

[Chemical Formula 3]

In Chemical Formula 3, * is a bonding site of the substituent represented by Chemical Formula 3 in Chemical Formula 1, $X^6$ to $X^8$ are each independently —N— or —CR'—, R' is hydrogen or deuterium, at least one of $X^6$ to $X^8$ is —N—, $L^1$ is a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n is an integer from 0 to 2, and $R^5$ and $R^6$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof.

In Chemical Formula 3, $R^5$ and $R^6$ each independently may be a substituted or unsubstituted naphthyl group, a substituted or unsubstituted anthracenyl group, a substituted or unsubstituted phenanthrenyl group, a substituted or unsubstituted triphenylenyl group, a substituted or unsubstituted pyrenyl group, a substituted or unsubstituted chrysenyl group, or a combination thereof.

The compound may be represented by Chemical Formula 4:

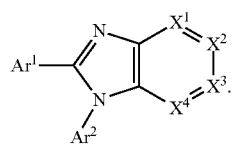

[Chemical Formula 4]

In Chemical Formula 4, $X^1$ to $X^4$ are each independently —N—, —$CR^1$—, —$CR^2$—, —$CR^3$—, or —$CR^4$—, $R^1$ to $R^4$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof. One of $Ar^1$ or $Ar^2$ is a substituted or unsubstituted C6 to C30 aryl group, or a substituted or unsubstituted C3 to C30 heteroaryl group, and another of $Ar^1$ or $Ar^2$ is a substituent represented by Chemical Formula 2:

[Chemical Formula 2]

ETU—$(L^1)_n$—*.

In Chemical Formula 2, * is a bonding site of the substituent represented by Chemical Formula 2 in Chemical Formula 4, $L^1$ is a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n is an integer from 0 to 2, and ETU is a substituted or unsubstituted C3 to C30 heteroaryl group having electronic properties.

The compound may be represented by Chemical Formula 5:

[Chemical Formula 5]

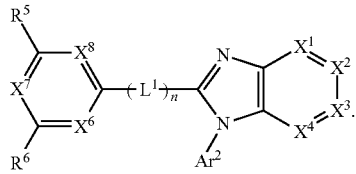

In Chemical Formula 5, $X^1$ to $X^4$ each independently may be —N—, —$CR^1$—, —$CR^2$—, —$CR^3$—, or —$CR^4$—, $R^1$ to $R^4$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, $Ar^2$ is a substituted or unsubstituted C6 to C30 aryl group, or a substituted or unsubstituted C3 to C30 heteroaryl group, $L^1$ is a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n is an integer from 0 to 2, $X^6$ to $X^8$ are each independently —N—, or —$CR^1$—, R' is hydrogen or deuterium, at least one of $X^6$ to $X^8$ is —N—, and $R^5$ and $R^6$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof.

The compound may be represented by Chemical Formula 6:

[Chemical Formula 6]

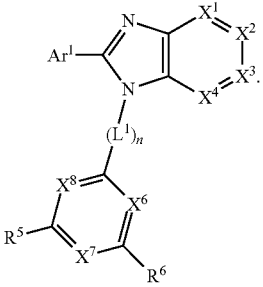

In Chemical Formula 6, $X^1$ to $X^4$ are each independently —N—, —$CR^1$—, —$CR^2$—, —$CR^3$—, or —$CR^4$—, $R^1$ to $R^4$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, $Ar^1$ is a substituted or unsubstituted C6 to C30 aryl group, or a substituted or unsubstituted C3 to C30 heteroaryl group, $L^1$ is a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n is an integer from 0 to 2, $X^6$ to $X^8$ are each independently —N— or —$CR^1$—, R' is hydrogen or deuterium, at least one of $X^6$ to $X^8$ is —N—, and $R^5$ and $R^6$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof.

In Chemical Formula 2, the substituted or unsubstituted C3 to C30 heteroaryl group having the electronic properties may be a substituted or unsubstituted imidazolyl group, a substituted or unsubstituted triazolyl group, a substituted or unsubstituted tetrazolyl group, a substituted or unsubstituted carbazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof.

In Chemical Formula 2, n may be an integer from 1 to 2, and $L^1$ may be a substituted or unsubstituted ethenylene, a substituted or unsubstituted ethynylene, a substituted or unsubstituted phenylene, a substituted or unsubstituted biphenylene, a substituted or unsubstituted naphthalene, a substituted or unsubstituted pyridinylene, a substituted or unsubstituted pyrimidinylene, or a substituted or unsubstituted triazinylene.

The compound may be represented by one of Chemical Formulae A1 to A45 and A64 to A72:
[Chemical Formula A1]
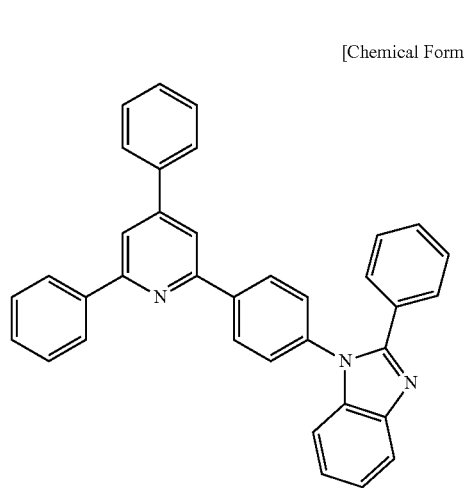
[Chemical Formula A2]
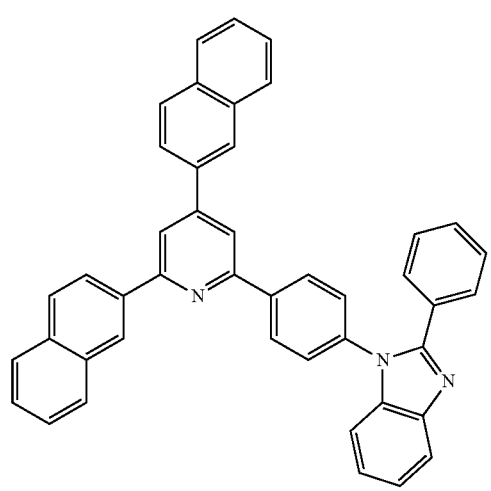
[Chemical Formula A3]
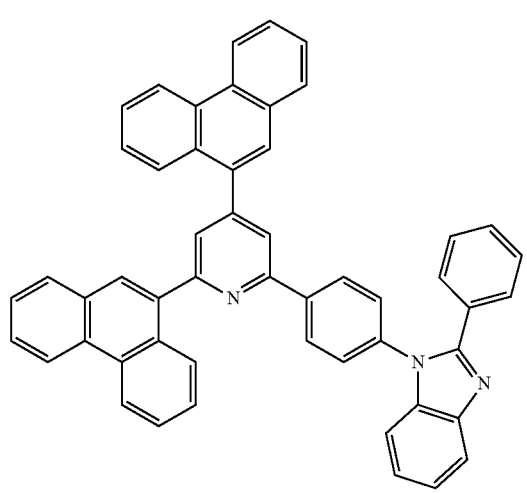
[Chemical Formula A4]
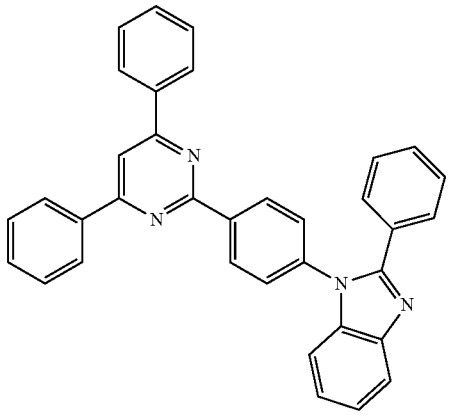
[Chemical Formula A5]
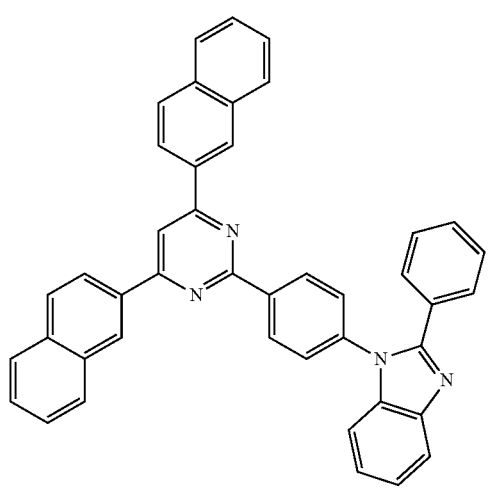
[Chemical Formula A6]
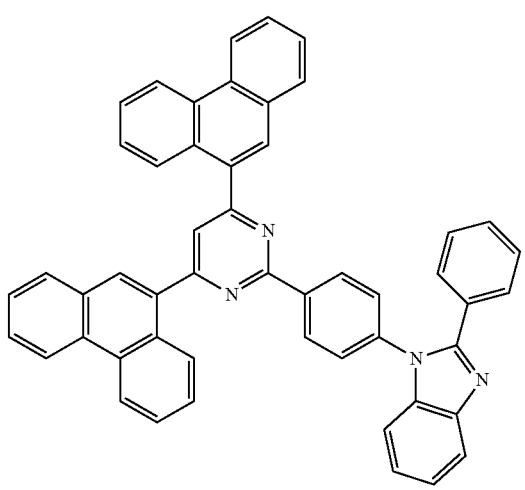

[Chemical Formula A7]
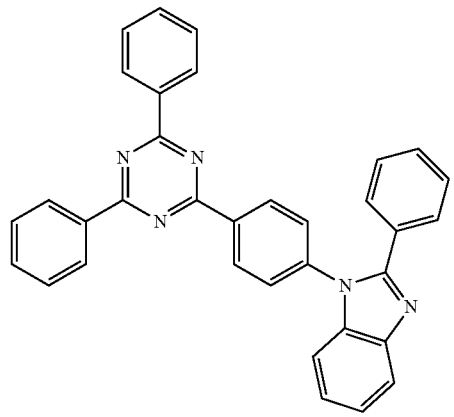
[Chemical Formula A8]
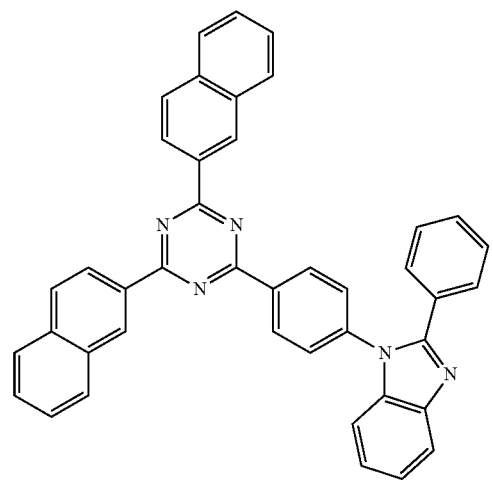
[Chemical Formula A9]
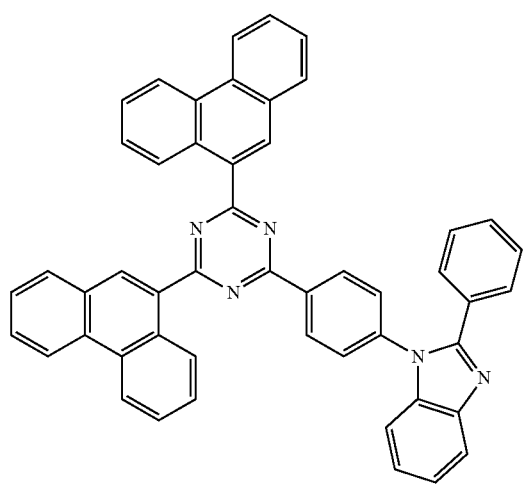
[Chemical Formula A10]
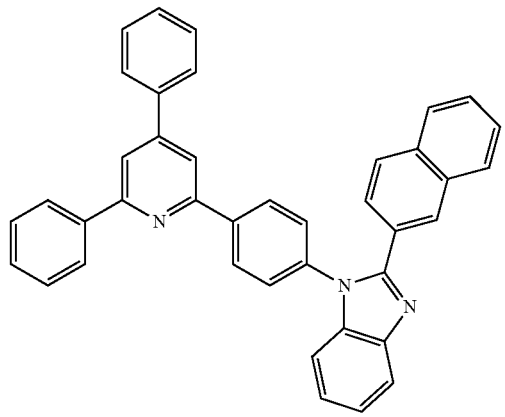
[Chemical Formula A11]
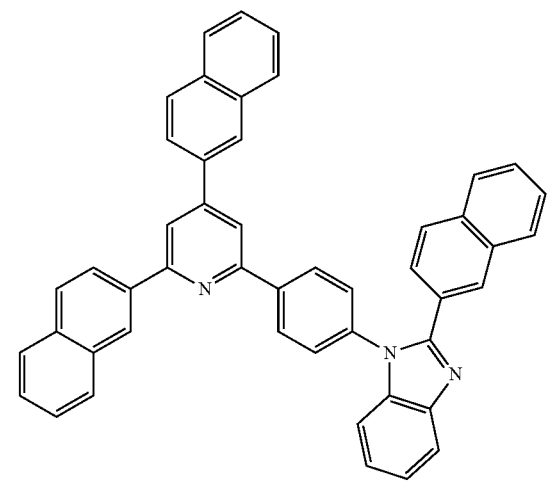
[Chemical Formula A12]
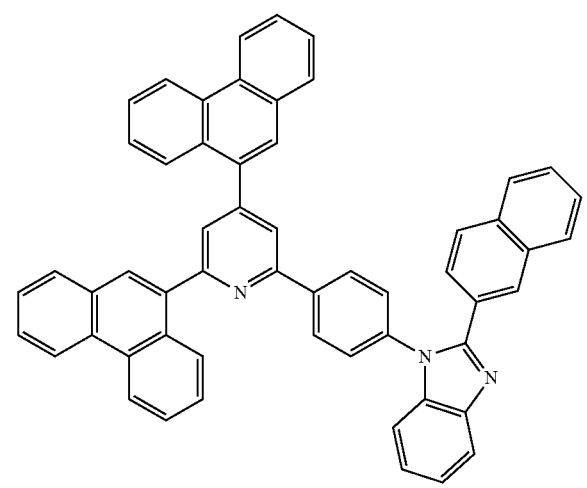

-continued
[Chemical Formula A13]
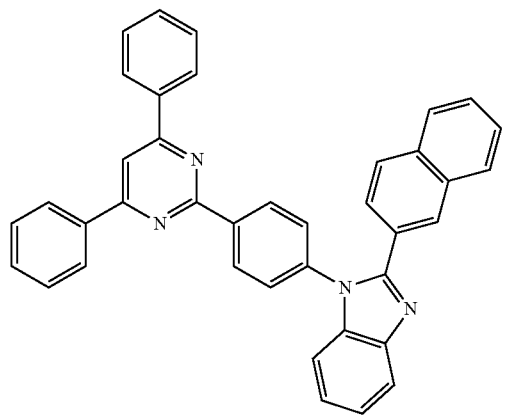
[Chemical Formula A14]
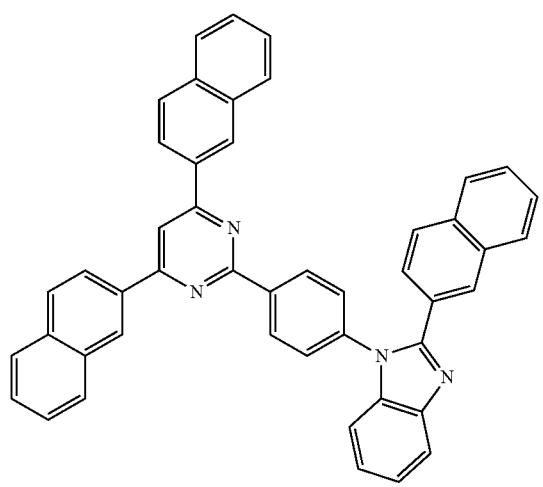
[Chemical Formula A15]
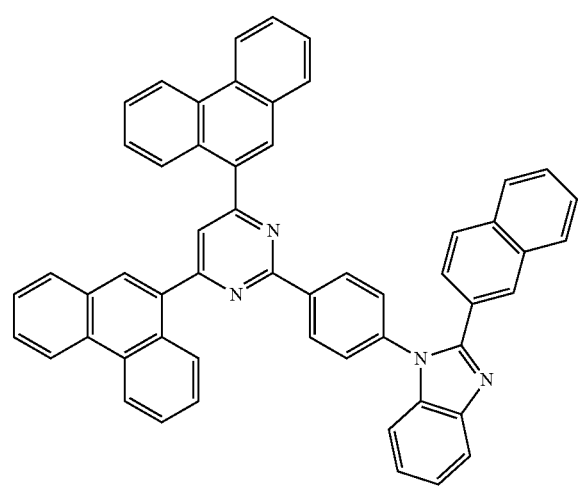
-continued
[Chemical Formula A16]
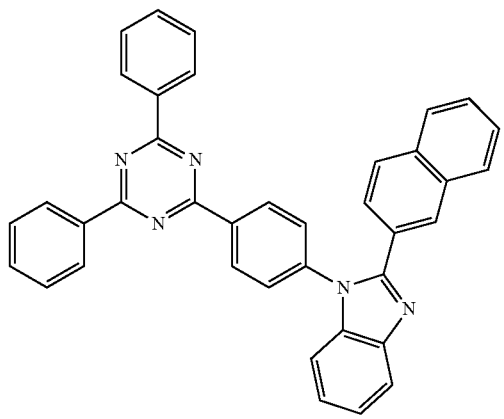
[Chemical Formula A17]
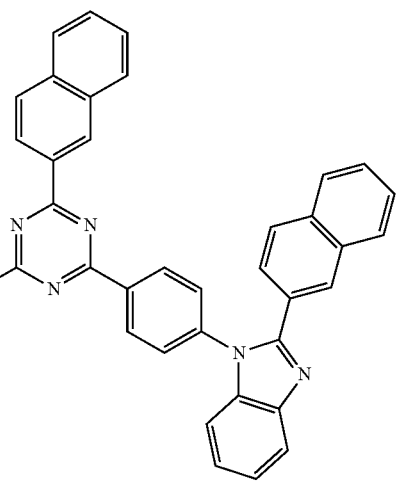
[Chemical Formula A18]
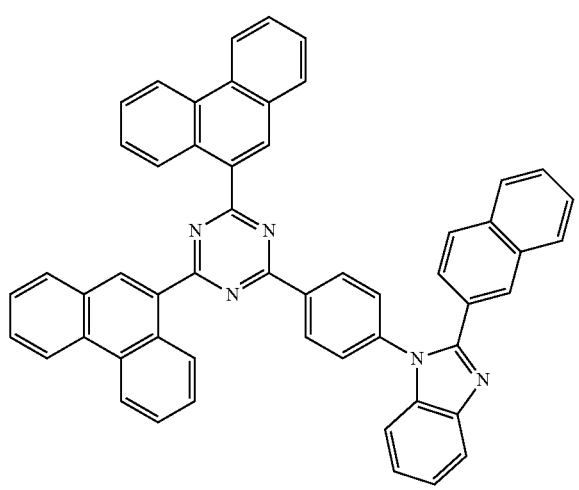

[Chemical Formula A19]
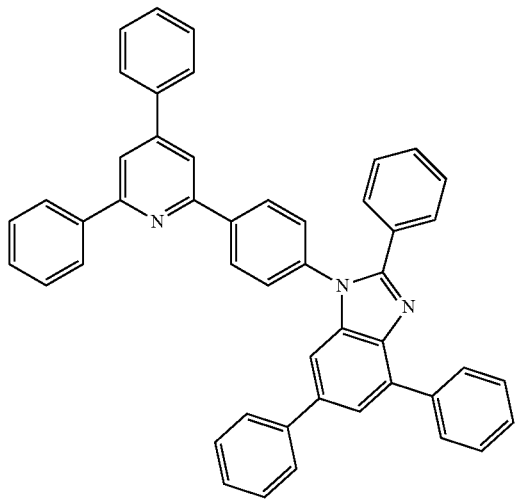
[Chemical Formula A20]
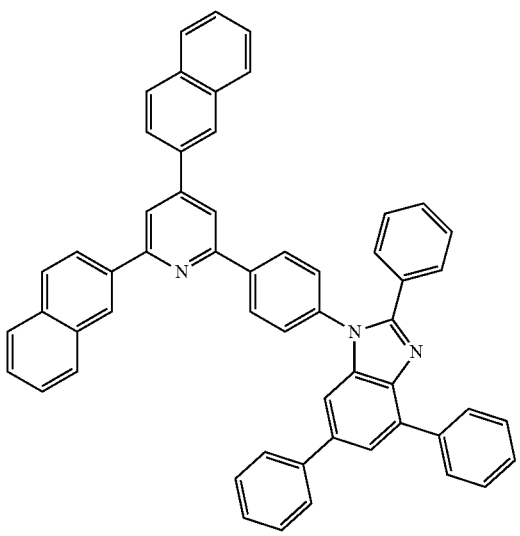
[Chemical Formula A21]
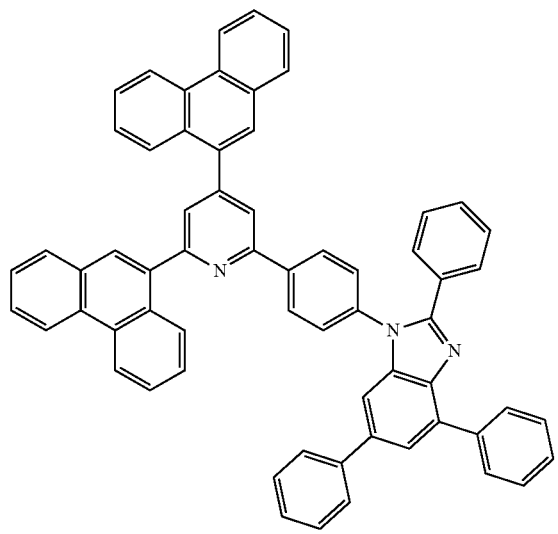
[Chemical Formula A22]
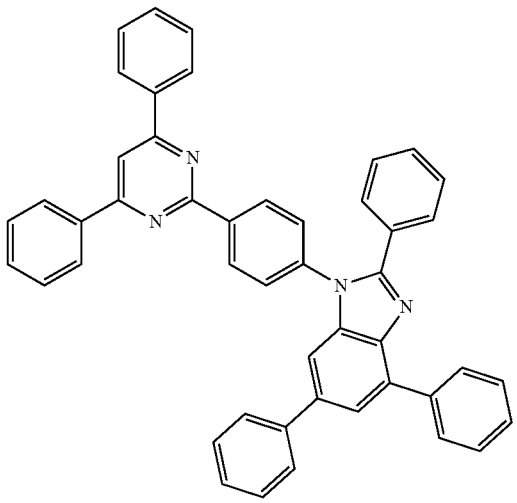
[Chemical Formula A23]
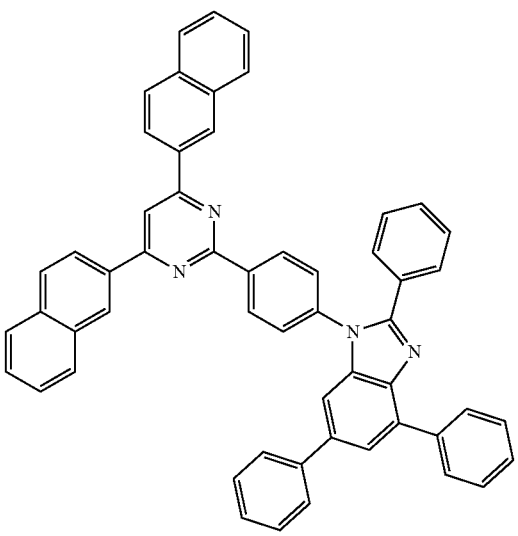
[Chemical Formula A24]
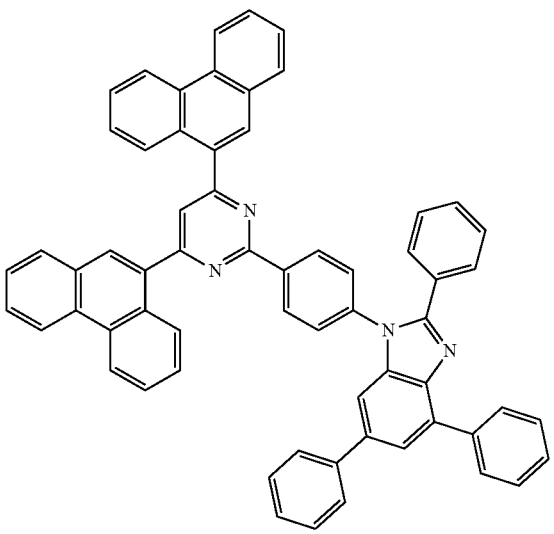

[Chemical Formula A25]
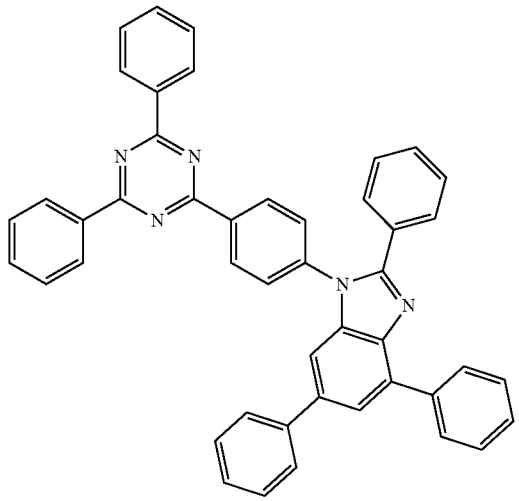
[Chemical Formula A26]
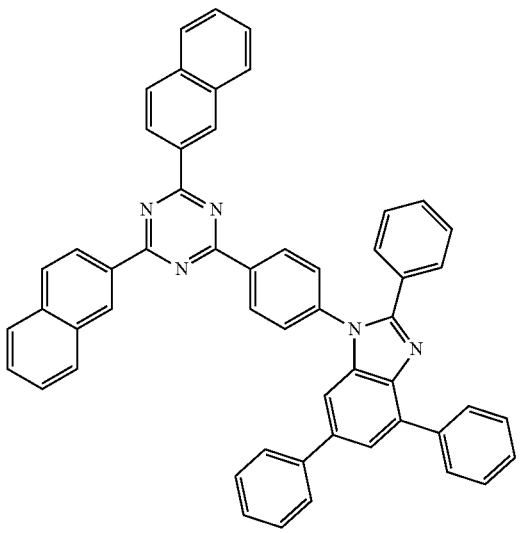
[Chemical Formula A27]
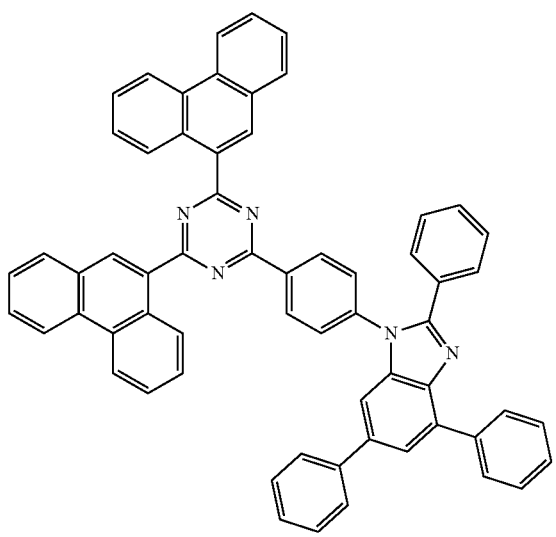
[Chemical Formula A28]
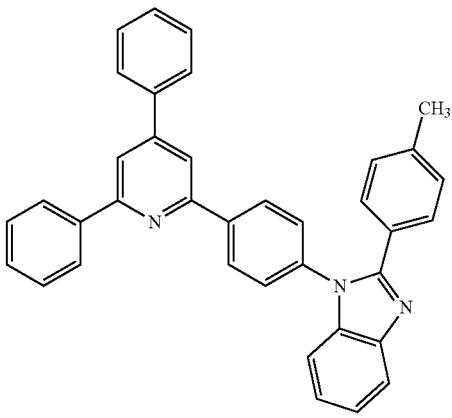
[Chemical Formula A29]
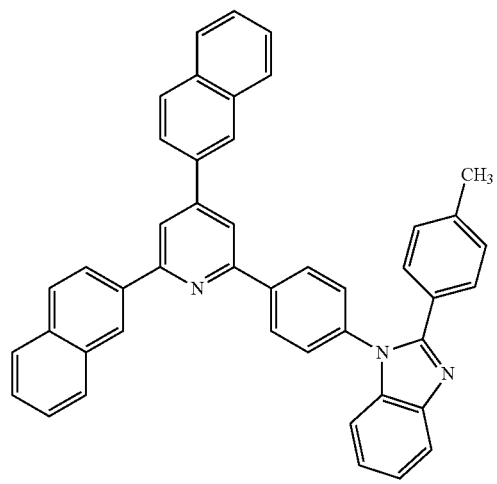
[Chemical Formula A30]
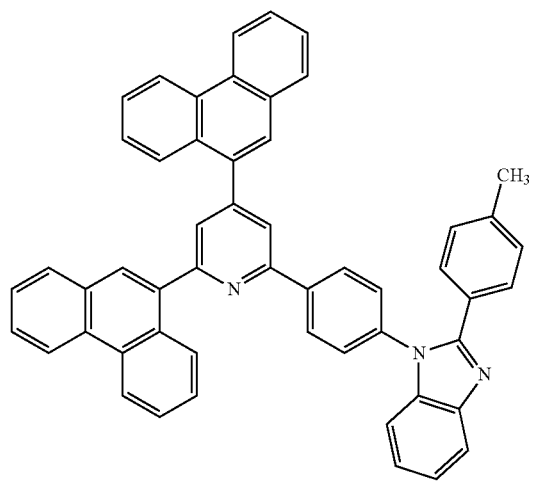

[Chemical Formula A31]
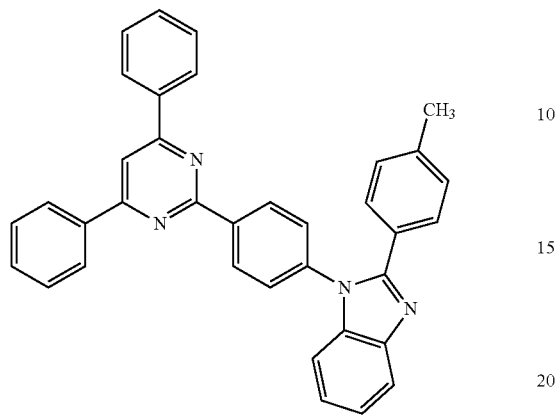
[Chemical Formula A32]
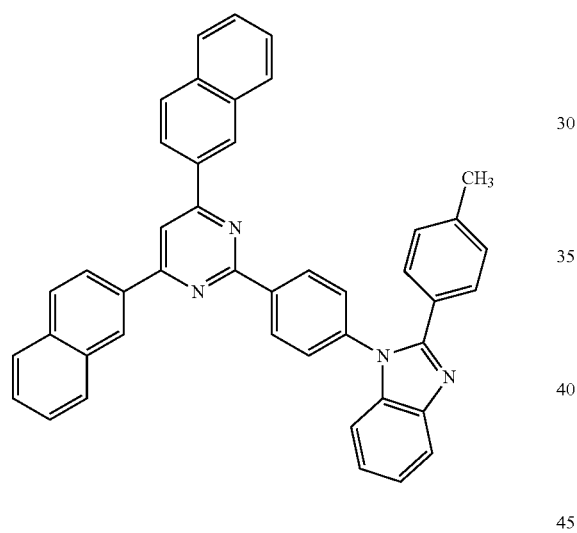
[Chemical Formula A33]
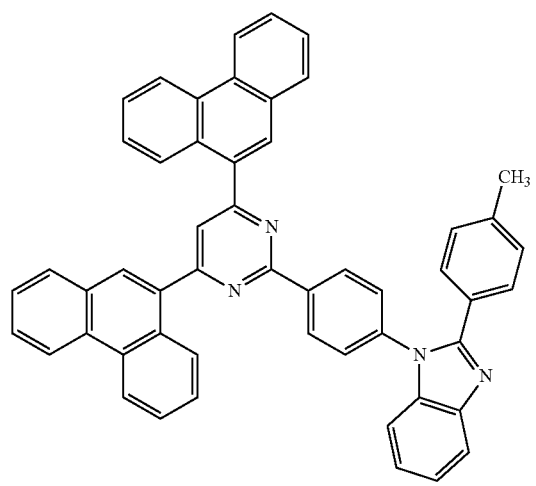
[Chemical Formula A34]
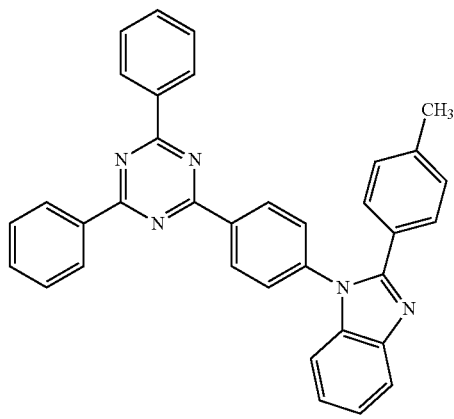
[Chemical Formula A35]
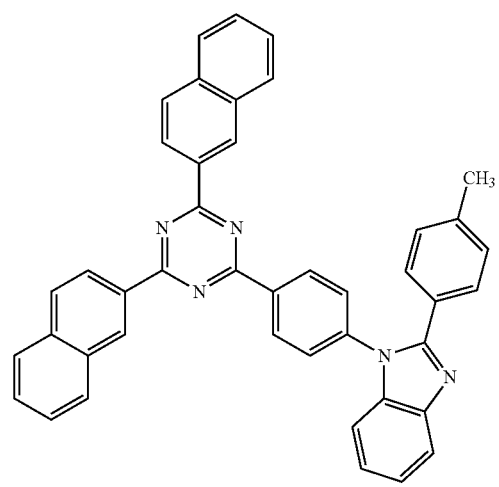
[Chemical Formula A36]
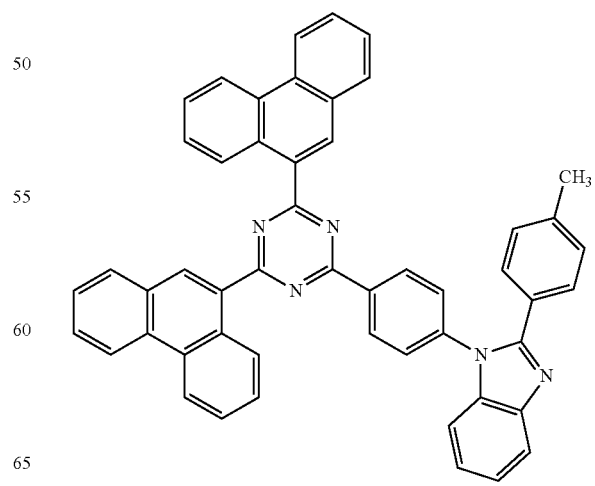

[Chemical Formula A37]
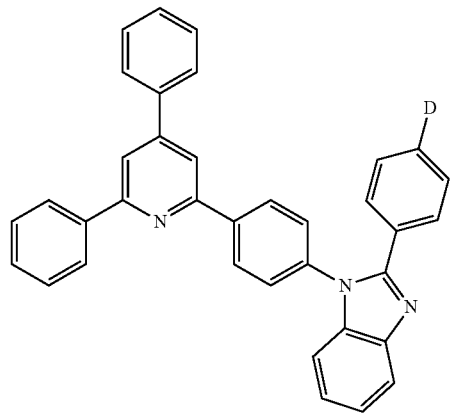
[Chemical Formula A38]
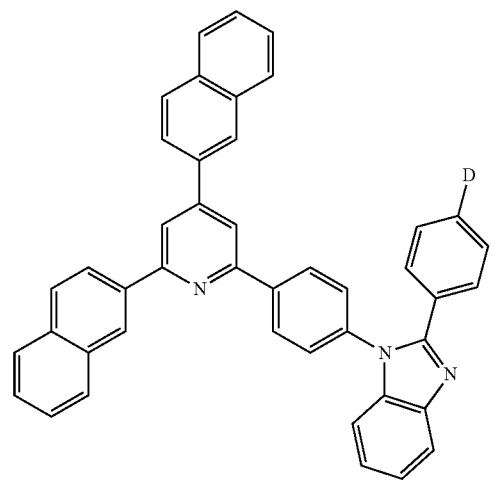
[Chemical Formula A39]
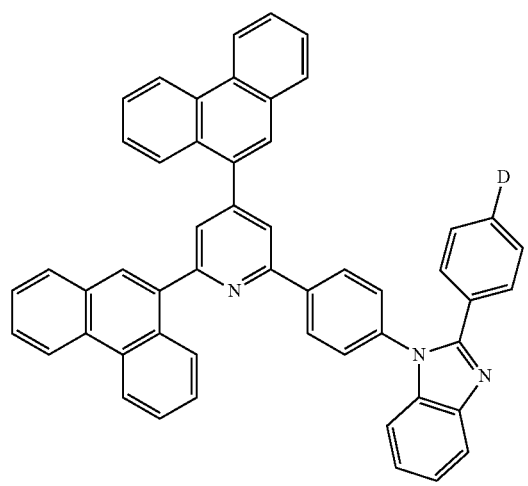
[Chemical Formula A40]
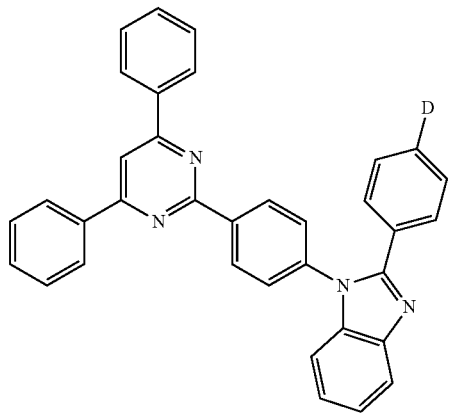
[Chemical Formula A41]
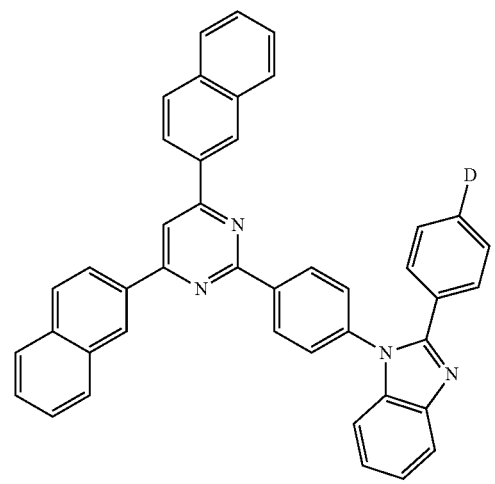
[Chemical Formula A42]
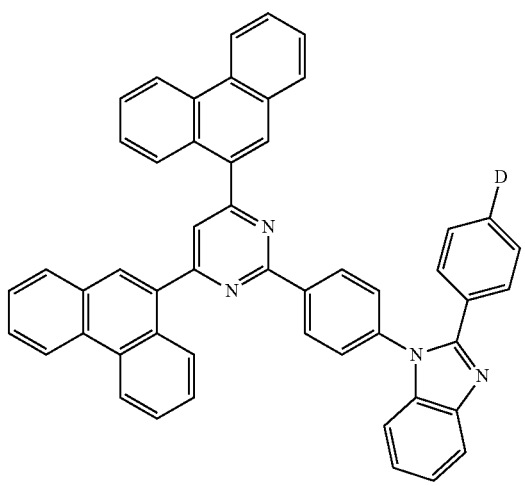

[Chemical Formula A43]
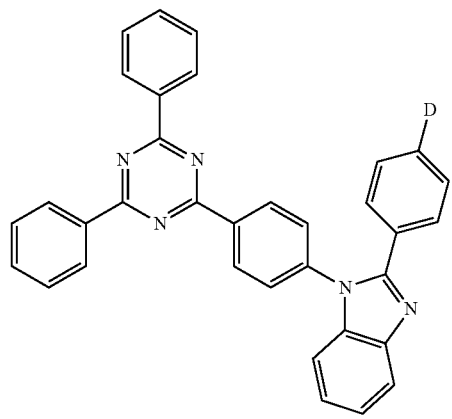
[Chemical Formula A64]
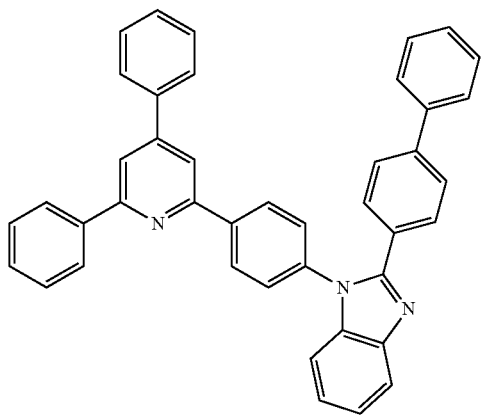
[Chemical Formula A44]
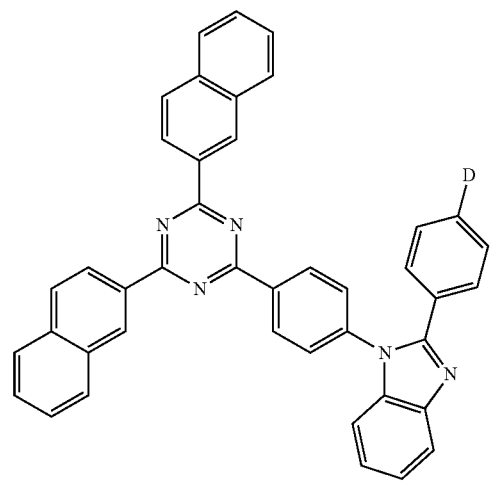
[Chemical Formula A65]
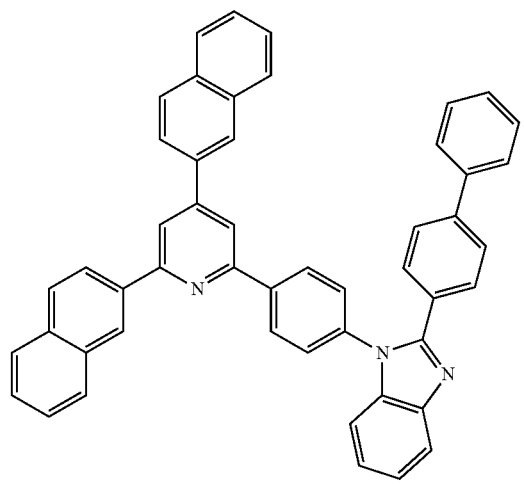
[Chemical Formula A45]
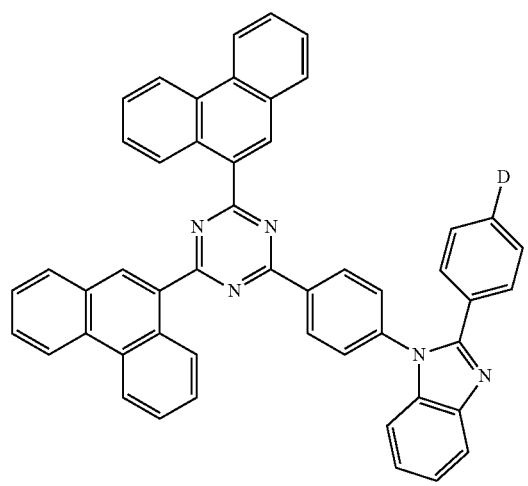
[Chemical Formula A66]
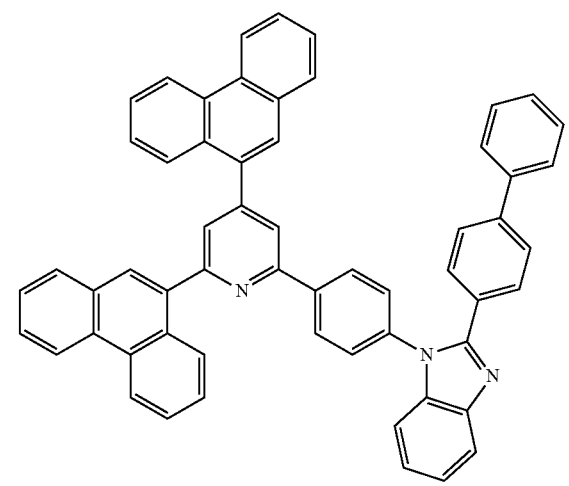

[Chemical Formula A67]
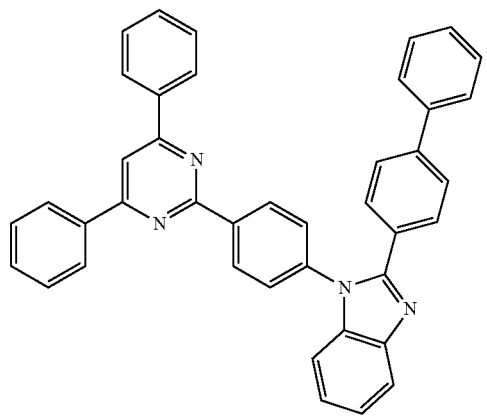
[Chemical Formula A68]
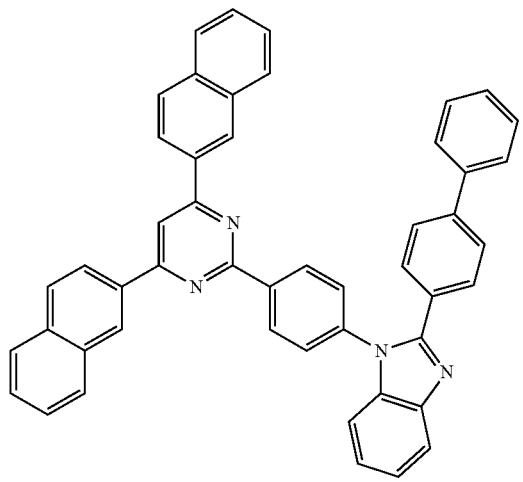
[Chemical Formula A69]
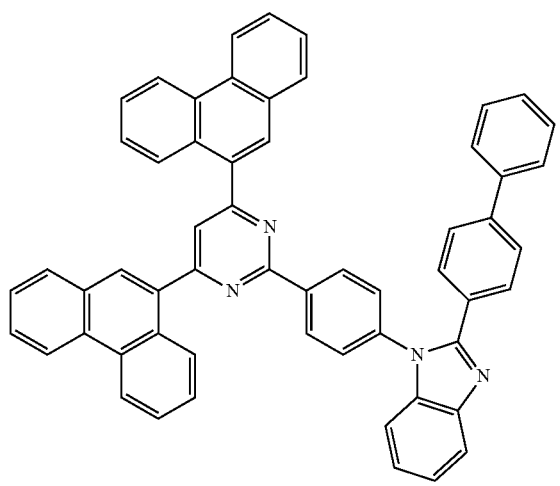
[Chemical Formula A70]
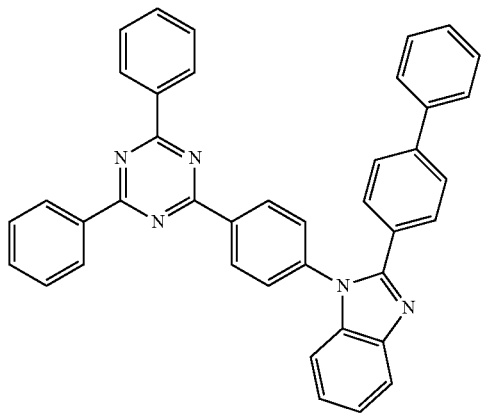
[Chemical Formula A71]
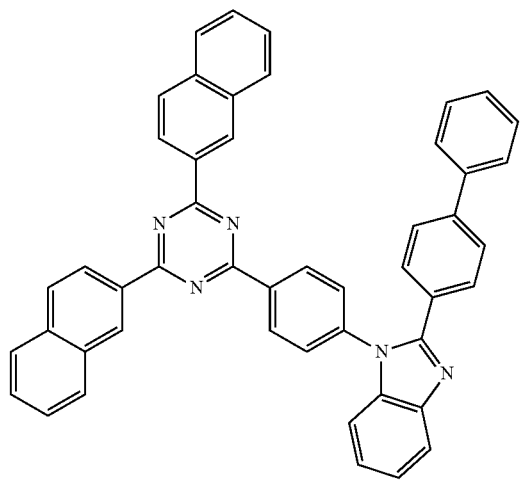
[Chemical Formula A72]
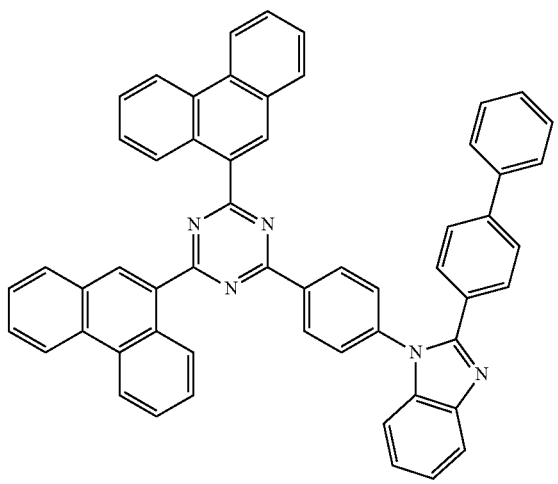
The compound may be represented by one of Chemical Formulae A46 to A63:

[Chemical Formula A46]
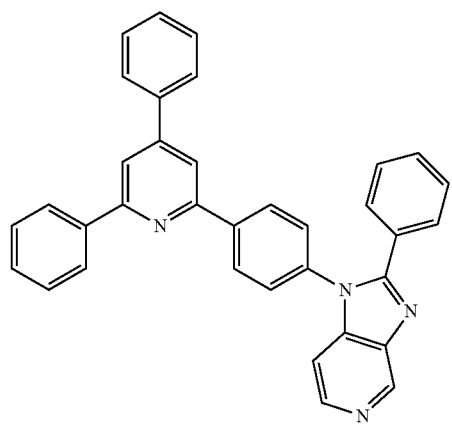
[Chemical Formula A49]
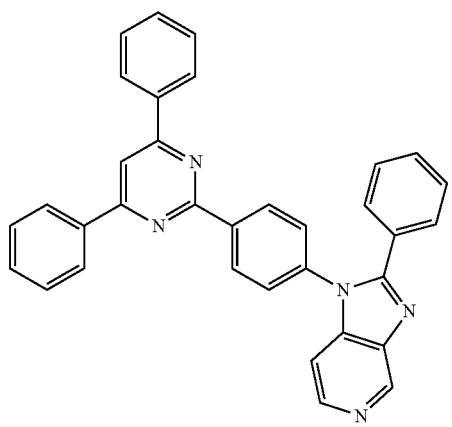
[Chemical Formula A47]
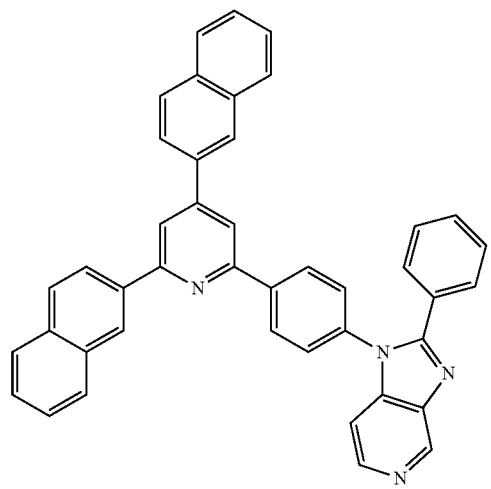
[Chemical Formula A50]
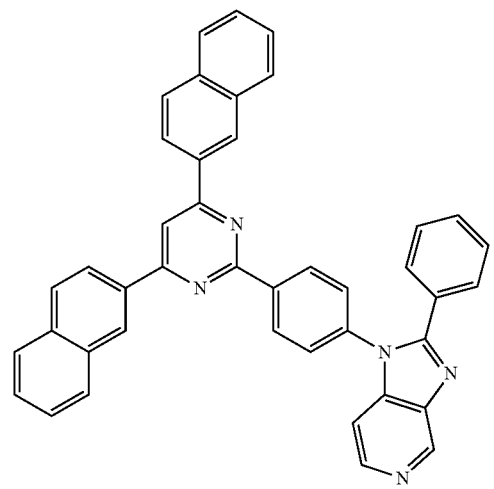
[Chemical Formula A48]
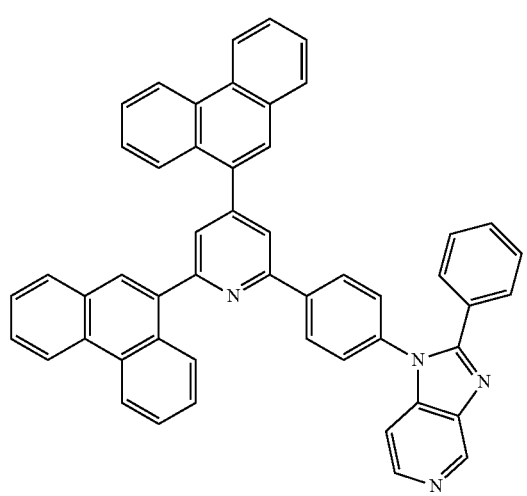
[Chemical Formula A51]
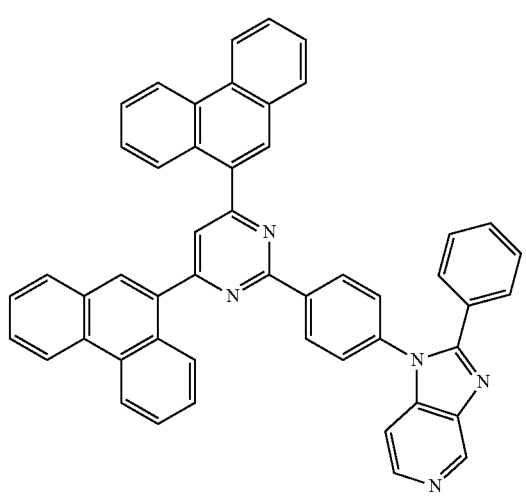

[Chemical Formula A52]
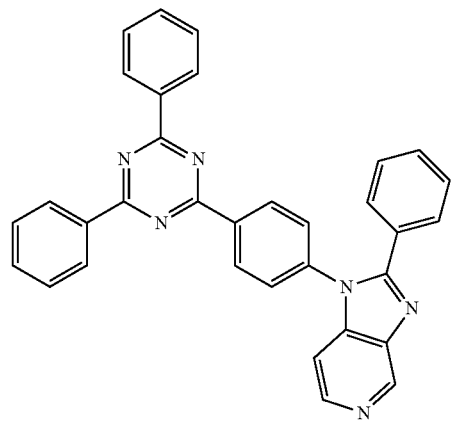
[Chemical Formula A55]
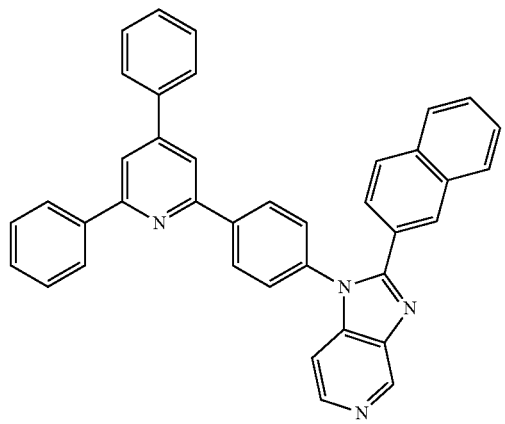
[Chemical Formula A53]
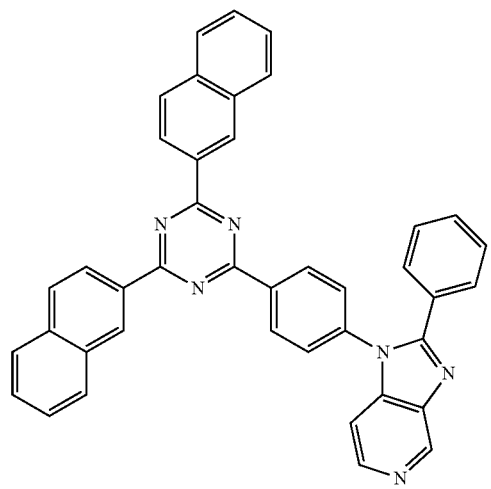
[Chemical Formula A56]
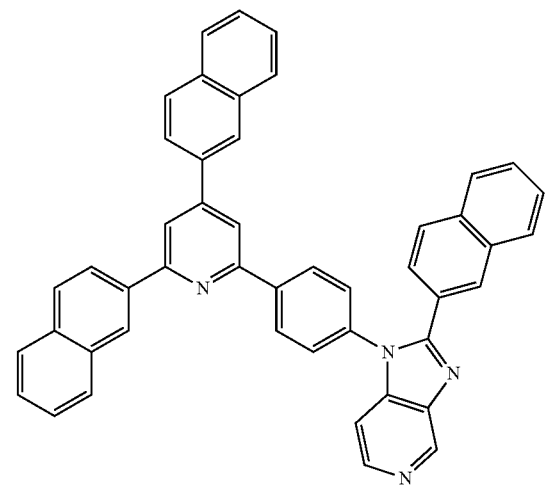
[Chemical Formula A54]
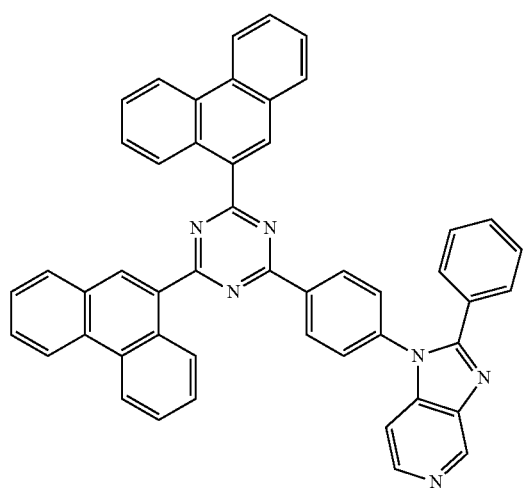
[Chemical Formula A57]
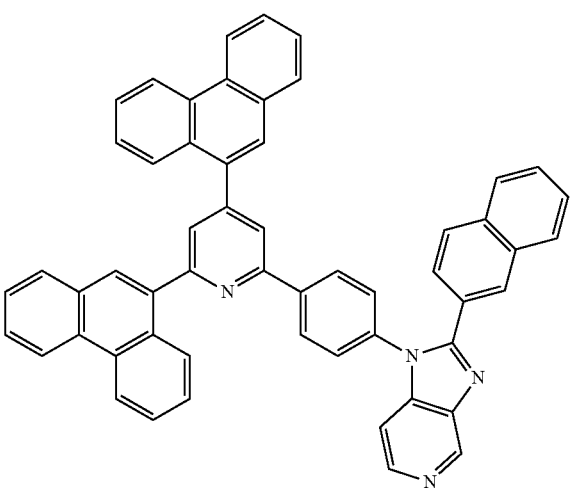

[Chemical Formula A58]
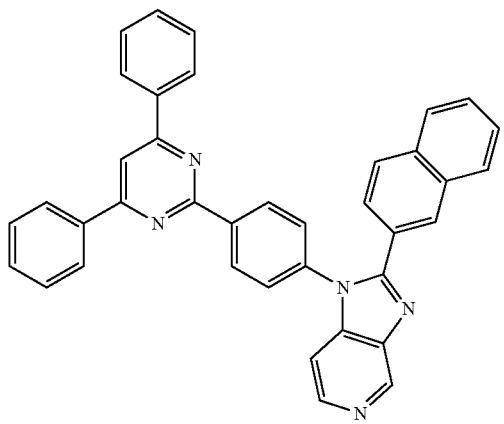
[Chemical Formula A59]
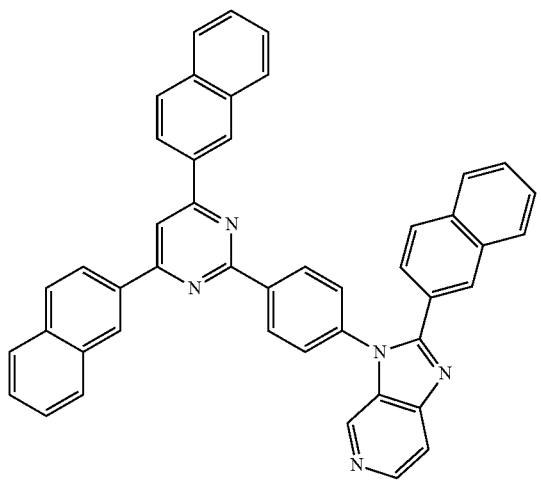
[Chemical Formula A60]
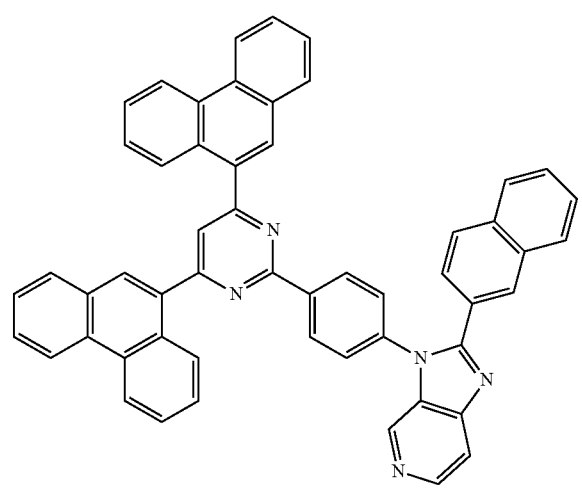
[Chemical Formula A61]
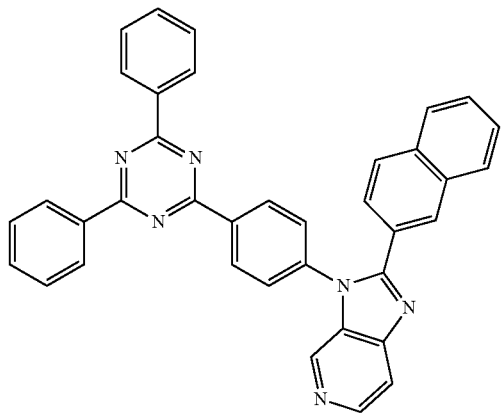
[Chemical Formula A62]
[Chemical Formula A63]
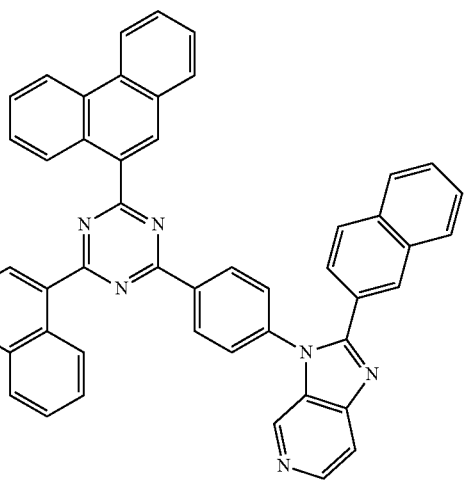
The compound may be represented by one of Chemical Formulae A73 to A90:

[Chemical Formula A73]
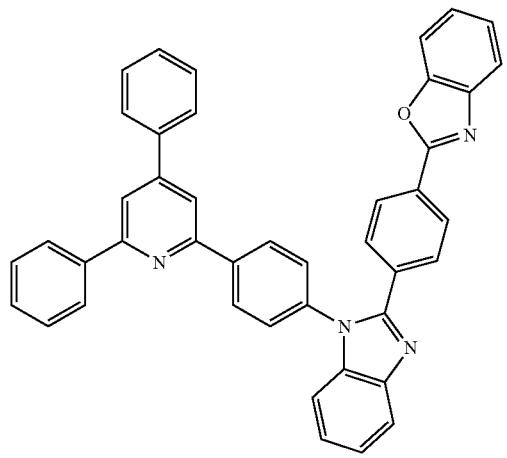
[Chemical Formula A76]
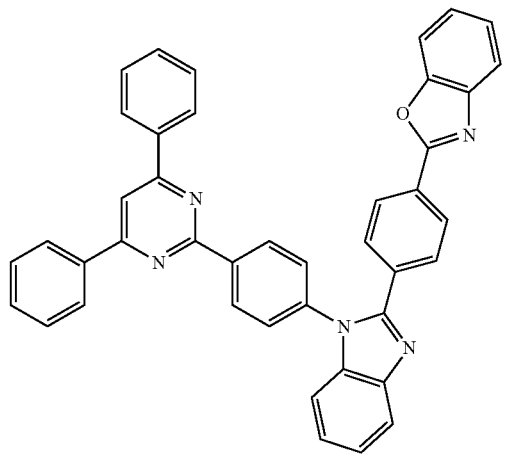
[Chemical Formula A74]
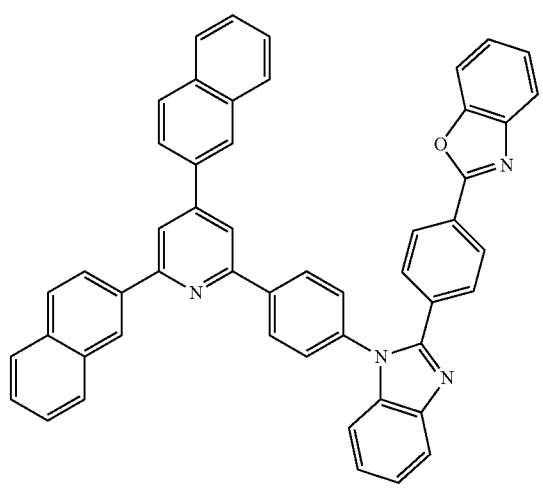
[Chemical Formula A77]
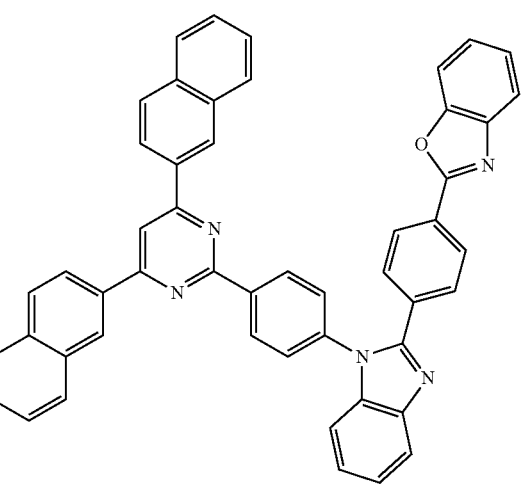
[Chemical Formula A75]
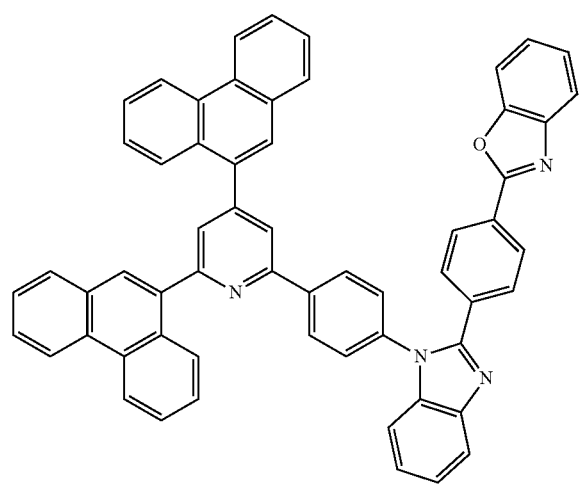
[Chemical Formula A78]

[Chemical Formula A79]
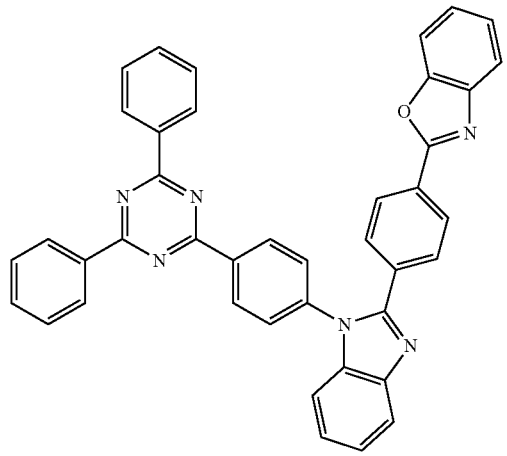
[Chemical Formula A80]
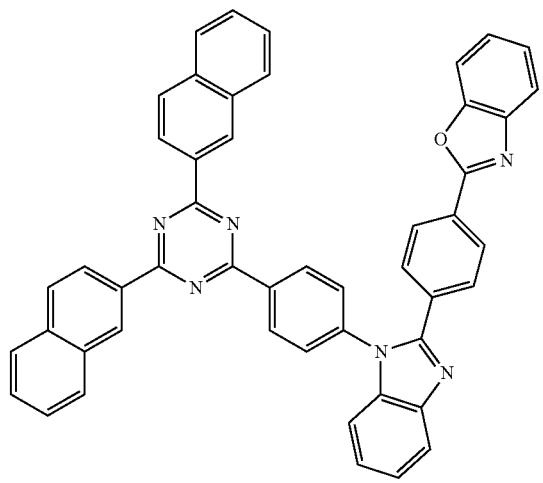
[Chemical Formula A81]
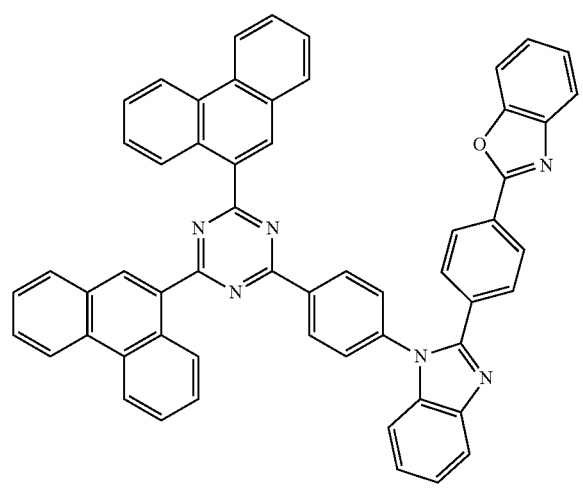
[Chemical Formula A82]
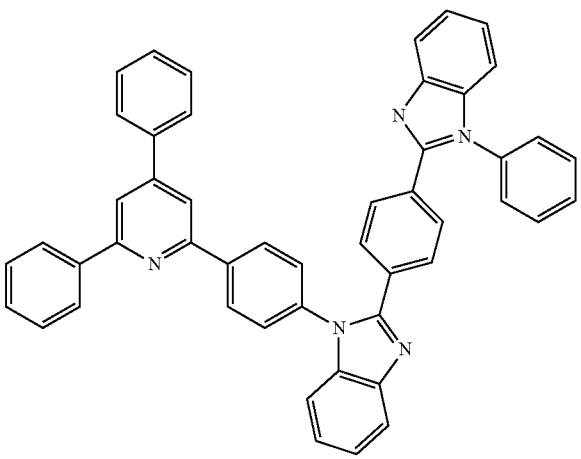
[Chemical Formula A83]
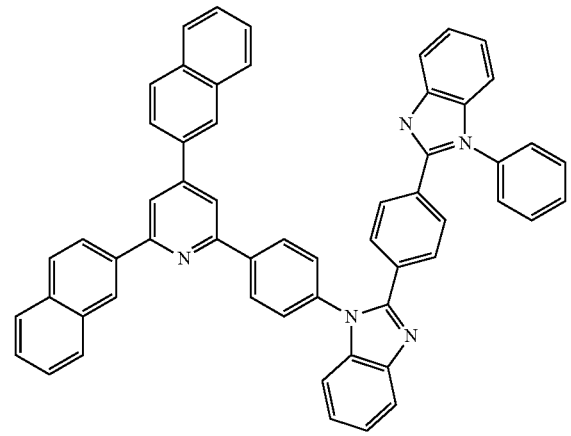
[Chemcial Formula A84]
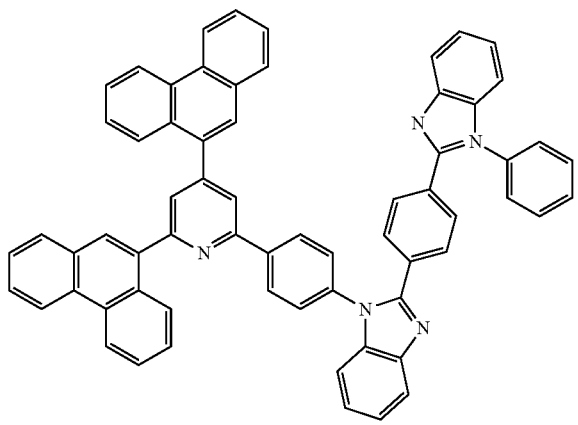

[Chemical Formula A85]
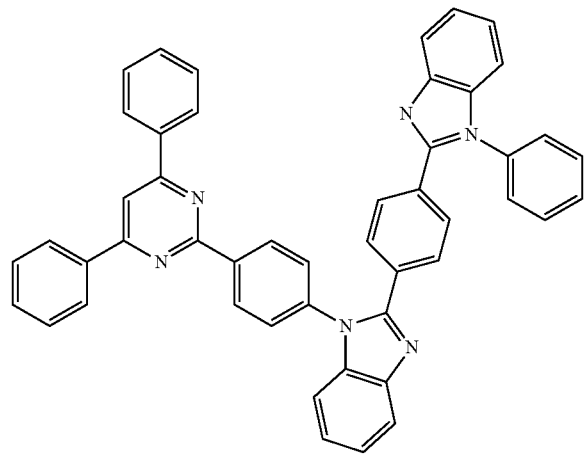
[Chemical Formula A86]
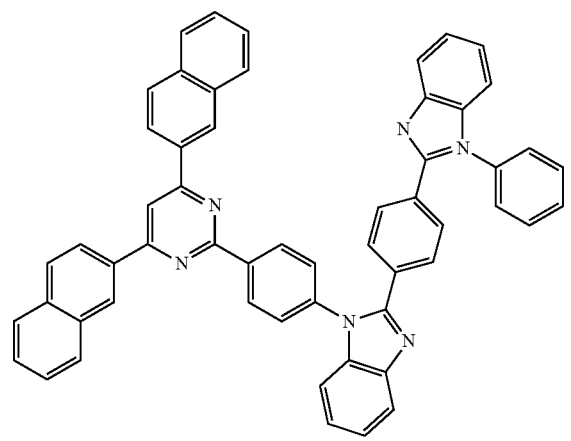
[Chemcial Formula A87]
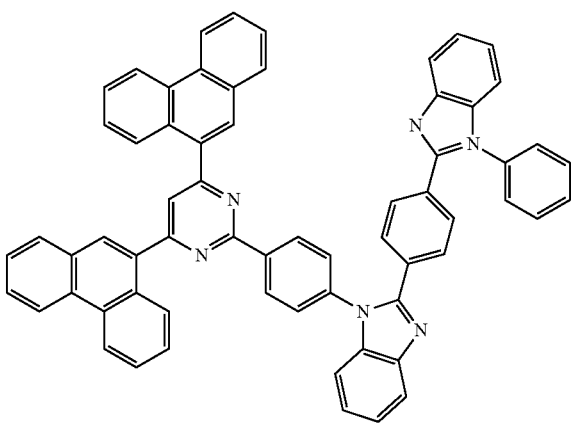
[Chemical Formula A88]
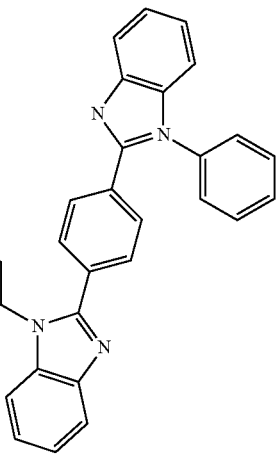
[Chemical Formula A89]
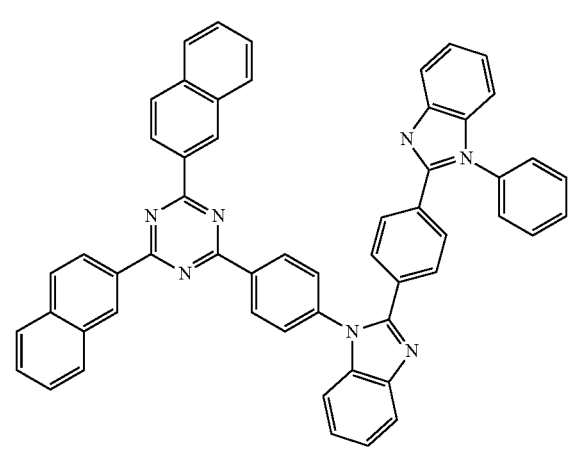
[Chemcial Formula A90]
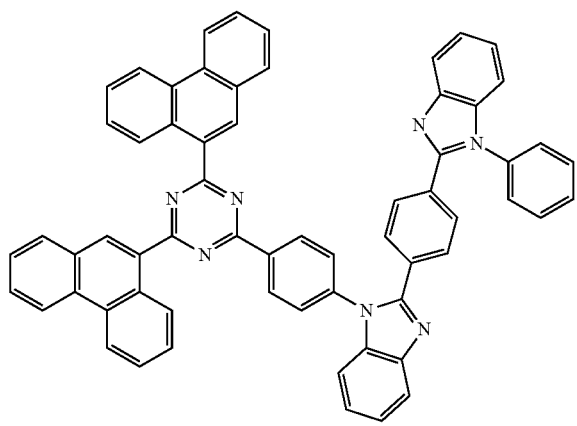
The compound may be represented by one of Chemical Formulae A91 to A99:

[Chemical Formula A91]
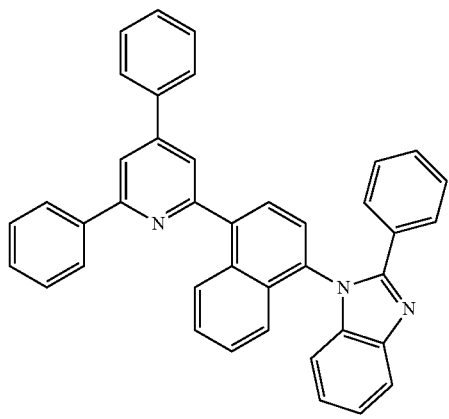
[Chemical Formula A94]
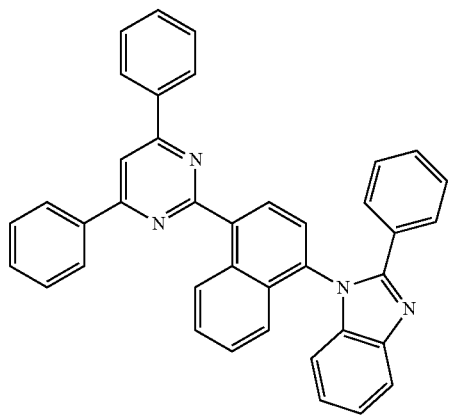
[Chemical Formula A92]
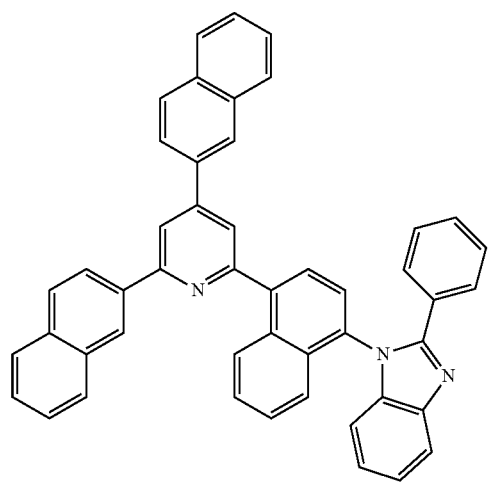
[Chemical Formula A95]
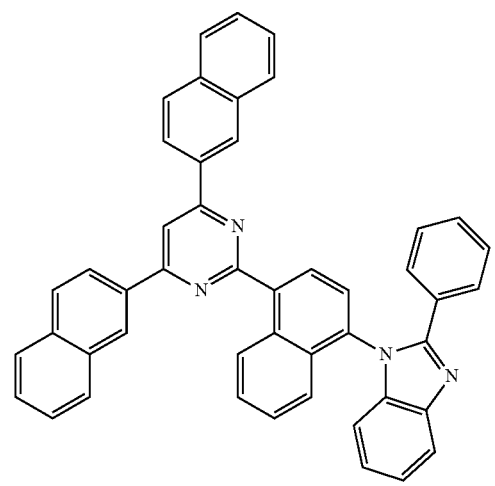
[Chemical Formula A93]
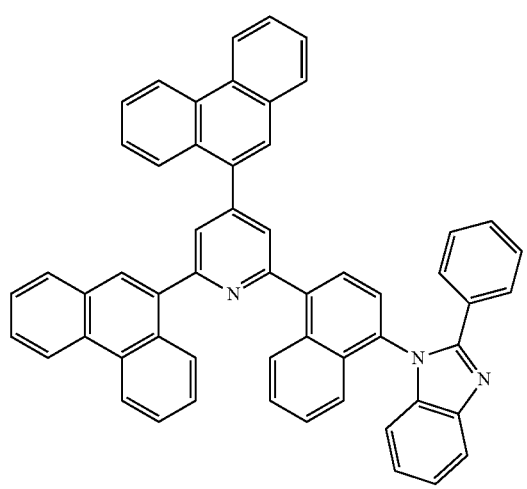
[Chemical Formula A96]
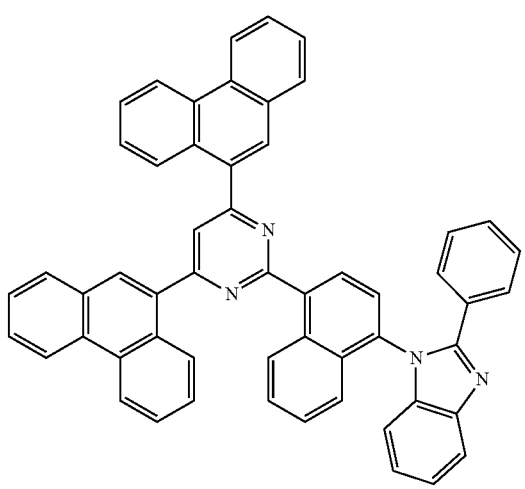

[Chemical Formula A97]

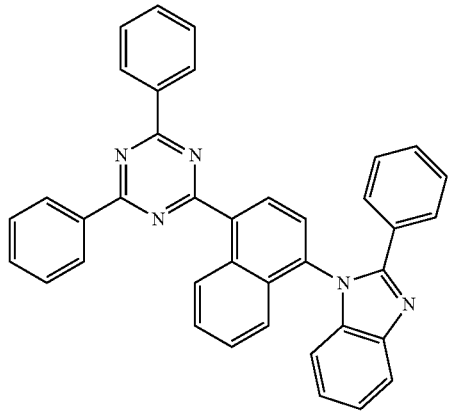

[Chemical Formula A98]

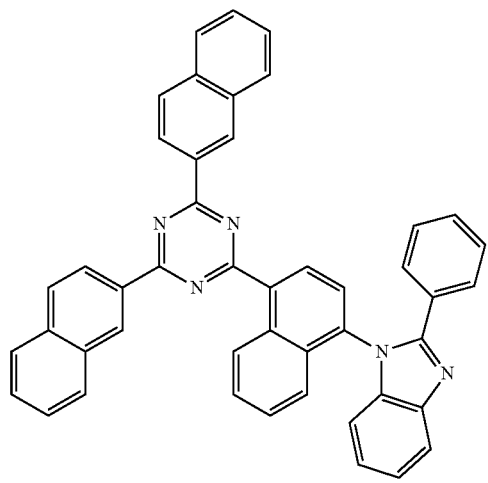

[Chemical Formula A99]

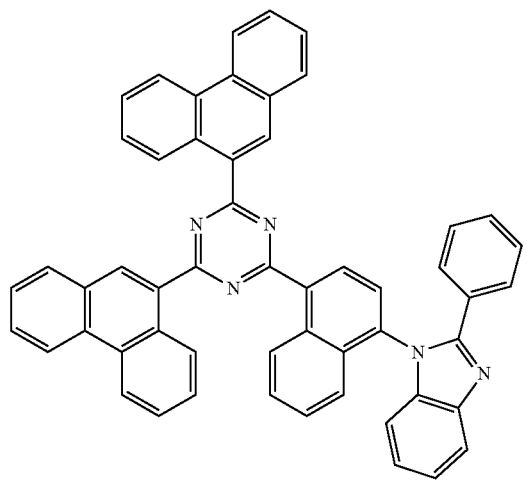

The organic optoelectronic device may be selected from the group of an organic photoelectric device, an organic light emitting diode, an organic solar cell, an organic transistor, an organic photo-conductor drum, and an organic memory device.

Embodiments are also directed to an organic light emitting diode including an anode, a cathode, and at least one organic thin layer between the anode and cathode, and the at least one organic thin layer may include the compound.

The at least one organic thin layer may be selected from the group of an emission layer, a hole transport layer, a hole injection layer, an electron transport layer, an electron injection layer, a hole blocking layer, and a combination thereof.

The at least one organic thin layer may be an electron transport layer or an electron injection layer.

The at least one organic thin layer may be an emission layer.

The at least one organic thin layer may be an emission layer, and the compound may be a phosphorescent host material or a fluorescent host material in the emission layer.

The at least one organic thin layer may be an emission layer, and the compound may be a fluorescent blue dopant material in the emission layer.

Embodiments are also directed to a display device including the organic light emitting diode.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
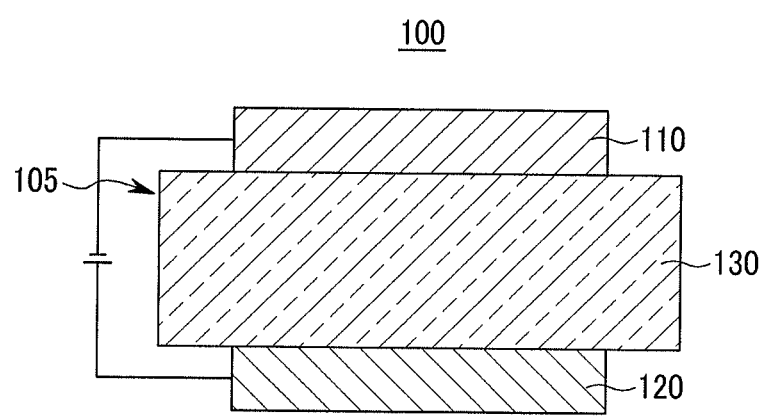
FIGS. 1 to 5 illustrate cross-sectional views of organic light emitting diodes according to various embodiments including the compound for an organic optoelectronic device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. In addition, it will also be understood that when a layer is referred to as being "between" two layers, it can be the only layer between the two layers, or one or more intervening layers may also be present. Like reference numerals refer to like elements throughout.

As used herein, when a specific definition is not otherwise provided, the term "substituted" refers to one substituted with a C1 to C30 alkyl group, a C1 to C10 alkylsilyl group, a C3 to C30 cycloalkyl group, a C6 to C30 aryl group, a C1 to C10 alkoxy group, a fluoro group, C1 to C10 trifluoroalkyl group such as a trifluoromethyl group, and the like, or a cyano group.

As used herein, when a specific definition is not otherwise provided, the term "hetero" refers to one including 1 to 3 hetero atoms selected from the group of N, O, S, and P, and the remaining being carbons in one functional group.

As used herein, when a definition is not otherwise provided, the term "combination thereof" refers to at least two substituents bound to each other by a linker, or at least two substituents condensed to each other.

In the specification, when a definition is not otherwise provided, the term "alkyl group" may refer to an aliphatic hydrocarbon group. The alkyl group may be a saturated group without any alkene group or alkyne group. The alkyl group may be branched, linear, or cyclic. The "alkene group" may refer to a substituent with at least one carbon-carbon double bond of at least two carbons, and the "alkyne group" may refer to a substituent with at least one carbon-carbon triple bond of at least two carbons.

The alkyl group may be a C1 to C20 alkyl group. The alkyl group may be a C1 to C10 medium-sized alkyl group. The alkyl group may be a C1 to C6 lower alkyl group. For example, a C1 to C4 alkyl group may have 1 to 4 carbon atoms and may be selected from the group of methyl, ethyl, propyl, iso-propyl, n-butyl, iso-butyl, sec-butyl, and t-butyl.

Examples of an alkyl group may be individually and independently selected from a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like or a functional group substituted with one or more of the foregoing groups.

The "aromatic group" may refer to a substituent including all elements of the cycle having p-orbitals which form a conjugation. Examples may include an aryl group and a heteroaryl group.

The "aryl group" may refer to a monocyclic or a fused ring polycyclic (i.e., rings sharing adjacent pairs of carbon atoms) substituent.

The "heteroaryl group" may refer to an aryl group including 1 to 3 hetero atoms selected from the group of N, O, S, and P, and the remaining being carbons in one functional group.

"Spiro structure" may refer to a plurality of cyclic structures having a contact point of one carbon. The Spiro structure may include a compound having a spiro structure or a substituent having a spiro structure.

According to an embodiment, a compound for an organic optoelectronic device represented by the following Chemical Formula 1 is provided.

[Chemical Formula 1]

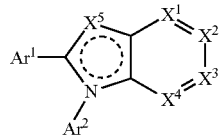

In Chemical Formula 1, $X^1$ to $X^4$ each independently may be —N—, —$CR^1$—, —$CR^2$—, —$CR^3$—, or —$CR^4$—, $X^5$ may be —O—, —S—, —Se—, or —N—, $R^1$ to $R^4$ each independently may be hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof. One of $Ar^1$ or $Ar^2$ may be a substituted or unsubstituted C6 to C30 aryl group, or a substituted or unsubstituted C3 to C30 heteroaryl group, and the other of $Ar^1$ or $Ar^2$ may be a substituent represented by the following Chemical Formula 2.

[Chemical Formula 2]

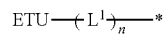

In Chemical Formula 2, * is a bonding site of the substituent represented by Chemical Formula 2 in Chemical Formula 1, $L^1$ may be a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n may be an integer from 0 to 2, and ETU may be a substituted or unsubstituted C3 to C30 heteroaryl group having electronic properties.

The compound for an organic optoelectronic device represented by the above Chemical Formula 1 according to an embodiment may have a structure including a substituent having electronic properties in a fused ring core including at least one nitrogen atom. The compound may control (affect) the characteristics of the entire compound by introducing an appropriate substituent in the core structure having excellent electronic properties.

The compound for an organic optoelectronic device may include a core part and various substituents for substituting the core part, and thus may have various energy band gaps. The compound may be used in a hole injection layer (HIL) and transport layer, or an emission layer.

The compound may have an appropriate energy level depending on the substituents, and thus may improve electron transport capability of an organic optoelectronic device and allow improvements in efficiency and driving voltage. Also, the compound may have excellent electrochemical and thermal stability, and thus may improve life-span characteristic during the operation of the organic optoelectronic device.

The electronic properties refer to characteristic such that an electron formed in the cathode is easily injected into the emission layer and transported in the emission layer due to conductive properties according to LUMO level.

On the contrary, hole properties refer to characteristic such that a hole formed in the anode is easily injected into the emission layer and transported in the emission layer due to conductive characteristic according to HOMO level.

The structure may have asymmetric bipolar characteristics by appropriately blending and/or selecting substituents. The structure having asymmetric bipolar characteristics may improve the electron transport properties, and thus the luminous efficiency and the performance of the device using the same may be improved.

The substituent represented by the above Chemical Formula 2 may be a substituent represented by the following Chemical Formula 3.

[Chemical Formula 3]

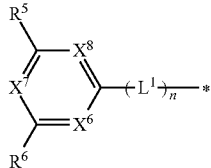

In Chemical Formula 3, $X^6$ to $X^8$ each independently may be —N— or R' may be hydrogen or deuterium, at least one of $X^6$ to $X^8$ may be —N—, $L^1$ may be a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n may be an integer from 0 to 2, and $R^5$ and $R^6$ each independently may be hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof.

The molecules may be easily arranged by applying the more rigid structure, e.g., by having the substituent represented by Chemical Formula 3, and thus the electron transport properties of the entire compound may be improved.

An example of the compound represented by the above Chemical Formula 1 may be represented by the following Chemical Formula 4.

[Chemical Formula 4]

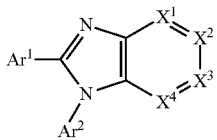

In Chemical Formula 4, $X^1$ to $X^4$ each independently may be —N—, —$CR^1$—, —$CR^2$—, —$CR^3$—, or —$CR^4$—, $R^1$ to $R^4$ each independently may be hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof. One of $Ar^1$ or $Ar^2$ may be a substituted or unsubstituted C6 to C30 aryl group, or a substituted or unsubstituted C3 to C30 heteroaryl group, and the other of $Ar^1$ or $Ar^2$ may be a substituent represented by the following Chemical Formula 2.

[Chemical Formula 2]

$$ETU-(L^1)_n-*$$

In Chemical Formula 2, $L^1$ may be a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n may be an integer from 0 to 2, and ETU may be a substituted or unsubstituted C3 to C30 heteroaryl group having electronic properties.

When the compound is represented by Chemical Formula 4 (i.e., when the atom represented by $X^5$ in Chemical Formula 1 is nitrogen), electron injection may be improved by decreasing energy level.

The compound for an organic optoelectronic device may be represented by the following Chemical Formula 5 or 6.

[Chemical Formula 5]

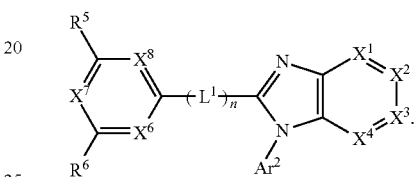

In Chemical Formula 5, $X^1$ to $X^4$ each independently may be —N—, —$CR^1$—, —$CR^2$—, —$CR^3$—, or —$CR^4$—, the $R^1$ to $R^4$ each independently may be hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, $Ar^2$ may be a substituted or unsubstituted C6 to C30 aryl group, or substituted or unsubstituted C3 to C30 heteroaryl group, L' may be a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n may be an integer from 0 to 2, $X^6$ to $X^8$ each independently may be —N— or —$CR^1$—, R' may be hydrogen or deuterium, at least one of $X^6$ to $X^8$ may be —N—, and $R^5$ and $R^6$ each independently may be hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof.

[Chemical Formula 6]

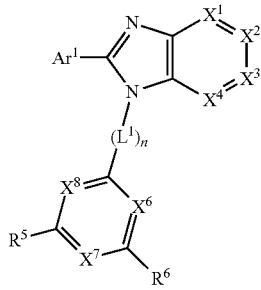

In Chemical Formula 6, $X^1$ to $X^4$ each independently may be —N—, —$CR^1$—, —$CR^2$—, —$CR^3$—, or —$CR^4$—, the $R^1$ to $R^4$ each independently may be hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, Ar$^1$ may be a substituted or unsubstituted C6 to C30 aryl group, or substituted or unsubstituted C3 to C30 heteroaryl group, L' may be a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n may be an integer from 0 to 2, X$^6$ to X$^8$ each independently may be —N— or —CR$^1$—, R' may be hydrogen or deuterium, at least one of X$^6$ to X$^8$ may be —N—, and R$^5$ and R$^6$ each independently may be hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof.

The structures of Chemical Formulae 5 and 6 are different from each other based on the bonding positions of the substituent represented by Chemical Formula 2 in the structure of Chemical Formula 1. That is, the difference between structures of Chemical Formulae 5 and 6 depends upon the position of substituent bound to the hetero fused ring core.

When having the bonding position such as Chemical Formula 5, the thermal properties of the compound may be enforced or enhanced by introducing the rigid molecular structure. When a device is fabricated using the compound for an organic optoelectronic device, the thermal resistance may be improved.

When having the bonding position such as Chemical Formula 6, the amorphous characteristics of compound may be enforced or enhanced to suppress the crystalline (e.g., crystallization), and thus the device using the same may prolong a life span.

In the above Chemical Formulae 5 and 6, R$^5$ and R$^6$ each independently may be a substituted or unsubstituted naphthyl group, a substituted or unsubstituted anthracenyl group, a substituted or unsubstituted phenanthrenyl group, a substituted or unsubstituted triphenylenyl group, a substituted or unsubstituted pyrenyl group, a substituted or unsubstituted chrysenyl group, or a combination thereof. When having the substituent, the core may be more asymmetric to decrease the crystallinity of the compound, and when the organic optoelectronic device is fabricated using the compound having low crystallinity, the life-span of device may be improved.

The substituted or unsubstituted C3 to C30 heteroaryl group having the electronic properties may be a substituted or unsubstituted imidazolyl group, a substituted or unsubstituted triazolyl group, a substituted or unsubstituted tetrazolyl group, a substituted or unsubstituted carbazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof, but is not limited thereto.

Examples of L$^1$ may be a substituted or unsubstituted ethenylene, a substituted or unsubstituted ethynylene, a substituted or unsubstituted phenylene, a substituted or unsubstituted biphenylene, a substituted or unsubstituted naphthalene, a substituted or unsubstituted pyridinylene, a substituted or unsubstituted pyrimidinylene, a substituted or unsubstituted triazinylene, and the like.

The substituent may have a pi bond, and thus the substituent may increase triplet energy band gap by adjusting the entire π-conjugation length of the compound, such that the compound may be usefully applied for an emission layer of organic optoelectronic device as a phosphorescent host. However, since n may be 0, the linking group such as L$^1$ may not exist (may not be present), e.g., such that a single bond may connect the ETU moiety in Chemical Formula 1.

The compound for an organic optoelectronic device may be represented by one of the following Chemical Formulae A1 to A99, but is not limited thereto.

[Chemical Formula A1]

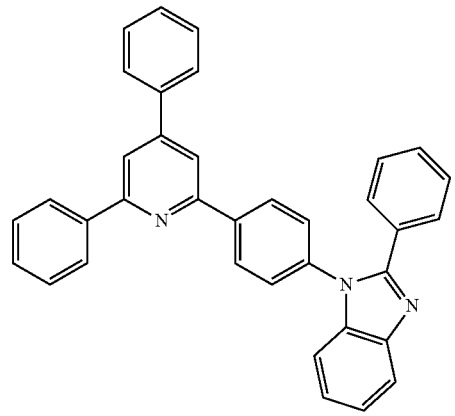

[Chemical Formula A2]

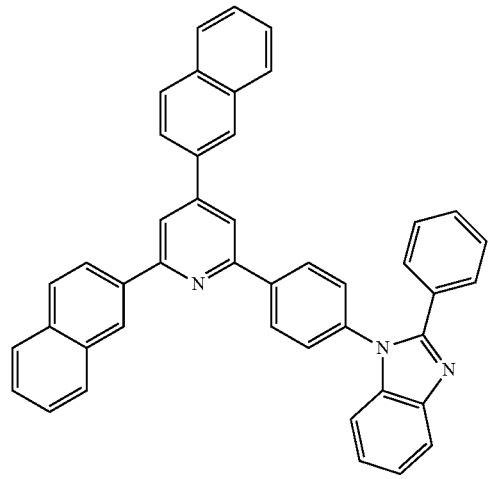

[Chemical Formula A3]
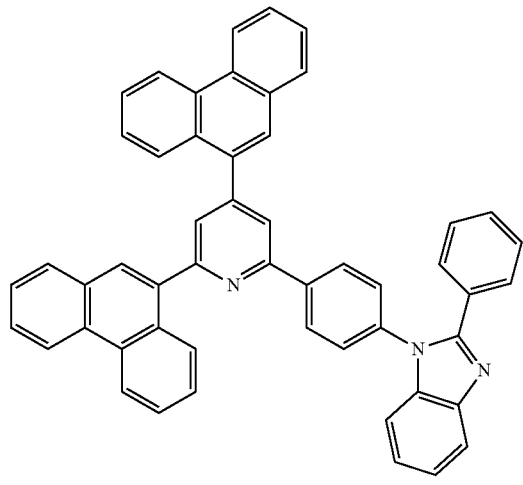
[Chemical Formula A4]
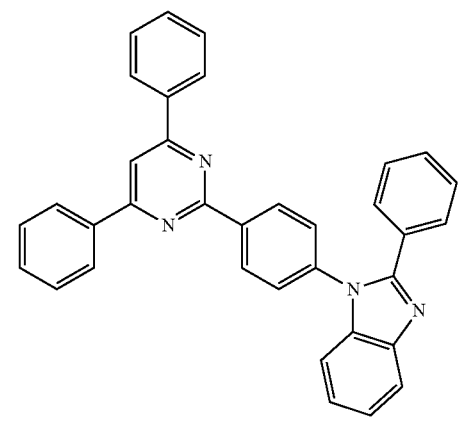
[Chemical Formula A5]
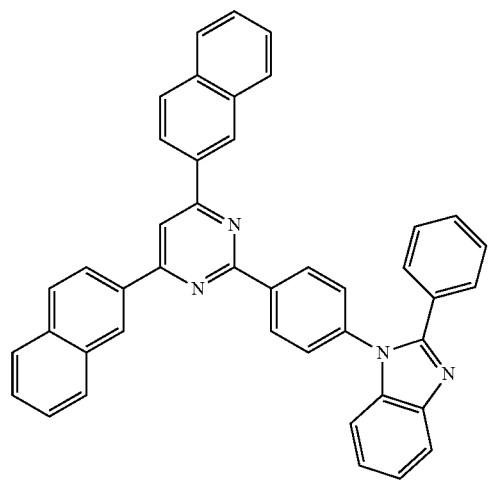
[Chemical Formula A6]
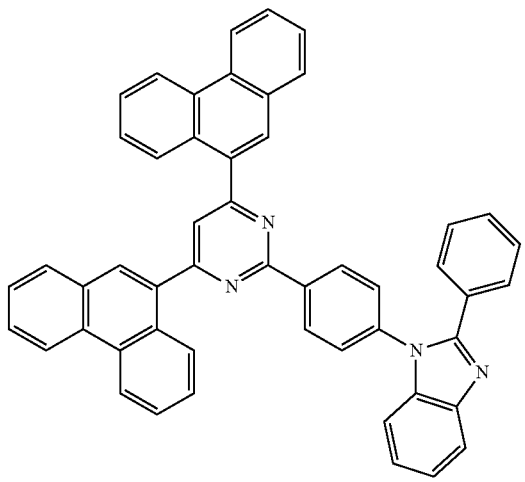
[Chemical Formula A7]
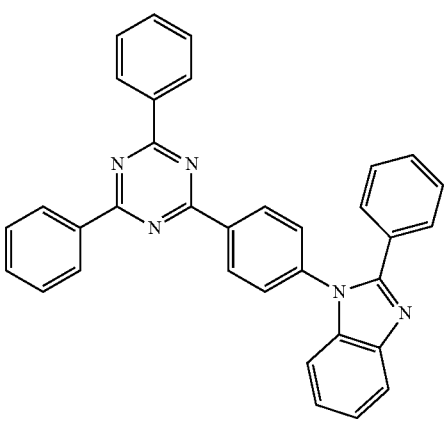
[Chemical Formula A8]
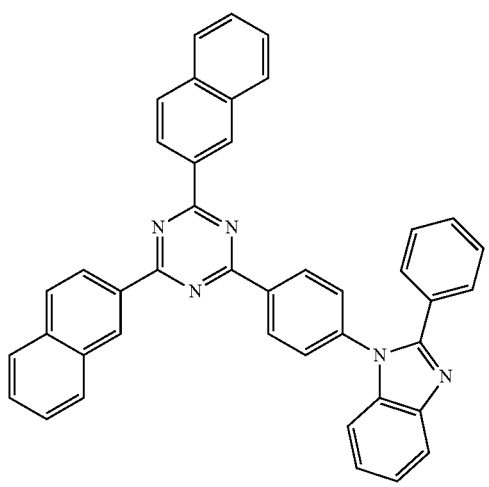

[Chemical Formula A9]
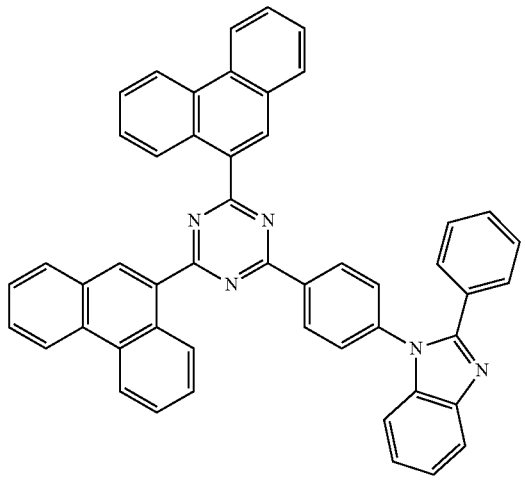
[Chemical Formula A10]
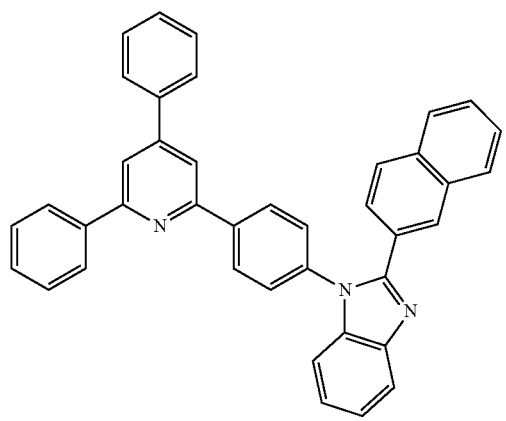
[Chemical Formula A11]
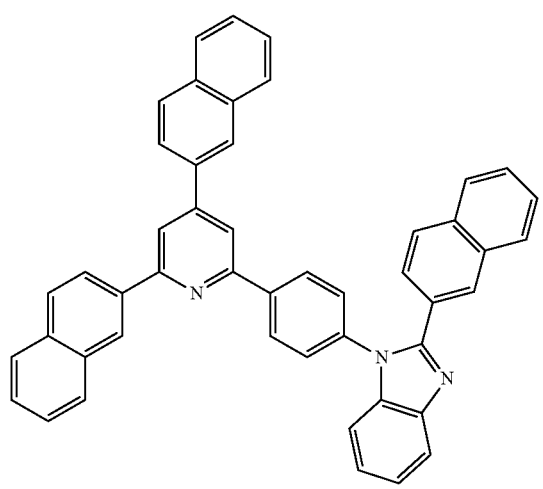
[Chemical Formula A12]
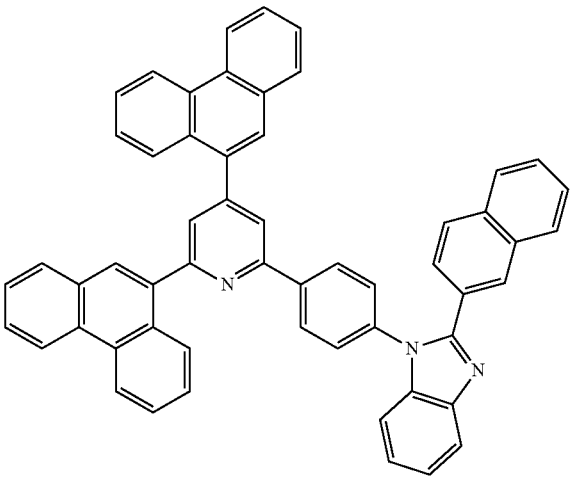
[Chemical Formula A13]
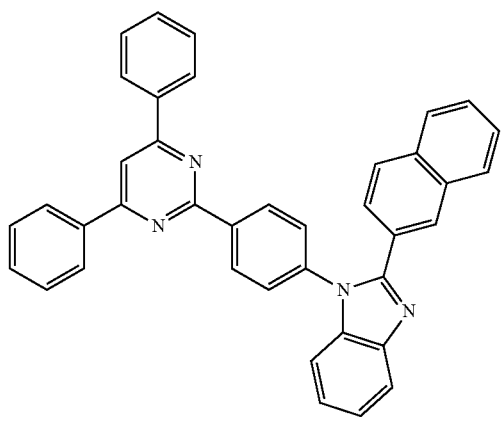
[Chemical Formula A14]
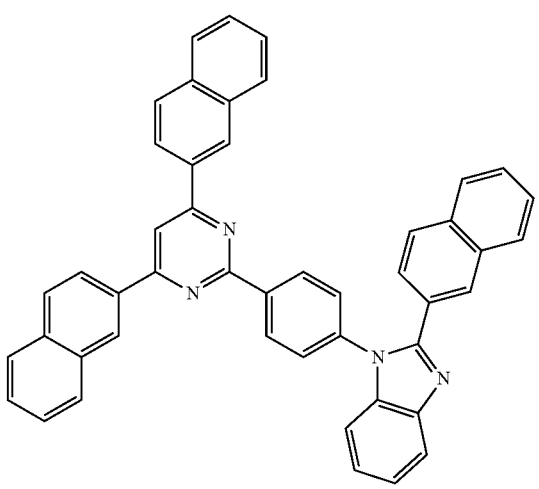

[Chemical Formula A15]
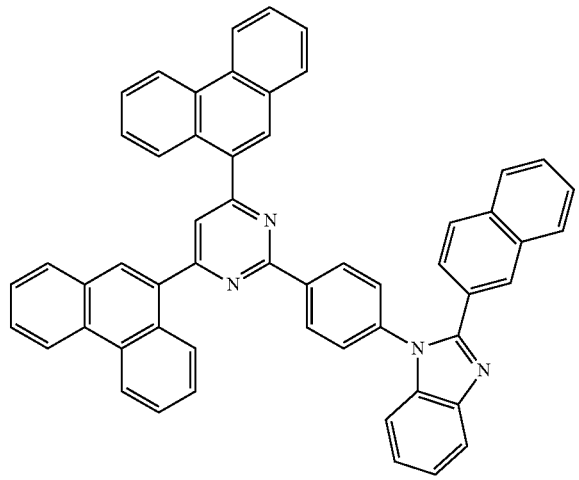
[Chemical Formula A16]
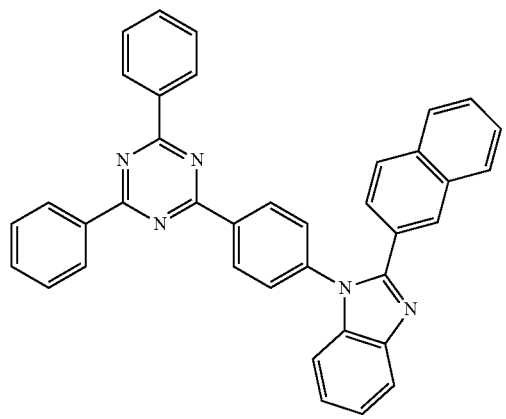
[Chemical Formula A17]
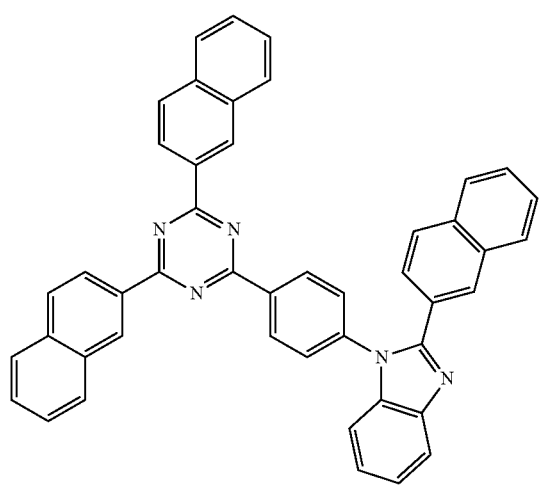
[Chemical Formula A18]
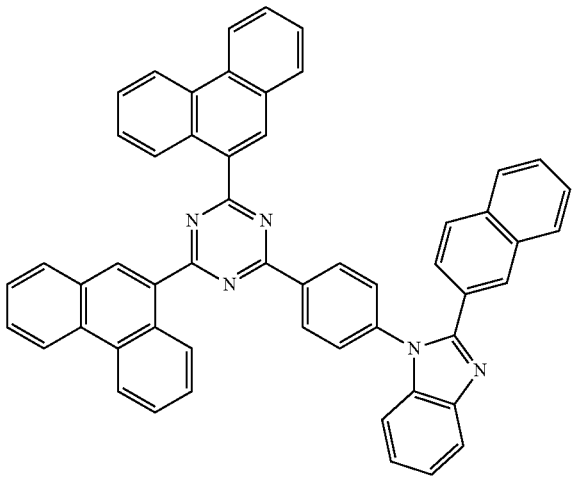
[Chemical Formula A19]
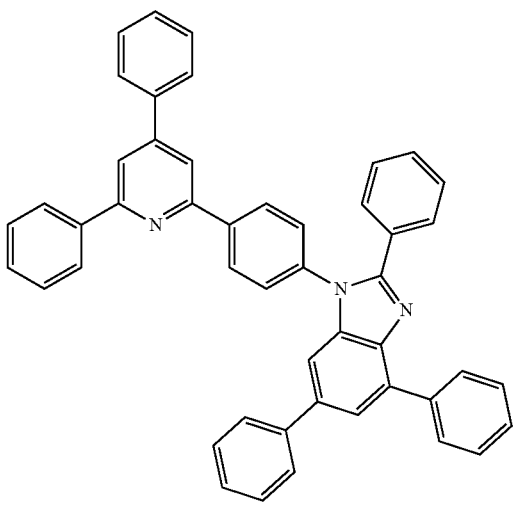
[Chemical Formula A20]
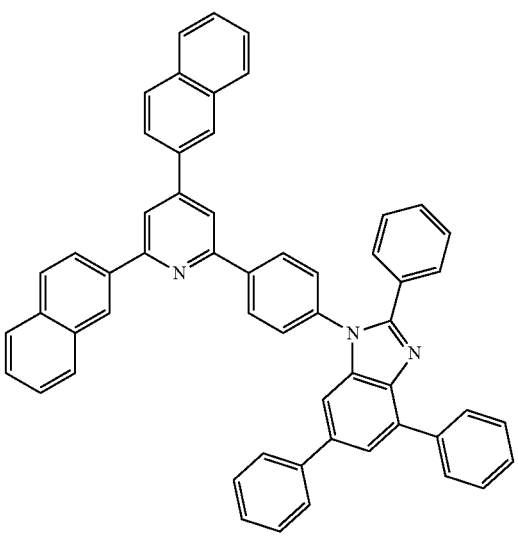

[Chemical Formula A21]
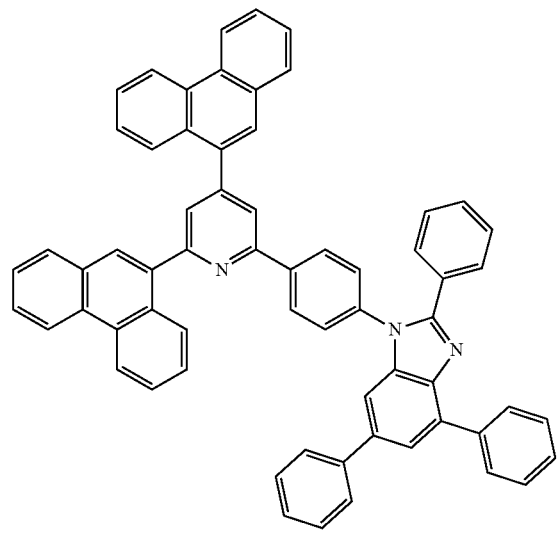
[Chemical Formula A22]
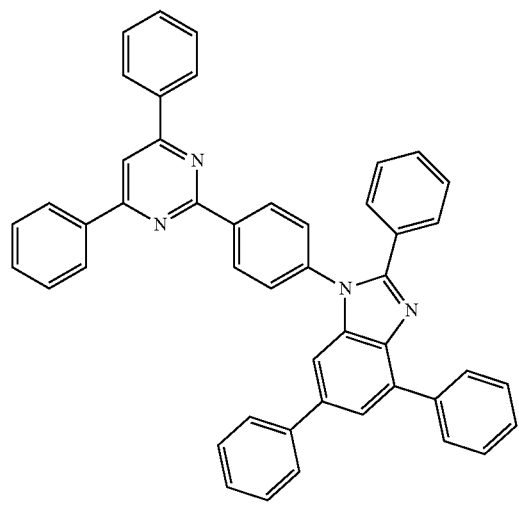
[Chemical Formula A23]
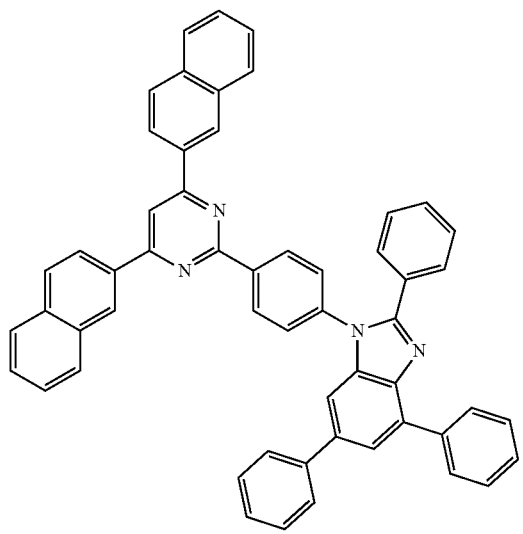
[Chemical Formula A24]
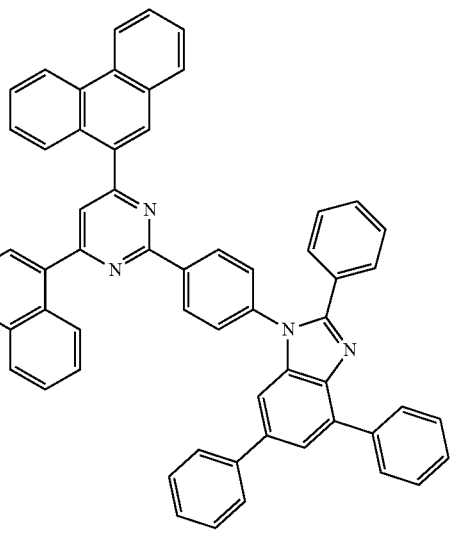
[Chemical Formula A25]
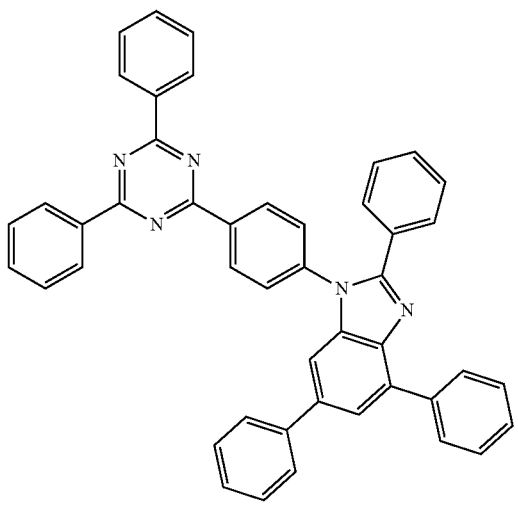
[Chemical Formula A26]
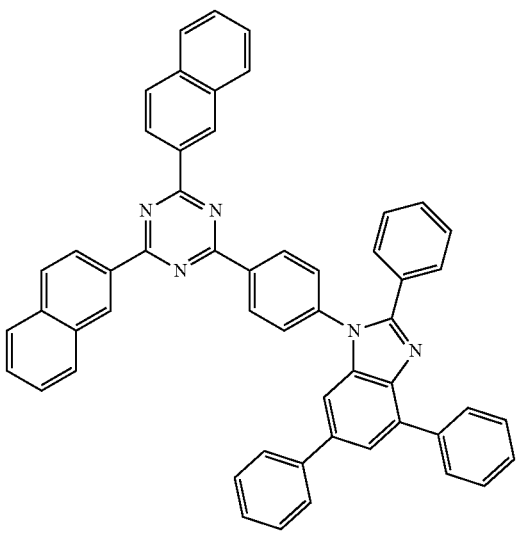

[Chemical Formula A27]
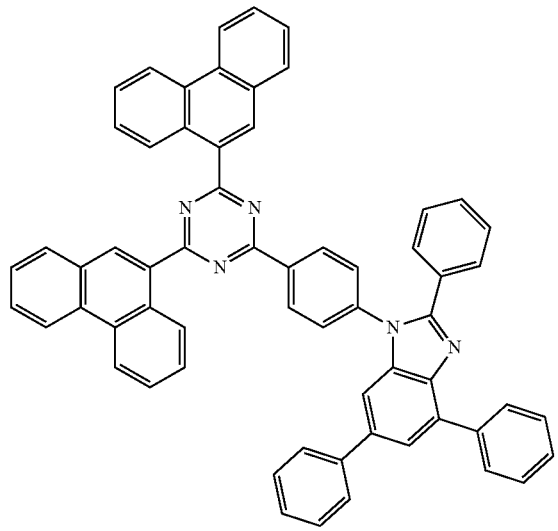
[Chemical Formula A28]
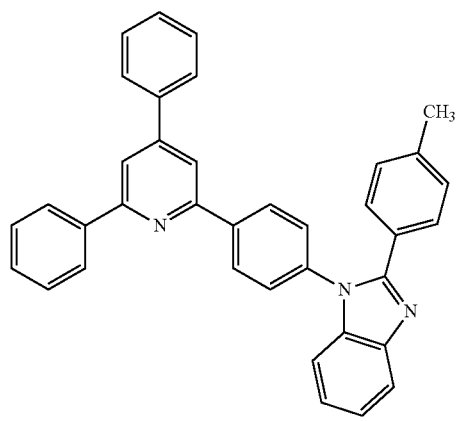
[Chemical Formula A29]
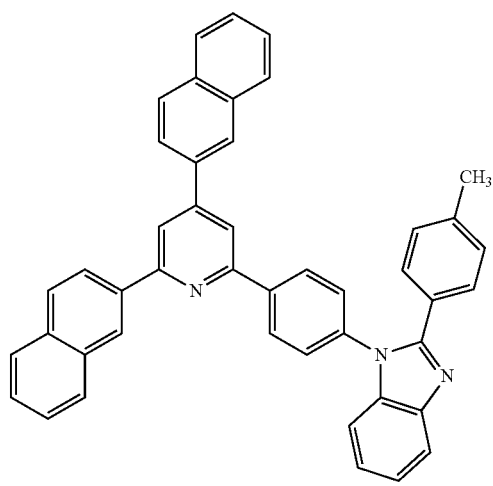
[Chemical Formula A30]
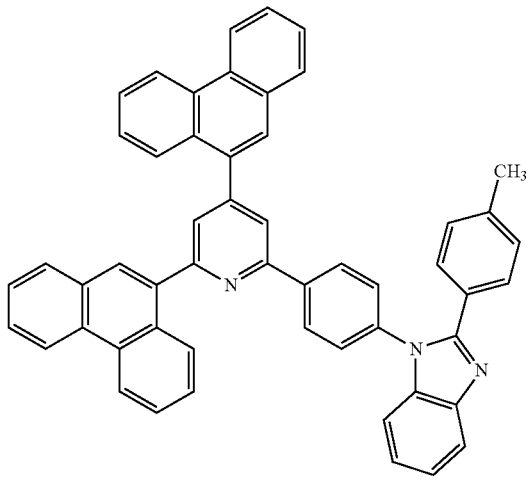
[Chemical Formula A31]
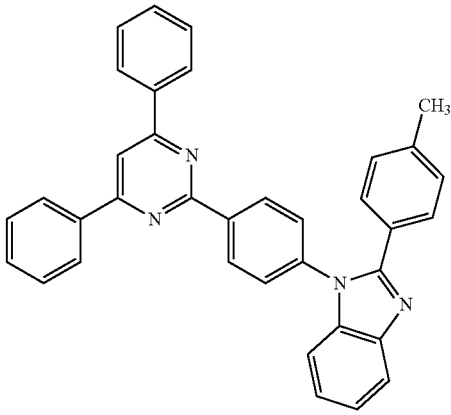
[Chemical Formula A32]
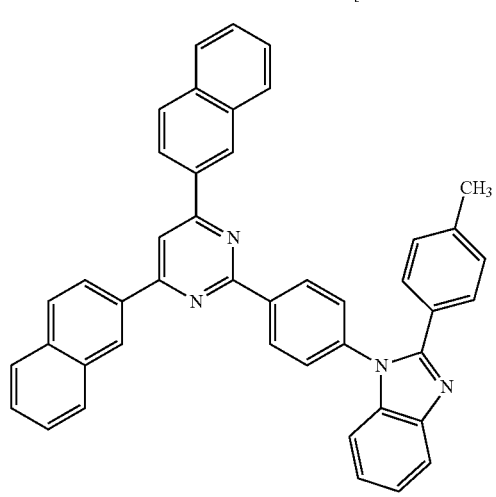

[Chemical Formula A33]
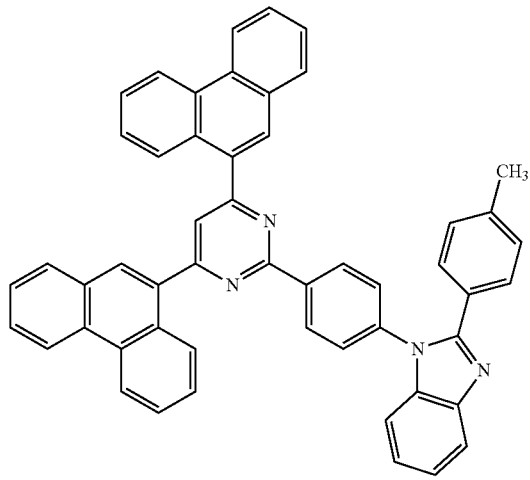
[Chemical Formula A34]
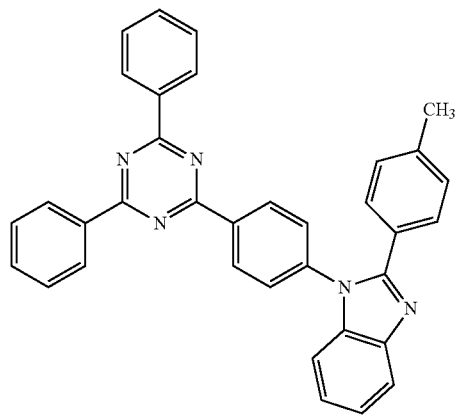
[Chemical Formula A35]
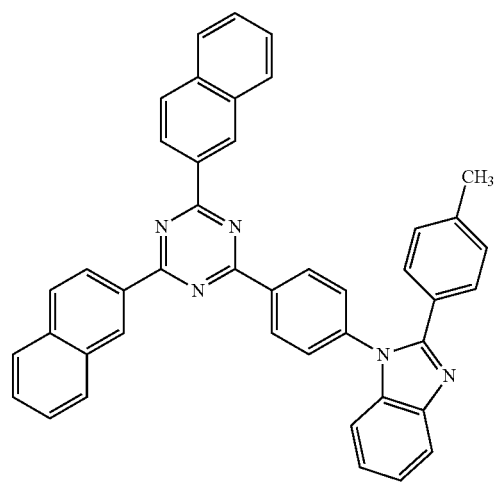
[Chemical Formula A36]
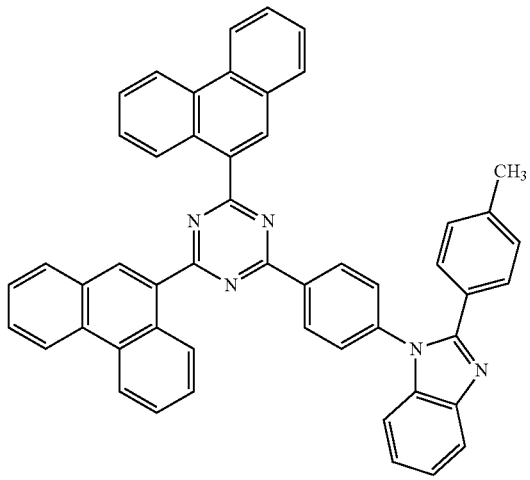
[Chemical Formula A37]
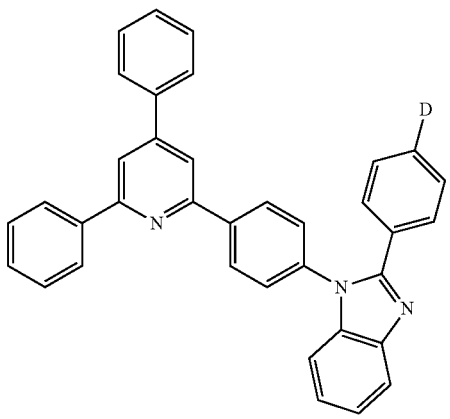
[Chemical Formula A38]
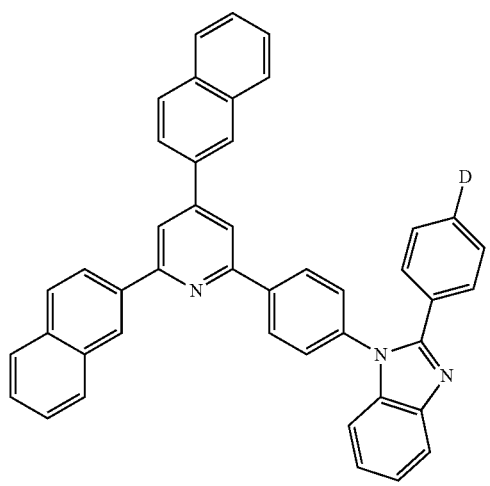

[Chemical Formula A39]
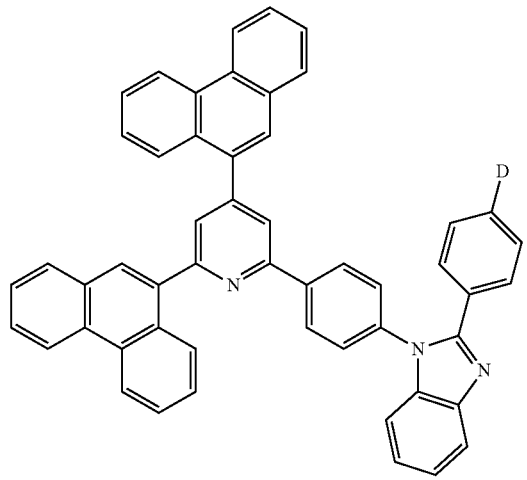
[Chemical Formula A40]
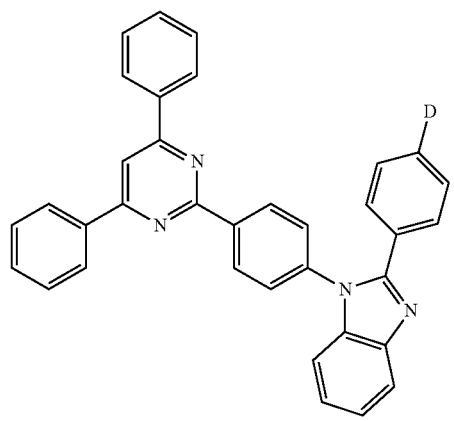
[Chemical Formula A41]
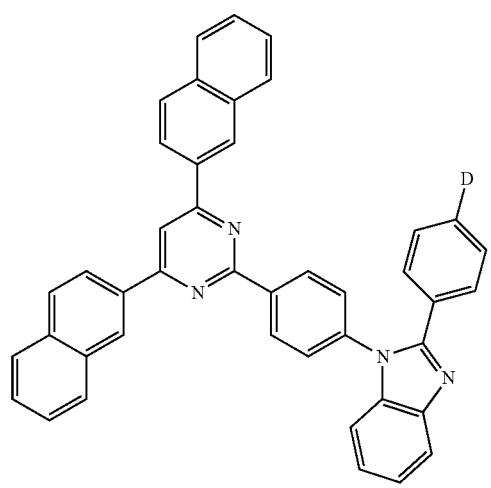
[Chemical Formula A42]
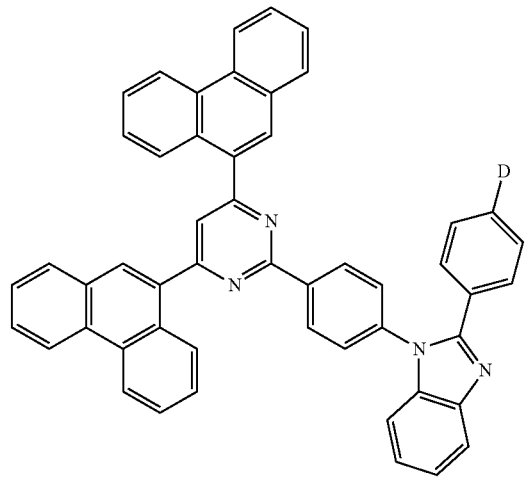
[Chemical Formula A43]
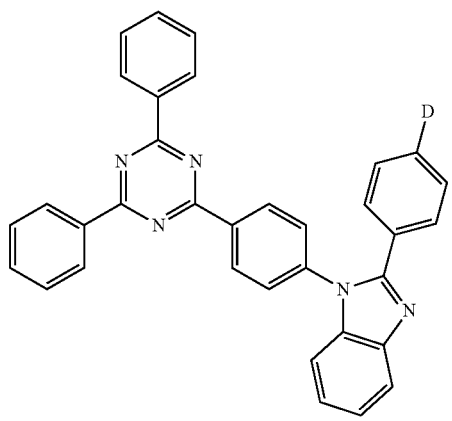
[Chemical Formula A44]
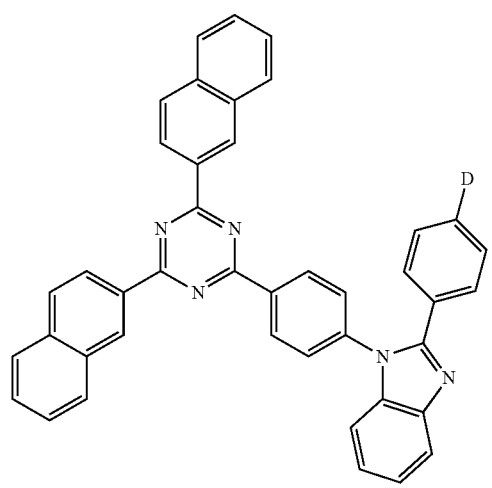

[Chemical Formula A45]
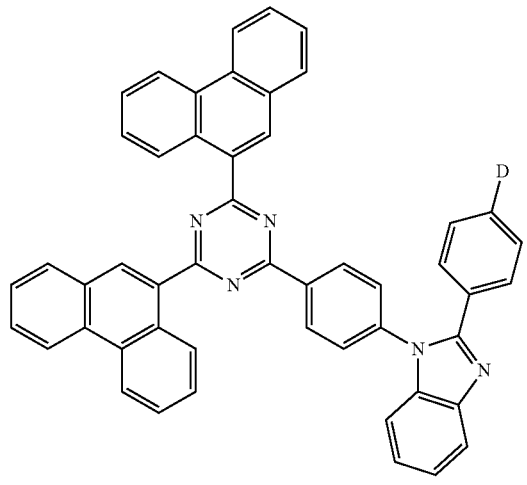
[Chemical Formula A46]
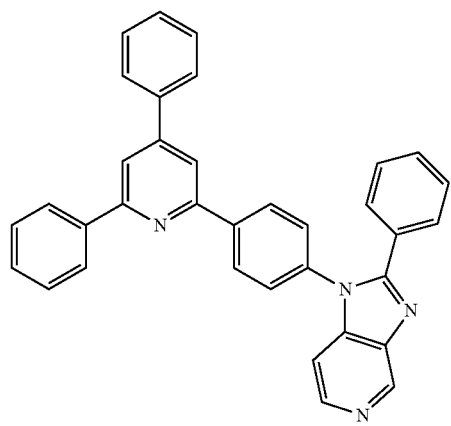
[Chemical Formula A47]
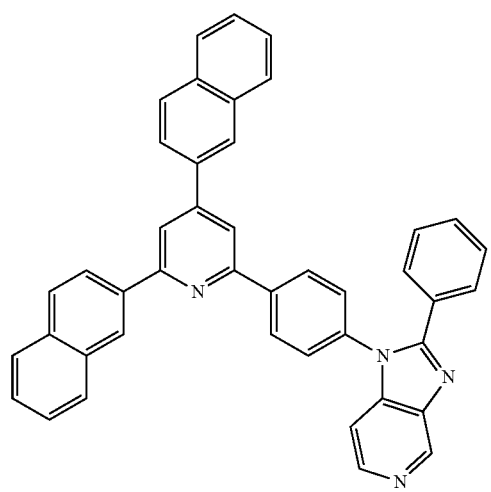
[Chemical Formula A48]
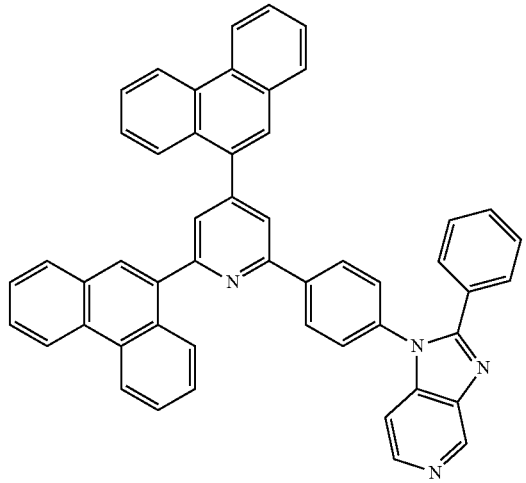
[Chemical Formula A49]
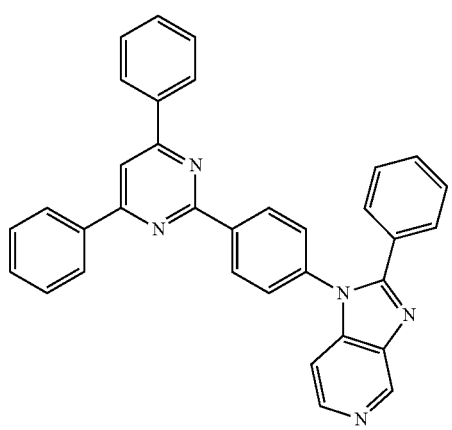
[Chemical Formula A50]
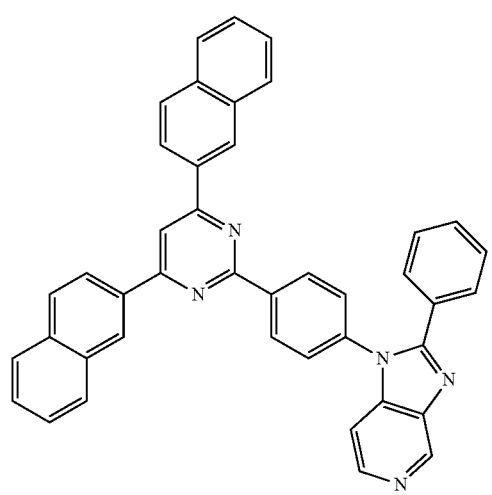

[Chemical Formula A51]
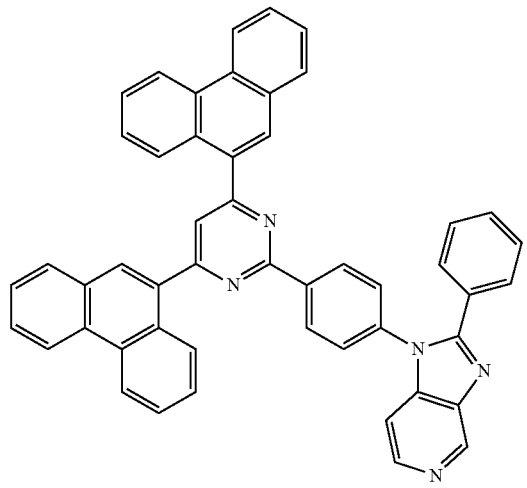
[Chemical Formula A52]
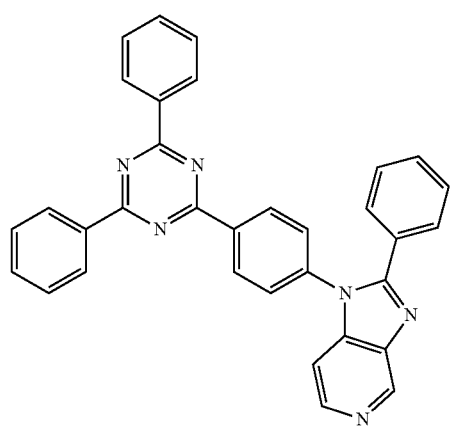
[Chemical Formula A53]
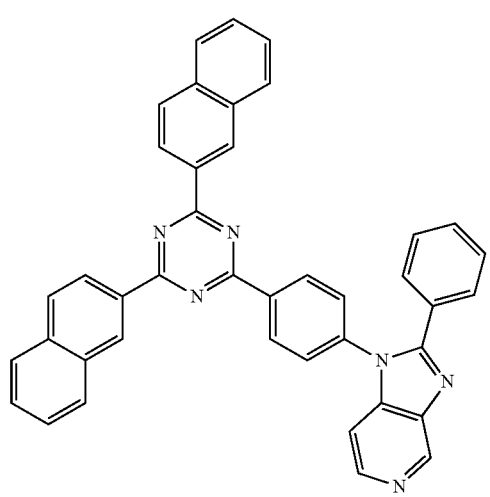
[Chemical Formula A54]
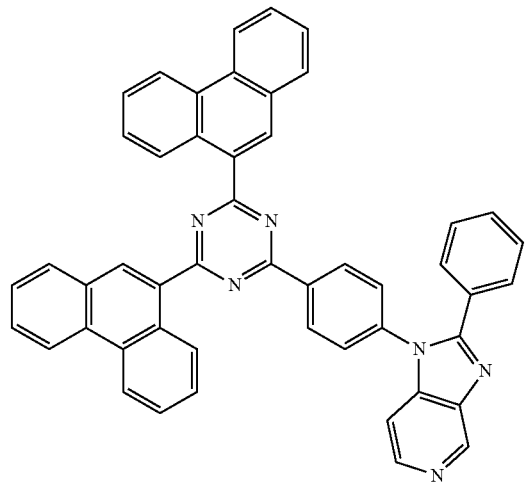
[Chemical Formula A55]
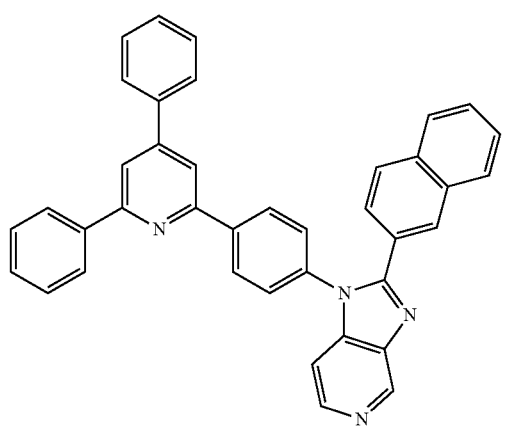
[Chemical Formula A56]
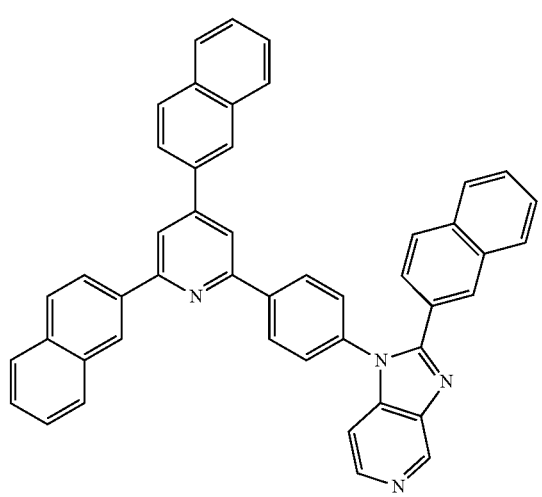

[Chemical Formula A57]
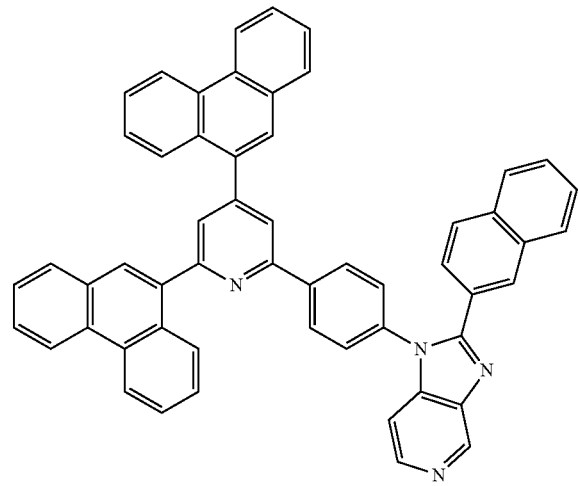
[Chemical Formula A58]
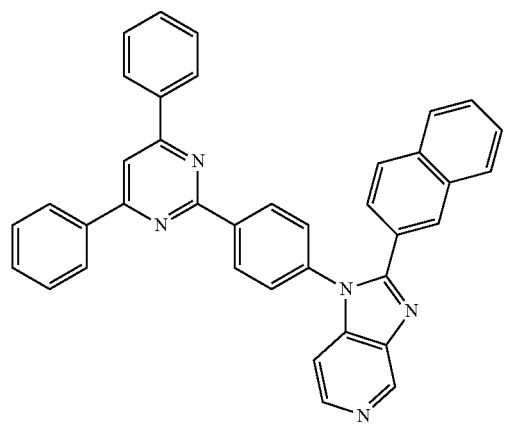
[Chemical Formula A59]
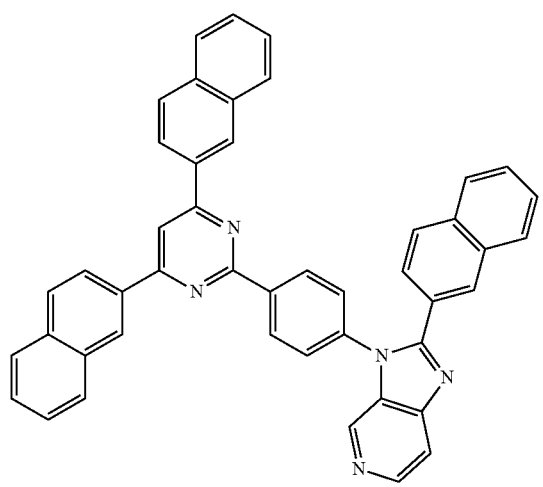
[Chemical Formula A60]
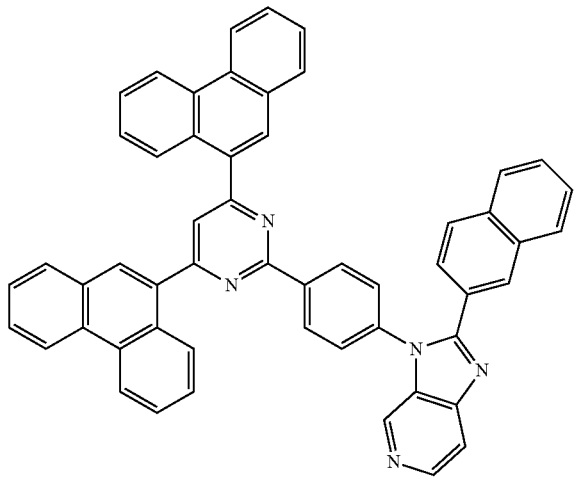
[Chemical Formula A61]
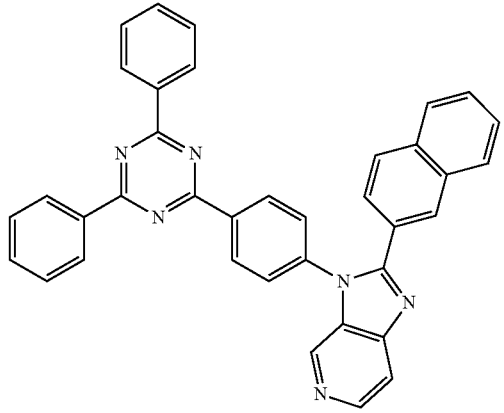
[Chemical Formula A62]
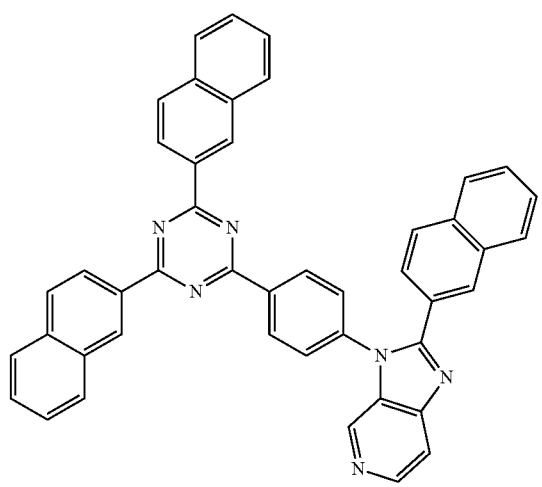

[Chemical Formula A63]
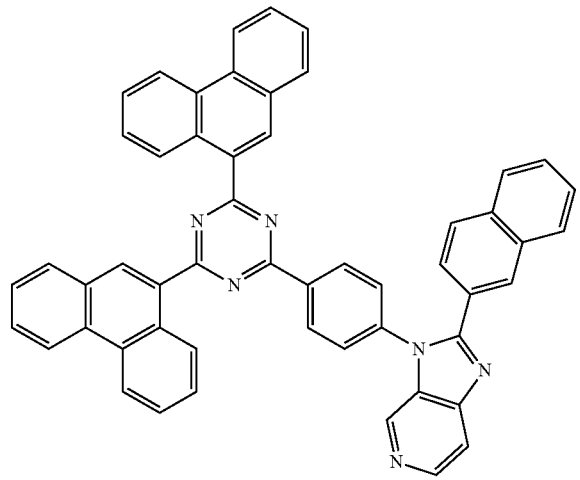
[Chemical Formula A64]
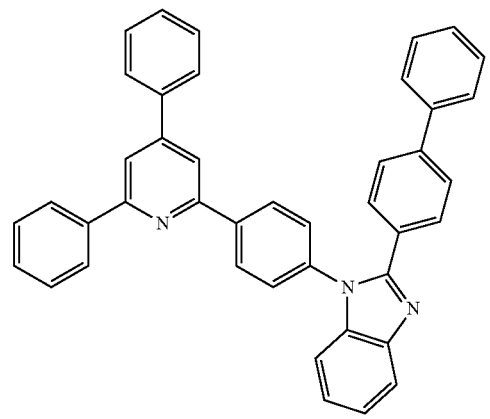
[Chemical Formula A65]
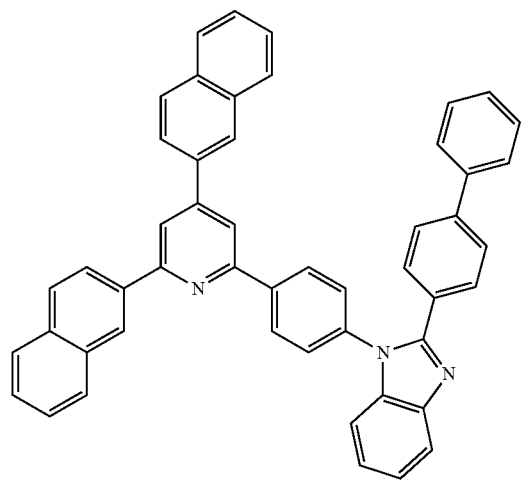
[Chemical Formula A66]
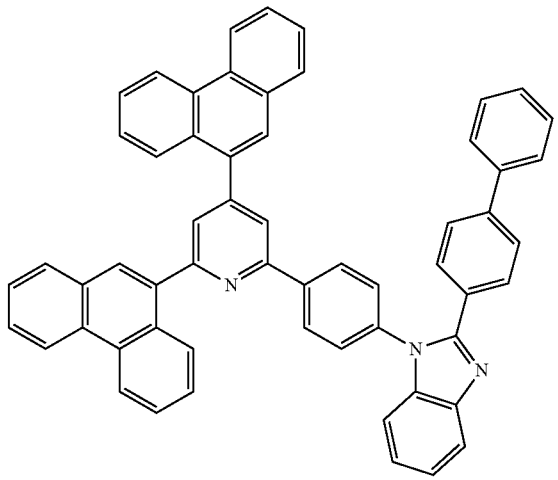
[Chemical Formula A67]
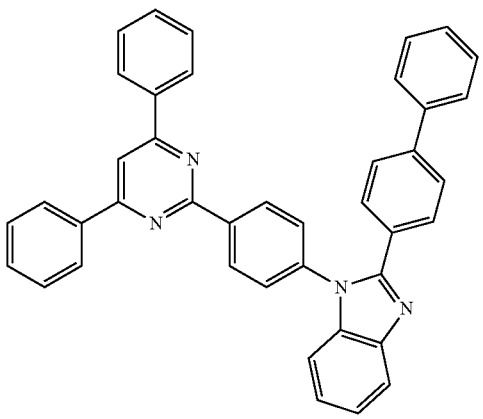
[Chemical Formula A68]
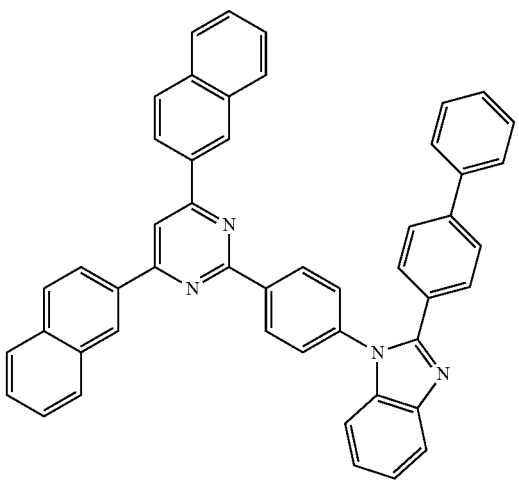

[Chemical Formula A69]
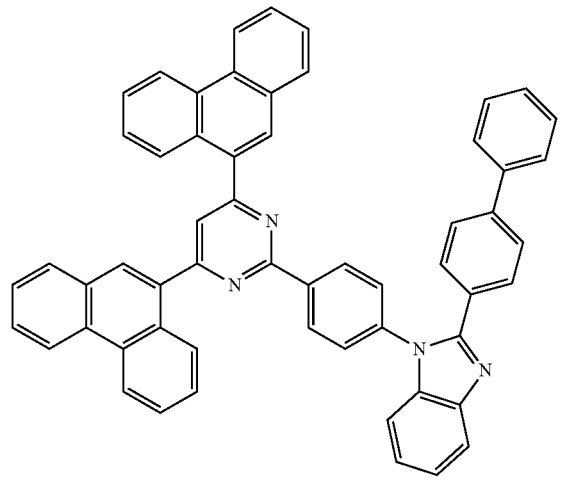
[Chemical Formula A70]
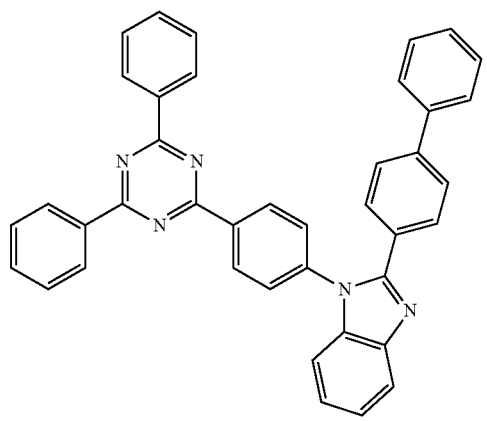
[Chemical Formula A71]
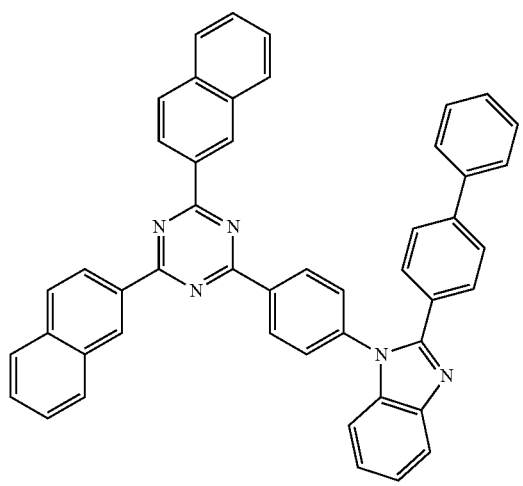
[Chemical Formula A72]
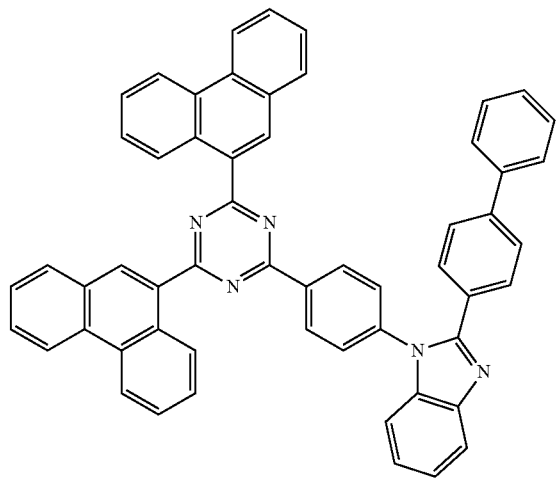
[Chemical Formula A73]
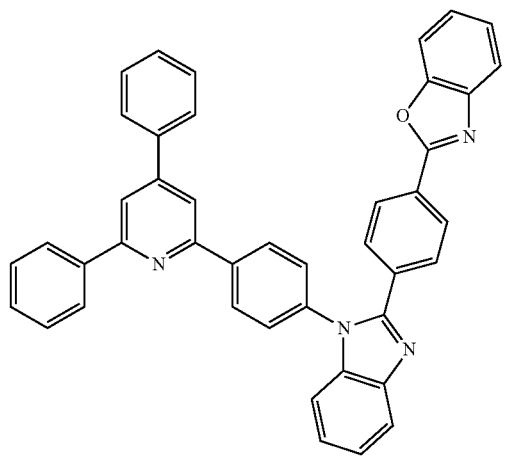
[Chemical Formula A74]
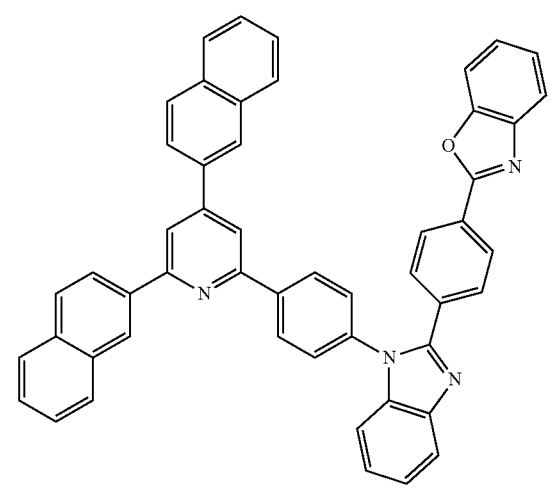

[Chemical Formula A75]
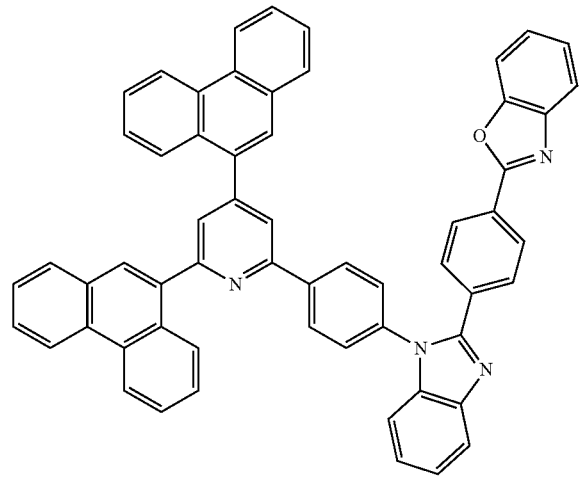
[Chemical Formula A76]
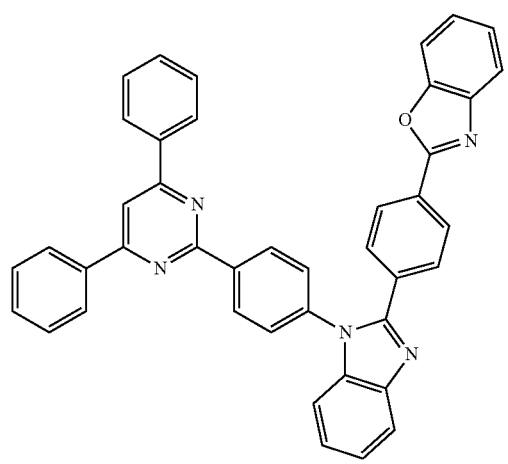
[Chemical Formula A77]
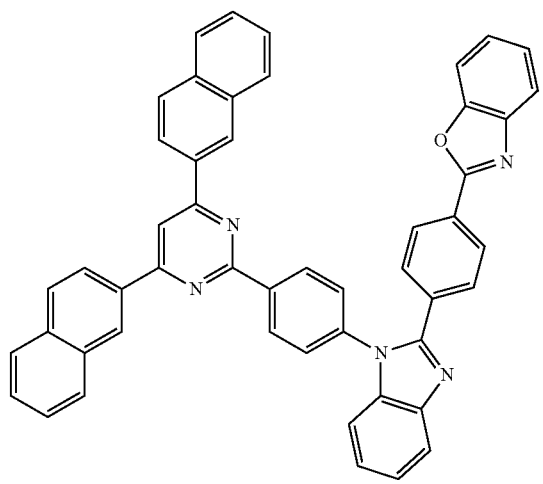
[Chemical Formula A78]
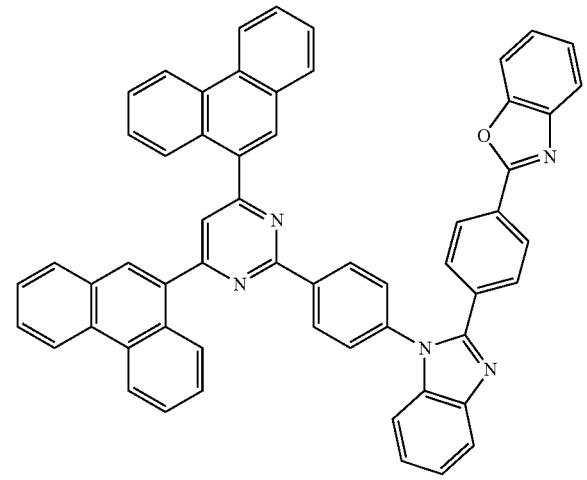
[Chemical Formula A79]
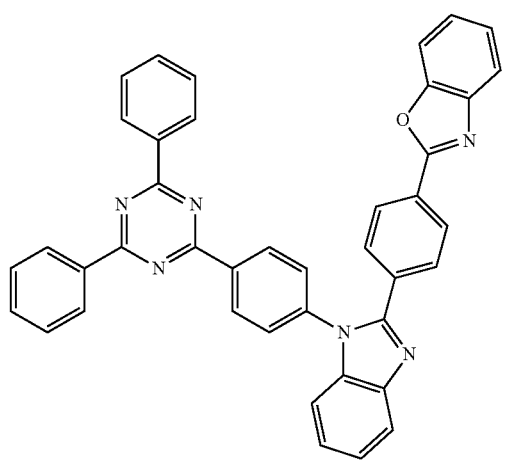
[Chemical Formula A80]
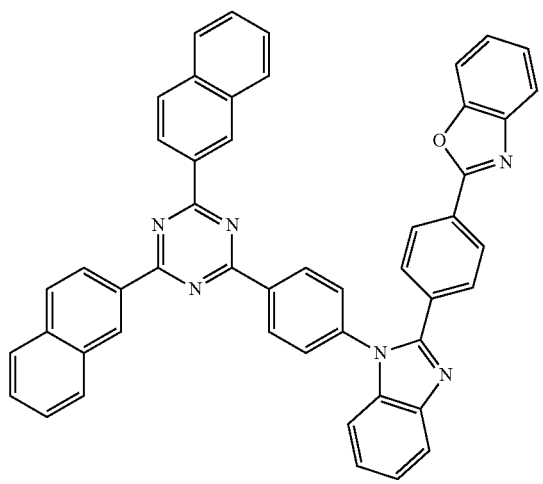

[Chemical Formula A81]
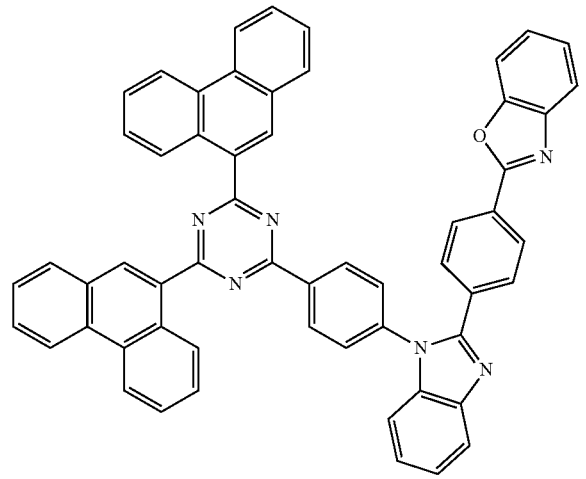
[Chemical Formula A82]
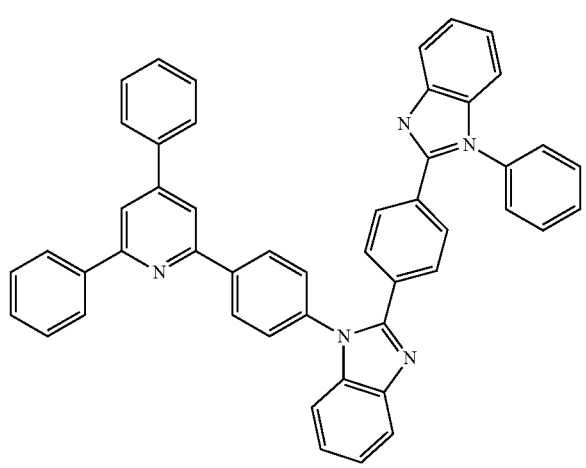
[Chemical Formula A83]
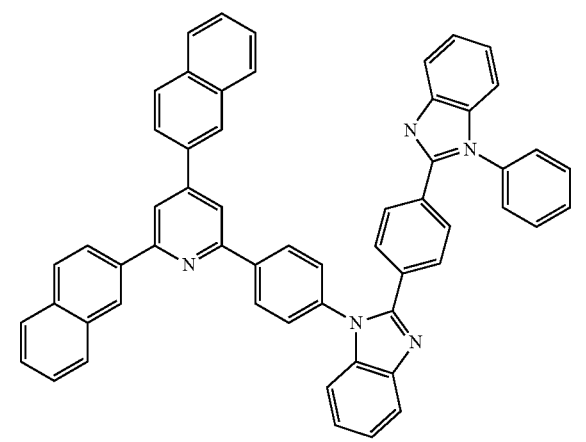
[Chemical Formula A84]
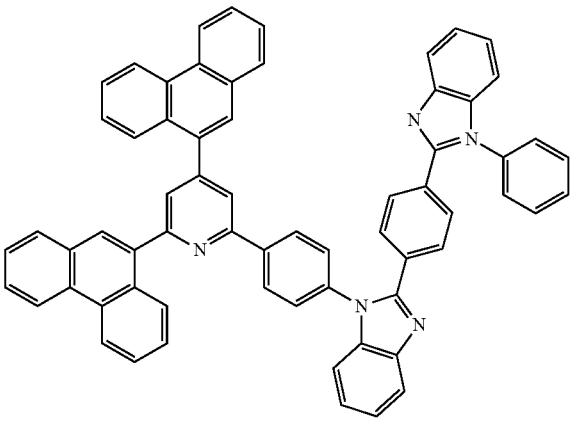
[Chemical Formula A85]
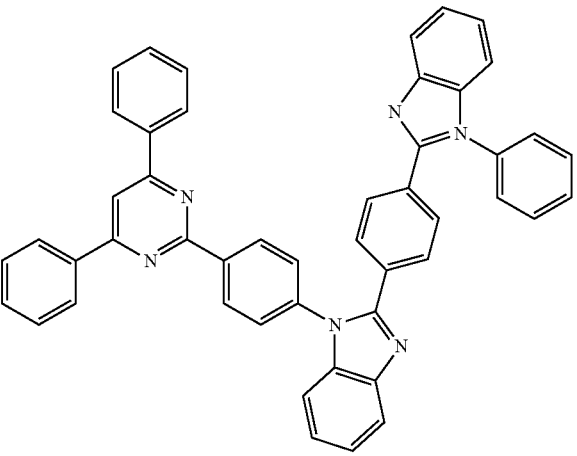
[Chemical Formula A86]
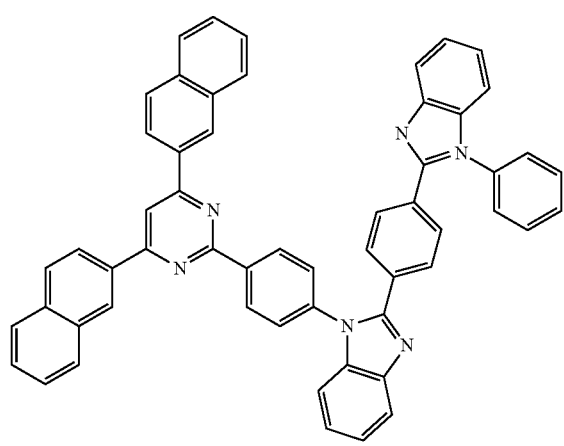

[Chemcial Formula A87]
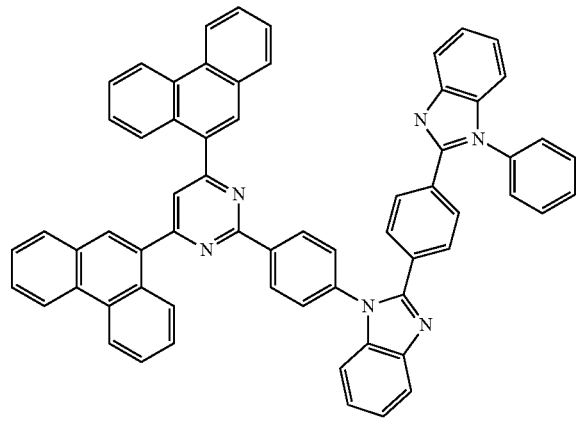
[Chemical Formula A88]
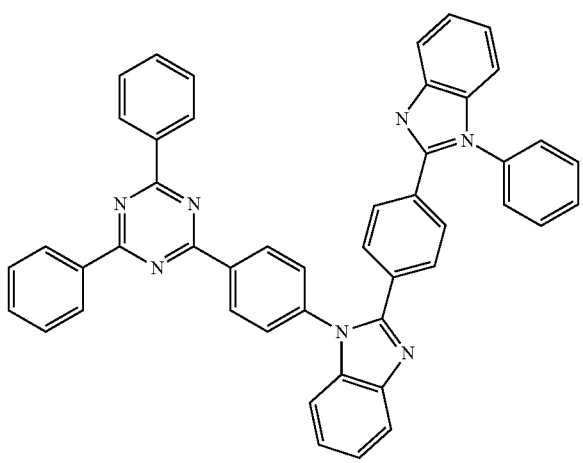
[Chemical Formula A89]
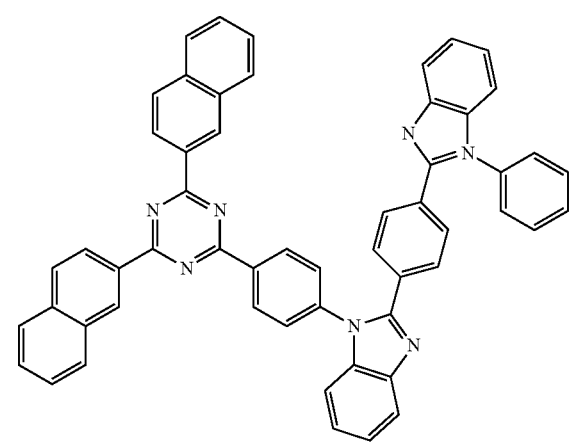
[Chemcial Formula A90]
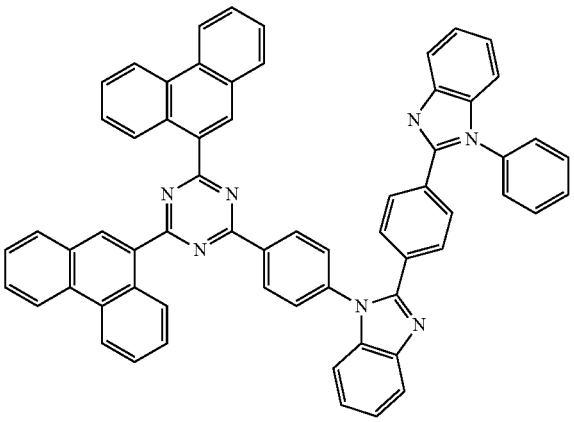
[Chemical Formula A91]
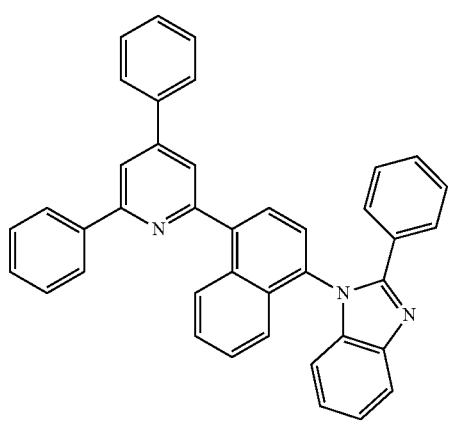
[Chemical Formula A92]
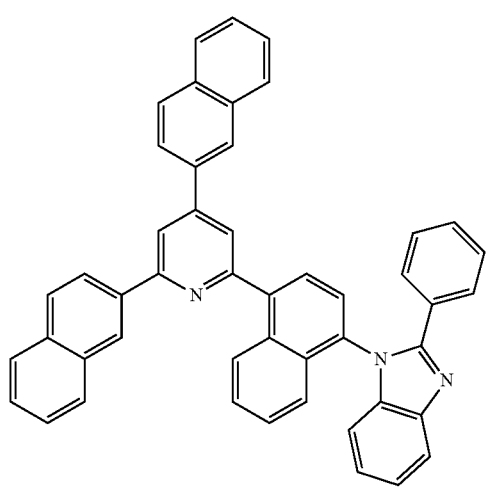

[Chemical Formula A93]
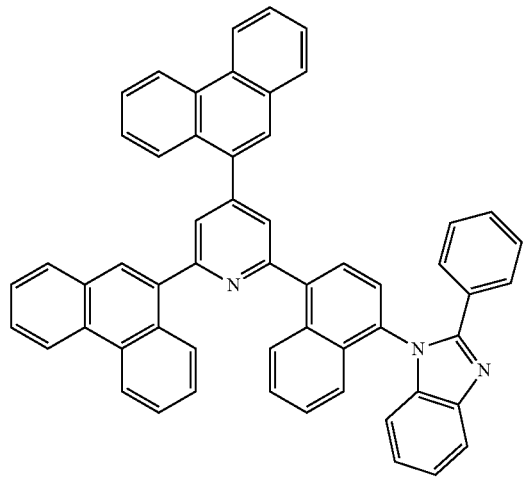
[Chemical Formula A94]
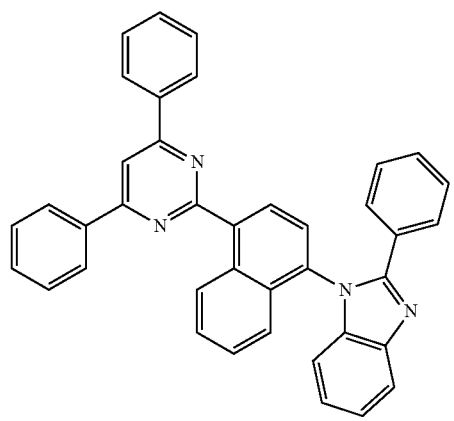
[Chemical Formula A95]
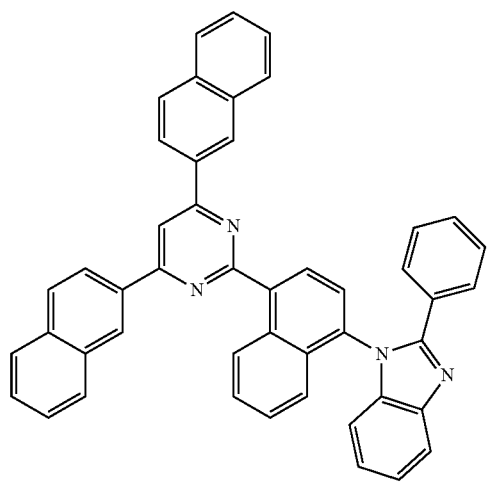
[Chemical Formula A96]
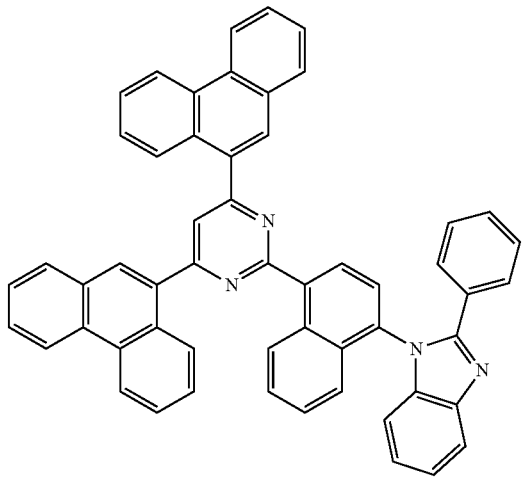
[Chemical Formula A97]
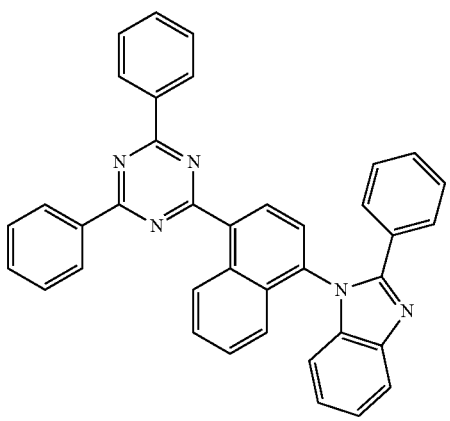
[Chemical Formula A98]
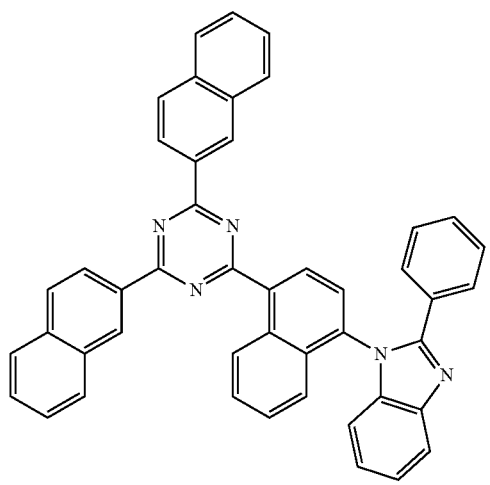

[Chemical Formula A99]

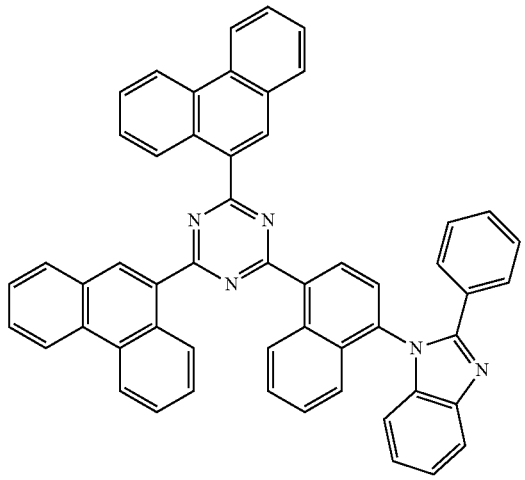

The compound for an organic optoelectronic device including the above compounds may have a glass transition temperature of greater than or equal to about 110° C. and a thermal decomposition temperature of greater than or equal to about 400° C., indicating improved thermal stability. Thereby, it is possible to produce an organic optoelectronic device having a high efficiency.

The compound for an organic optoelectronic device including the above compounds may play a role for emitting light or injecting and/or transporting electrons, and also may act as a light emitting host with an appropriate dopant. In other words, the compound for an organic optoelectronic device may be used as a phosphorescent or fluorescent host material, a blue light emitting dopant material, or an electron transport material.

The compound for an organic optoelectronic device according to an embodiment may be used for an organic thin layer, and it may improve the life-span characteristic, efficiency characteristic, electrochemical stability, and thermal stability of an organic optoelectronic device and decrease the driving voltage.

Therefore, according to an embodiment, an organic optoelectronic device that includes the compound for an organic optoelectronic device is provided. The organic optoelectronic device may be an organic photoelectric device, an organic light emitting diode, an organic solar cell, an organic transistor, an organic photo conductor drum, an organic memory device, and the like. For example, the compound for an organic optoelectronic device according to an embodiment may be included in an electrode or an electrode buffer layer in the organic solar cell to improve the quantum efficiency, and it may be used as an electrode material for a gate, a source-drain electrode, or the like in the organic transistor.

Hereinafter, an organic light emitting diode is described in greater detail.

According to an embodiment, an organic light emitting diode includes an anode, a cathode, and at least one or more organic thin layer between the anode and the cathode, the at least one of the organic thin layer may include the compound for an organic optoelectronic device.

The organic thin layer that may include the compound for an organic optoelectronic device may include a layer selected from the group of an emission layer, a hole transport layer (HTL), a hole injection layer (HIL), an electron transport layer (ETL), an electron injection layer (EIL), a hole blocking layer, and a combination thereof. The at least one organic thin layer may include the compound for an organic optoelectronic device according to an embodiment. Particularly, the compound for an organic optoelectronic device according to an embodiment may be included in an electron transport layer (ETL) or an electron injection layer (EIL). In addition, when the compound for an organic optoelectronic device is included in the emission layer, the compound for an organic optoelectronic device may be included as a phosphorescent or fluorescent host, or as a fluorescent blue dopant material.

FIGS. 1 to 5 illustrate cross-sectional views of organic light emitting diodes including the compound for an organic optoelectronic device according to an embodiment.

Referring to FIGS. 1 to 5, organic light emitting diodes 100, 200, 300, 400, and 500 according to an embodiment include at least one organic thin layer 105 interposed between an anode 120 and a cathode 110.

The anode 120 may include an anode material having a large work function to help hole injection into an organic thin layer. The anode material may include: a metal such as nickel, platinum, vanadium, chromium, copper, zinc, and gold, or alloys thereof; a metal oxide such as zinc oxide, indium oxide, indium tin oxide (ITO), and indium zinc oxide (IZO); a combined metal and oxide such as ZnO:Al or SnO$_2$:Sb; or a conductive polymer such as poly(3-methylthiophene), poly[3,4-(ethylene-1,2-dioxy)thiophene] (PEDT), polypyrrole, and polyaniline, but is not limited thereto. For example, a transparent electrode including indium tin oxide (ITO) may be used as an anode.

The cathode 110 may include a cathode material having a small work function to help electron injection into an organic thin layer. The cathode material may include: a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, LiO$_2$/Al, LiF/Ca, LiF/Al, and BaF$_2$/Ca, but is not limited thereto. For example, a metal electrode including aluminum may be used as a cathode.

Referring to FIG. 1, the organic light emitting diode 100 may include an organic thin layer 105 including only an emission layer 130.

Figure 2:
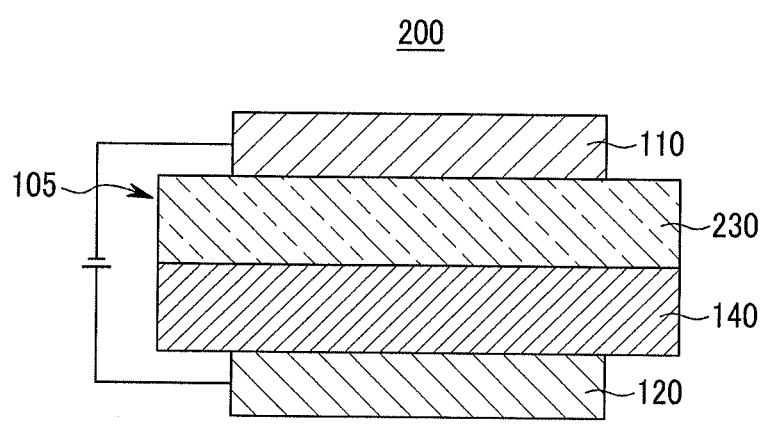

Referring to FIG. 2, a double-layered organic light emitting diode 200 may include an organic thin layer 105 including an emission layer 230 including an electron transport layer (ETL), and a hole transport layer (HTL) 140. As shown in FIG. 2, the organic thin layer 105 may include a double layer of the emission layer 230 and hole transport layer (HTL) 140. The emission layer 130 may also function as an electron transport layer (ETL), and the hole transport layer (HTL) 140 layer may have an excellent binding property with a transparent electrode such as ITO and/or an excellent hole transport capability.

Figure 3:
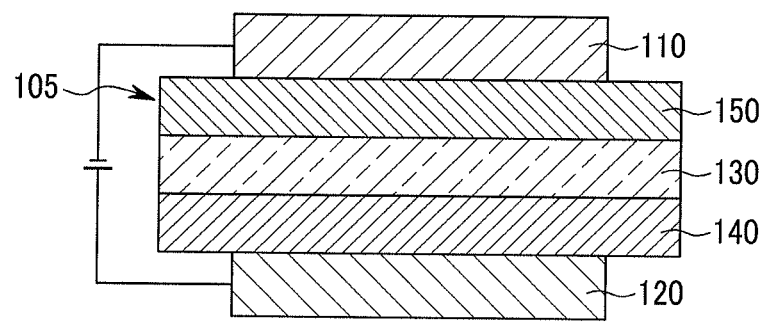

Referring to FIG. 3, a three-layered organic light emitting diode 300 may include an organic thin layer 105 including an electron transport layer (ETL) 150, an emission layer 130, and a hole transport layer (HTL) 140. The emission layer 130 may be independently installed, and layers having an excellent electron transport capability or an excellent hole transport capability may be separately stacked.

Figure 4:
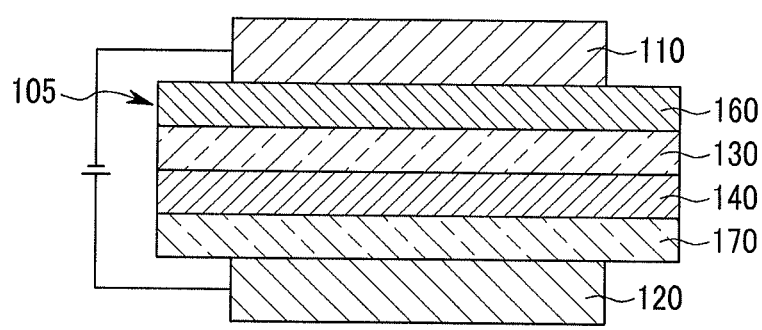

As shown in FIG. 4, a four-layered organic light emitting diode 400 may include an organic thin layer 105 including an electron injection layer (EIL) 160, an emission layer 130, a hole transport layer (HTL) 140, and a hole injection layer (HIL) 170 for adherence with the anode of ITO.

Figure 5:
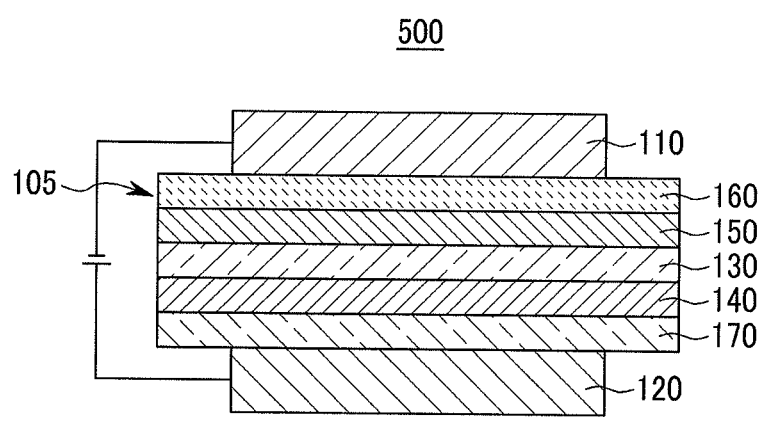

As shown in FIG. 5, a five layered organic light emitting diode 500 may include an organic thin layer 105 including an electron transport layer (ETL) 150, an emission layer 130, a hole transport layer (HTL) 140, and a hole injection layer (HIL) 170, and further including an electron injection layer (EIL) 160 to achieve a low voltage.

In FIGS. 1 to 5, the organic thin layer 105 including at least one selected from the group of an electron transport layer (ETL) 150, an electron injection layer (EIL) 160, emission layers 130 and 230, a hole transport layer (HTL) 140, a hole injection layer (HIL) 170, and combinations thereof may include a compound for an organic optoelectronic device. The compound for an organic optoelectronic device may be used for an electron transport layer (ETL) 150 including the electron transport layer (ETL) 150 or electron injection layer (EIL) 160. When it is used for the electron transport layer (ETL), it is possible to provide an organic light emitting diode having a more simple structure because it does not require an additional hole blocking layer (not shown), though a hole blocking layer may still be used.

Furthermore, when the compound for an organic optoelectronic device is included in the emission layers 130 and 230, the material for the organic optoelectronic device may be included as a phosphorescent or fluorescent host or a fluorescent blue dopant.

The organic light emitting diode may be fabricated by, e.g.: forming an anode on a substrate; forming an organic thin layer in accordance with a dry coating method such as evaporation, sputtering, plasma plating, and ion plating or a wet coating method such as spin coating, dipping, and flow coating; and providing a cathode thereon.

Another embodiment provides a display device including the organic light emitting diode according to the above embodiment.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Preparation of Compound for Organic Optoelectronic Device

Example 1

Synthesis of compound represented by Chemical Formula A6

The compound represented by Chemical Formula A6, as a specific example of compound for an organic optoelectronic device according to an embodiment, was synthesized through 6 steps as shown in the following Reaction Scheme 1:

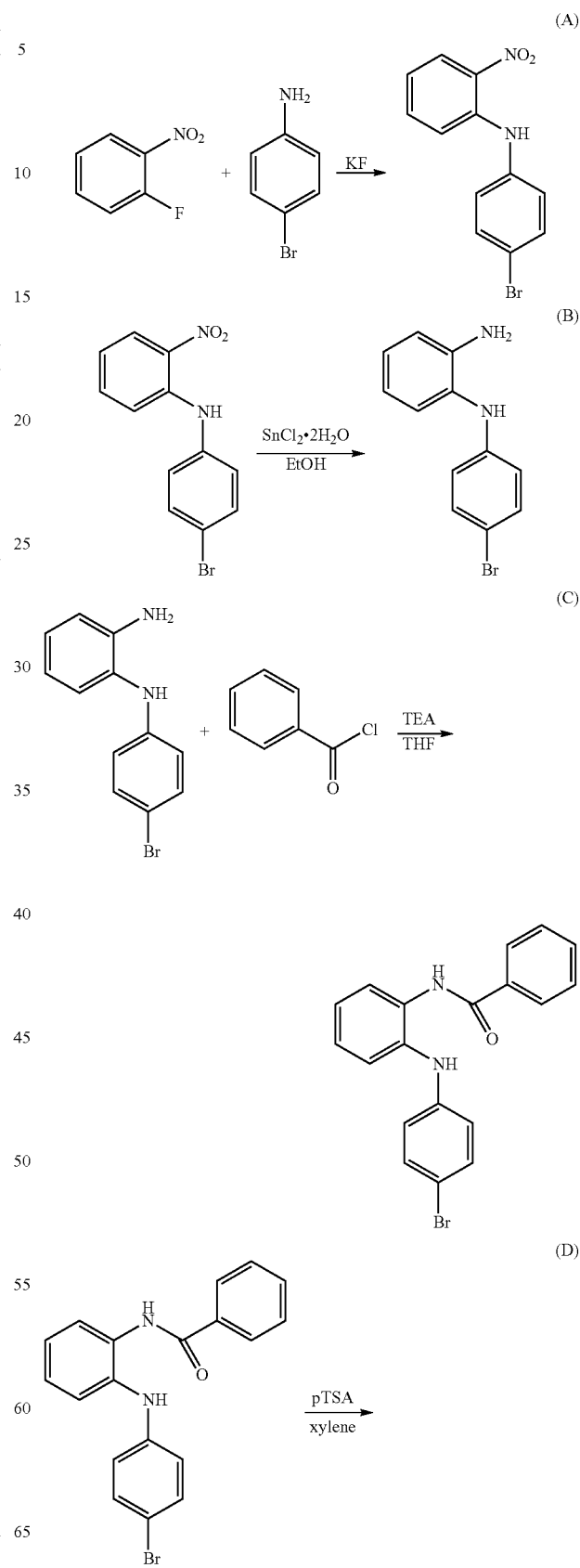

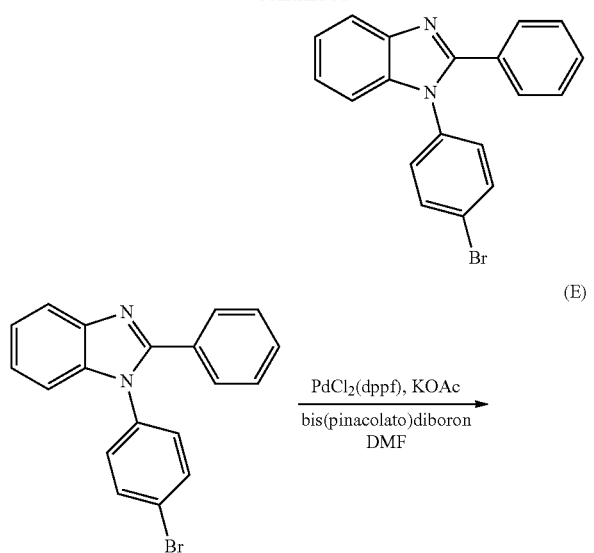
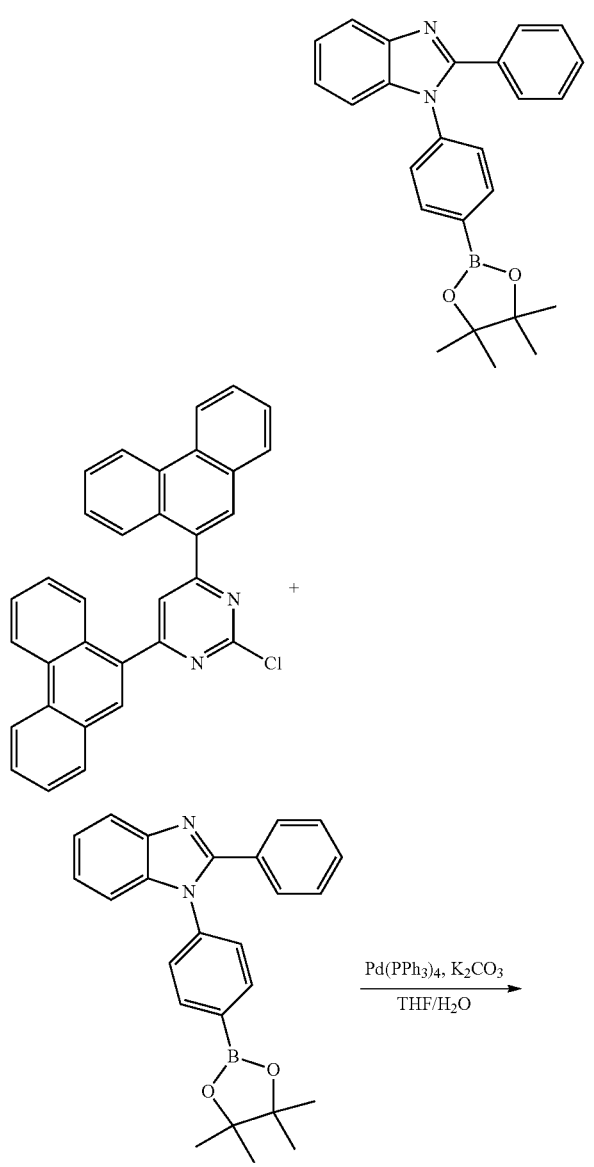

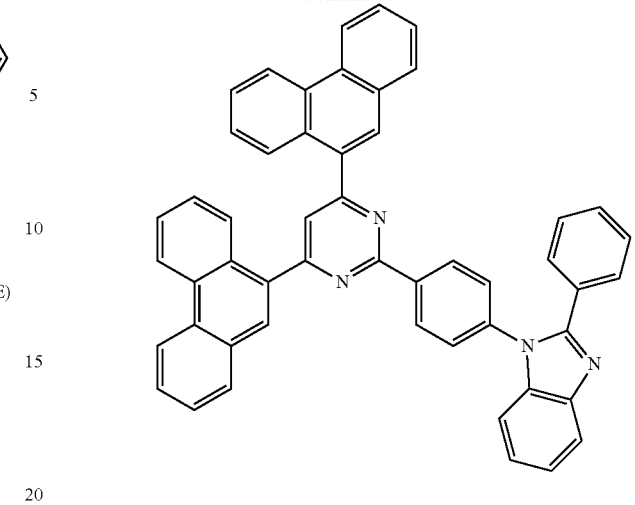

(E)

First Step: Synthesis of Intermediate Product (A)

14.1 g (100.0 mmol) of 2-fluoronitrobenzene, 34.4 g (200.0 mmol) of 4-bromoaniline, and 7.3 g (125.0 mmol) of potassium fluoride were agitated at 180° C. for 72 hours. The mixed solid was extracted with chloroform and recrystallized with methanol to provide 26.1 g (yield: 89%) of an intermediate product (A).

Second Step: Synthesis of Intermediate Product (B)

26.1 g (89.0 mmol) of the intermediate product (A) and 100.5 g (445.0 mmol) of tin chloride dihydrate were suspended in 500 mL of ethanol, and heated and refluxed at 80° C. for 12 hours. After cooling, ethanol was removed under reduced pressure distillation, and the deposited solid was poured in distilled water and neutralized with a sodium hydrogen carbonate aqueous solution. The mixed solution was extracted with ethyl acetate and filtered with silica gel, and then the solvent was removed to provide 22 g (yield: 94%) of an intermediate product (B).

Third Step: Synthesis of Intermediate Product (C)

22 g (83.6 mmol) of the intermediate product (B) and 23.3 mL (167.2 mmol) of triethylamine were suspended in 250 mL of tetrahydrofuran and agitated, and 9.7 mL (83.9 mmol) of benzoyl chloride was slowly added in a dropwise fashion thereto and agitated at 0° C. for 30 minutes. The reaction solution was poured in distilled water to deposit a solid, which was filtered and separated. The filtered solid was recrystallized with methanol to provide 29.7 g (yield: 96%) of the intermediate product (C).

Fourth Step: Synthesis of Intermediate Product (D)

29.7 g (80.9 mmol) of the intermediate product (C) and 1.4 g (8.1 mmol) of p-toluenesulfonic acid were suspended in 300 mL of xylene and agitated at 150° C. for 12 hours. After cooling, xylene was removed under the reduced pressure to provide a solid, and the solid was recrystallized with methanol to provide 22.4 g (yield: 79%) of the intermediate product (D).

Fifth Step: Synthesis of Intermediate Product (E)

22.4 g (64.1 mmol) of the intermediate product (D), 19.6 g (77.0 mmol) of bis(pinacolato)diboron, 1.3 g (1.6 mmol) of [1,1'-bis(diphenylphosphino)ferrocene]dichloropalladium (II), and 18.9 g (192.3 mmol) of potassium acetate were suspended in 230 mL of dimethylformamide and agitated at 80° C. for 12 hours. After cooling, the reaction solution was poured in distilled water to deposit a solid, which was filtered and separated. The filtered solid was recrystallized with ethyl acetate/hexane to provide 24.4 g (yield: 96%) of intermediate product (E).

Sixth Step: Synthesis of Compound represented by Chemical Formula A6

22 g (47.1 mmol) of 2-chloro-4-(phenanthren-10-yl)-6-(phenanthren-9-yl)pyrimidine, 24.3 g (61.2 mmol) of the intermediate product (E), 1.4 g (1.2 mmol) of tetrakis (triphenylphosphine)palladium, and 13 g (94.2 mmol) of potassium carbonate were suspended in a mixed solvent of 440 mL of tetrahydrofuran and 220 mL of water and agitated at 80° C. for 12 hours. After cooling, the reaction fluid was separated into two layers, and then an organic layer was cleaned with a saturated sodium chloride aqueous solution and dried with anhydrous sodium sulfate. The organic solvent was removed by distillation under a reduced pressure, and the residues were recrystallized with methanol/dichloromethane to provide 26 g (yield: 78%) of a compound. (element analysis/Calcd: C, 87.40; H, 4.60; N, 7.99. Found: C, 87.46; H, 4.57; N, 7.96).

Manufacture of Organic Light Emitting Diode

Example 2

An organic light emitting diode was fabricated using 1,000 Å-thick ITO as an anode and 1,000 Å-thick aluminum (Al) as a cathode.

In particular, the anode was prepared cutting an ITO glass substrate having a sheet resistance of 15 Ω/cm² into a size of 50 mm×50 mm×0.7 mm and cleaning it in acetone, isopropyl alcohol, and pure water, respectively for 5 minutes and with UV ozone for 30 minutes.

Then, N1,N1'-(biphenyl-4,4'-diyl)bis(N1-(naphthalen-2-yl)-N4,N4-diphenylbenzene-1,4-diamine) was deposited to be 65 nm thick as a hole injection layer (HIL) on the glass substrate, and N,N'-di(1-naphthyl)-N,N-diphenylbenzidine was deposited to be 40 nm thick as a hole transport layer (HTL).

Then, 4% of N,N,N',N'-tetrakis(3,4-dimethylphenyl) chrysene-6,12-diamine and 96% of 9-(3-(naphthalen-1-yl) phenyl)-10-(naphthalen-2-yl)anthracene were deposited to be 25 nm thick as an emission layer on the hole transport layer (HTL).

Then, the compound according to Example 1 was deposited to be 30 nm thick on the emission layer as an electron transport layer (ETL).

On the electron transport layer (ETL), Liq was vacuum-deposited to be 0.5 nm thick on the electron injection layer (EIL), and Al was vacuum-deposited to be 100 nm thick, forming a Liq/Al electrode.

Example 3

An organic light emitting diode was fabricated in accordance with the same procedure as in Example 2, except that the electron transport layer (ETL) was fabricated by depositing the compound obtained in Example 1 and Liq at 1:1.

Comparative Example 1

An organic light emitting diode was fabricated in accordance with the same procedure as in Example 2, except that the electron transport layer (ETL) was fabricated by using the compound represented by the following Chemical Formula R¹ instead of the compound represented by Chemical Formula 1 obtained from Example 1.

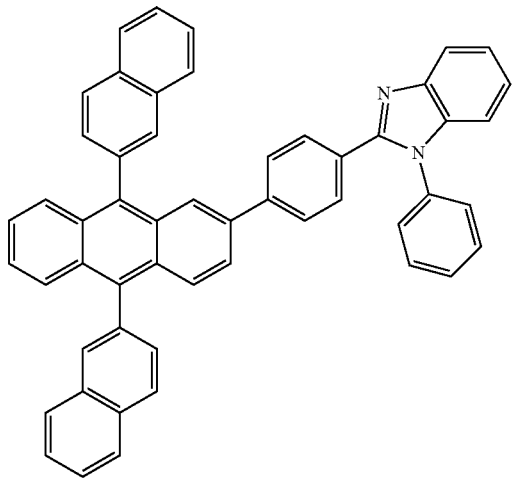

[Chemical Formula R1]

Comparative Example 2

An organic light emitting diode was fabricated in accordance with the same procedure as in Comparative Example 1, except that the electron transport layer (ETL) was fabricated by depositing the compound represented by Chemical Formula R¹ obtained from Comparative Example 1 and Liq at 1:1.

Performance Measurement of Organic Light Emitting Diode

Experimental Examples

Each of the obtained organic light emitting diodes according to Examples 2 and 3, and Comparative Examples 1 and 2 were measured for luminance change, current density change depending upon the voltage, and luminous efficiency. The specific method was as follows. The results are shown in the following Table 1 and FIGS. 6 to 13

(1) Measurement of Current Density Change Depending on Voltage Change

The obtained organic light emitting diode was measured for current value flowing in the unit device while increasing the voltage from 0V to 10V using a current-voltage meter (Keithley 2400), and the measured current value was divided by area to provide the result.

(2) Measurement of Luminance Change Depending on Voltage Change

The organic light emitting diode was measured for luminance using a luminance meter (Minolta Cs-1000A) while increasing the voltage from 0V to 10V.

(3) Measurement of Luminous Efficiency

Current efficiency (cd/A) and electric power efficiency (lm/W) at the same luminance (1,000 cd/m²) were calculated by using luminance and current density from (1) and (2) and voltage.

Figure 6:
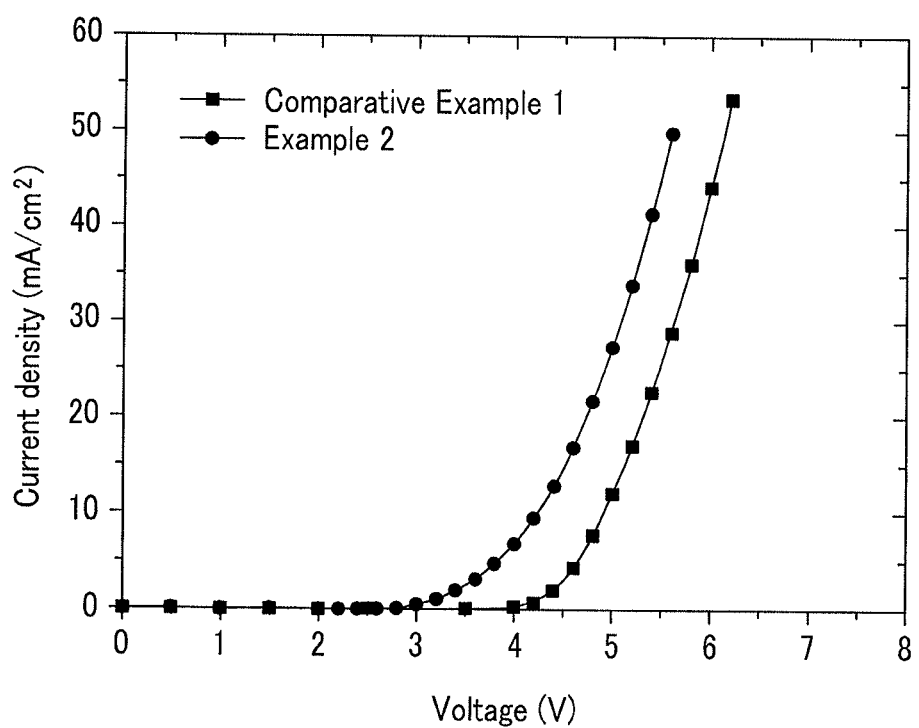
FIG. 6 illustrates changes in current density depending on a voltage of the devices according to Example 2 and Comparative Example 1.

FIG. 6 illustrates data showing the current density change depending upon the voltage of devices obtained from Example 2 and Comparative Example 1.

Figure 7:
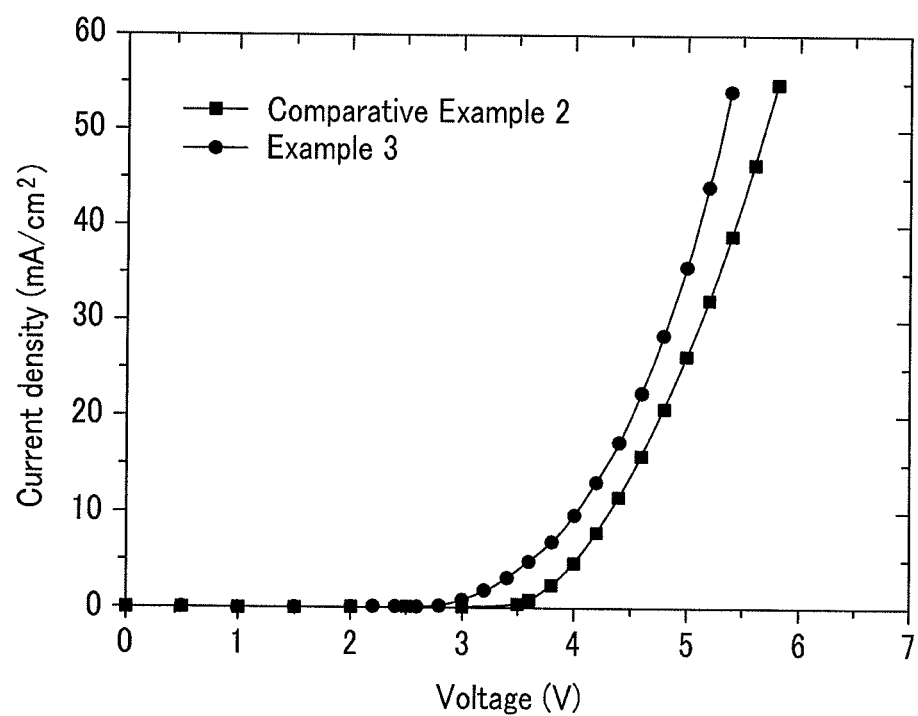
FIG. 7 illustrates changes in current density depending on a voltage of the devices according to Example 3 and Comparative Example 2.

FIG. 7 illustrates data showing the current density change depending upon the voltage of devices obtained from Example 3 and Comparative Example 2.

Figure 8:
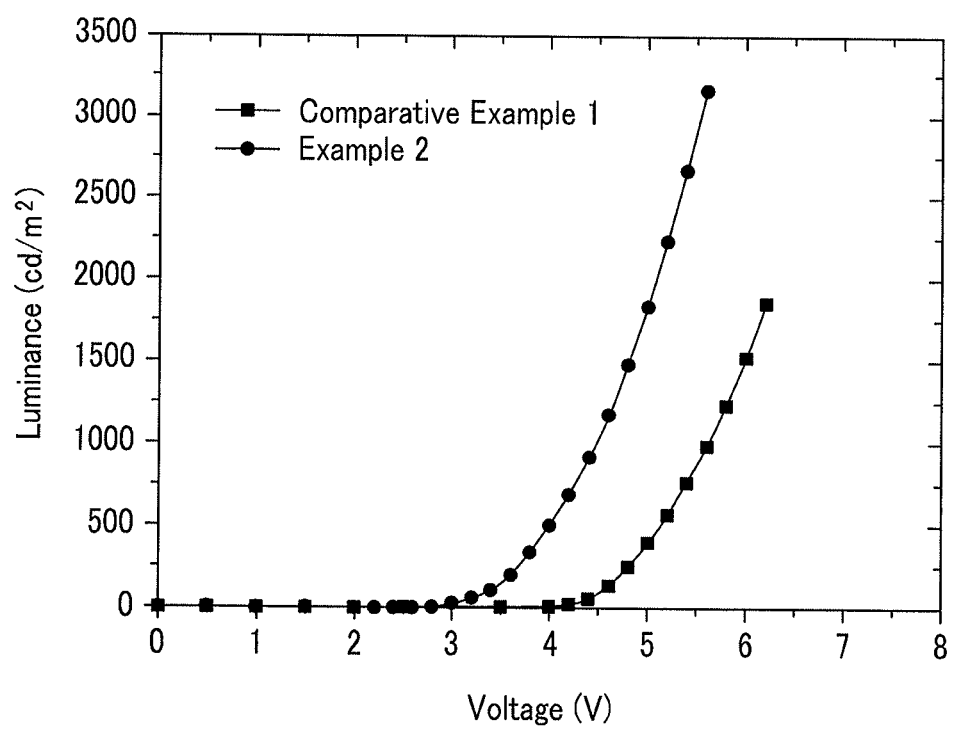
FIG. 8 illustrates changes in luminance depending on a voltage of the devices according to Example 2 and Comparative Example 1.

FIG. 8 illustrates data showing the luminance change depending upon the voltage of devices obtained from Example 2 and Comparative Example 1.

Figure 9:
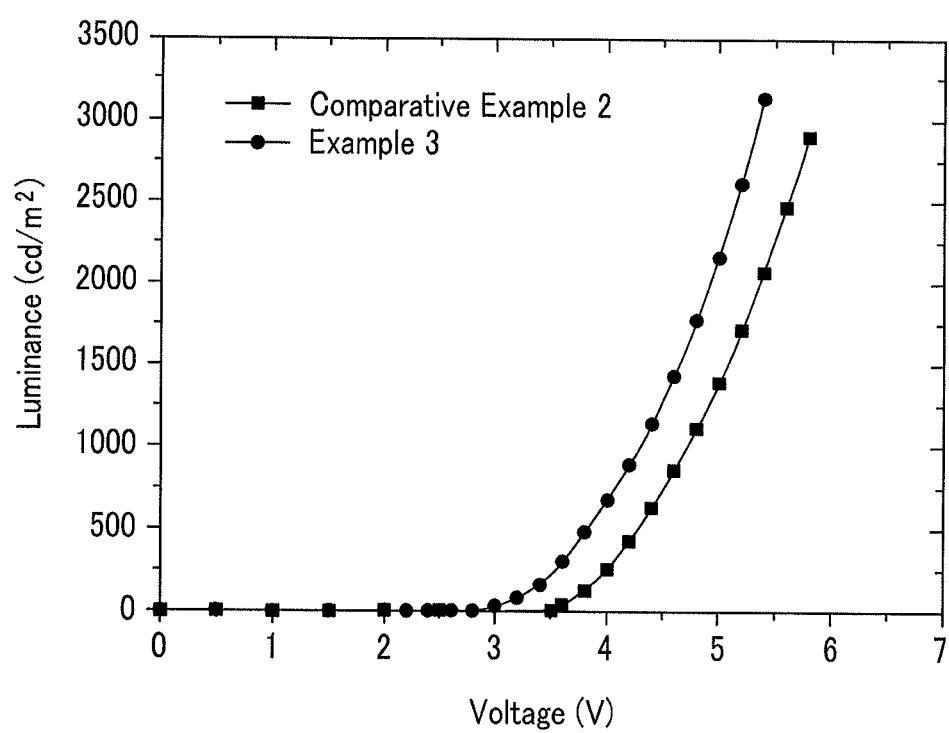
FIG. 9 illustrates changes in luminance depending on a voltage of the devices according to Example 3 and Comparative Example 2.

FIG. 9 illustrates data showing the luminance change depending upon the voltage of devices obtained from Example 3 and Comparative Example 2.

Figure 10:
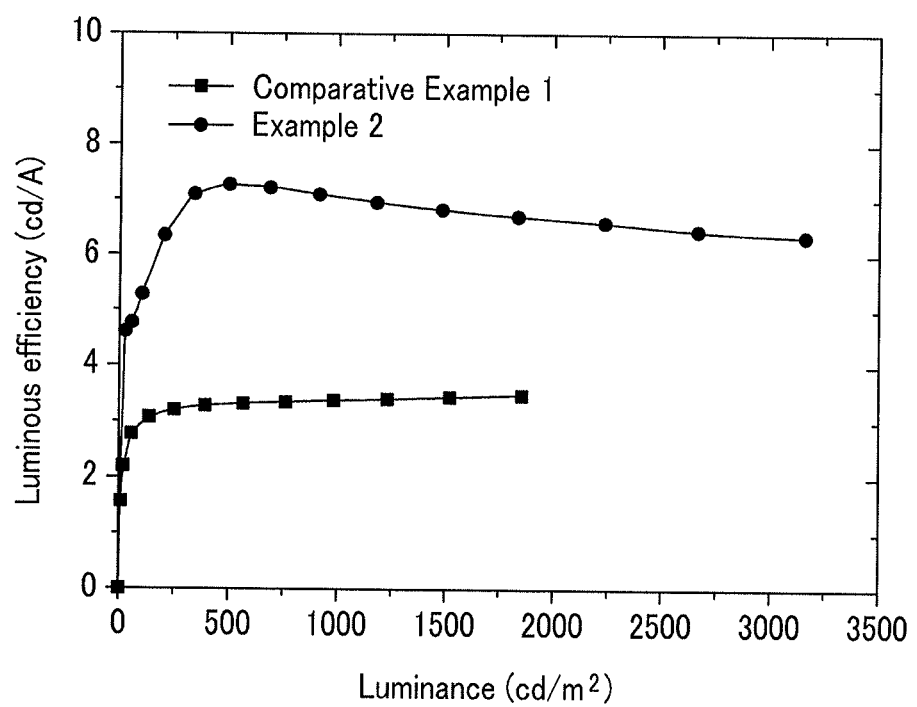
FIG. 10 illustrates changes in luminous efficiency depending on the luminance of devices according to Example 2 and Comparative Example 1.

FIG. 10 illustrates a data showing the luminous efficiency change depending upon the luminance of devices obtained from Example 2 and Comparative Example 1.

Figure 11:
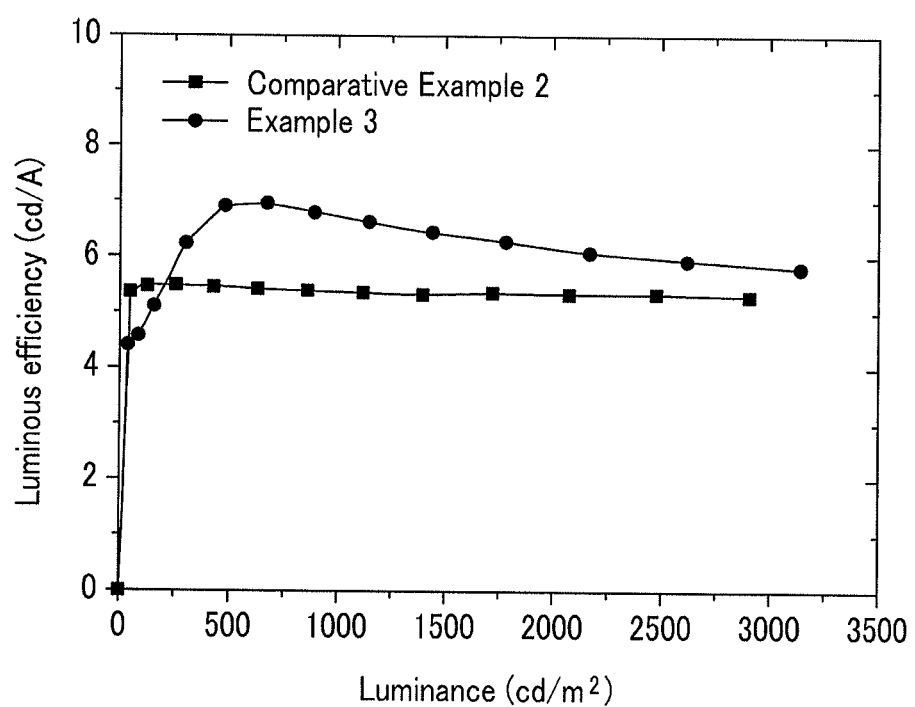
FIG. 11 illustrates changes in luminous efficiency depending on the luminance of devices according to Example 3 and Comparative Example 2.

FIG. 11 illustrates data showing the luminous efficiency change depending upon the luminance of devices obtained from Example 3 and Comparative Example 2.

Figure 12:
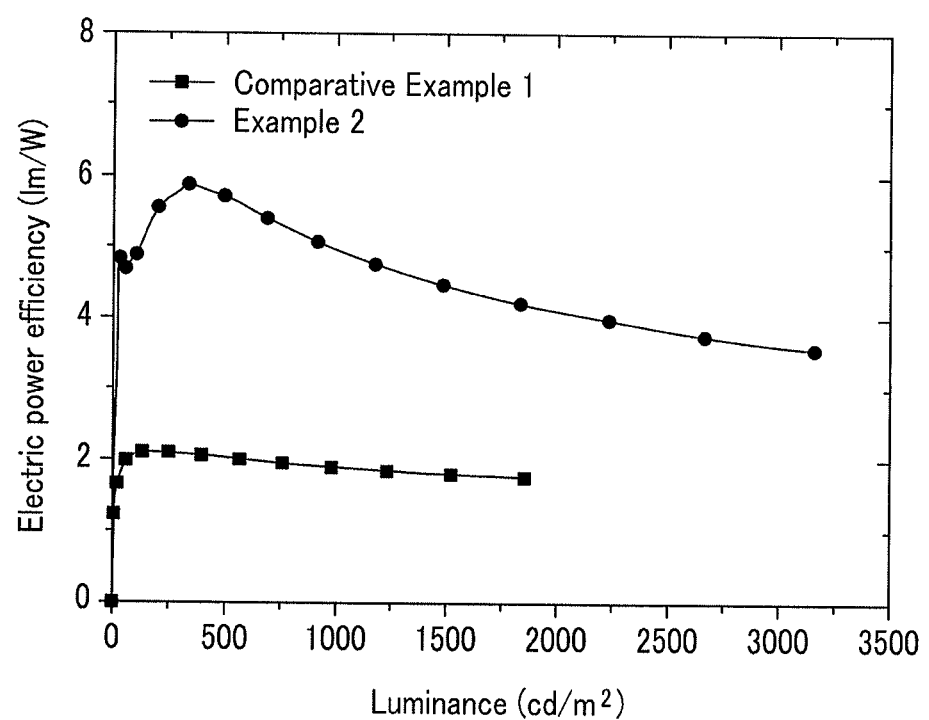
FIG. 12 illustrates changes in electric power efficiency depending on the luminance of devices according to Example 2 and Comparative Example 1.

FIG. 12 illustrates data showing the electric power efficiency change depending upon the luminance of devices obtained from Example 2 and Comparative Example 1.

Figure 13:
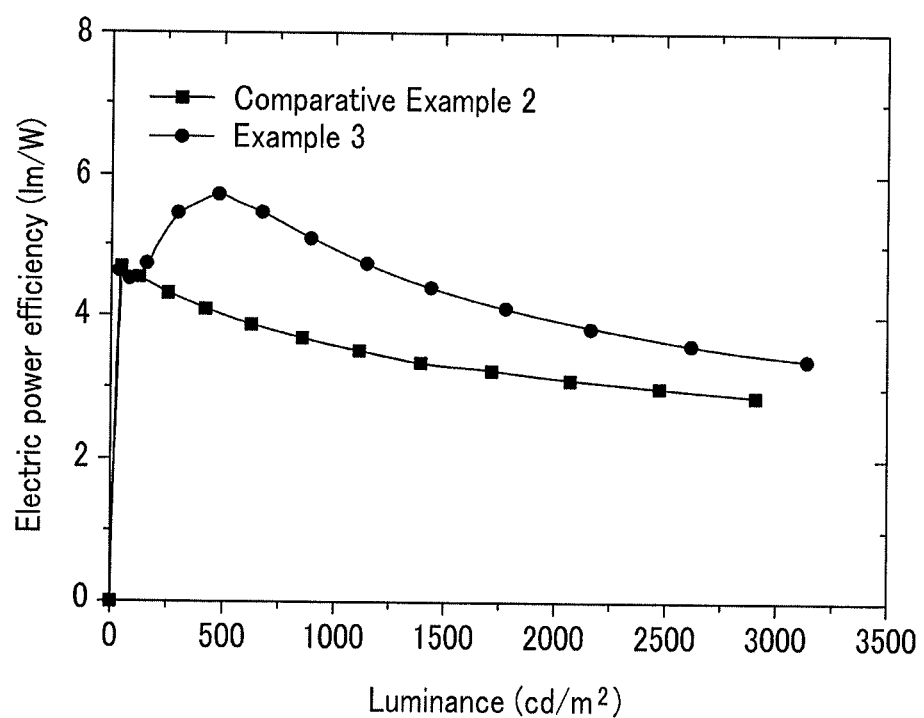
FIG. 13 illustrates changes in electric power efficiency depending on the luminance of devices according to Example 3 and Comparative Example 2.

FIG. 13 illustrates data showing the electric power efficiency change depending upon the luminance of devices obtained from Example 3 and Comparative Example 2.

TABLE 1

|  | Luminance 500 cd/m$^2$ | | | | |
| --- | --- | --- | --- | --- | --- |
|  | Driving voltage (V) | Luminous efficiency (cd/A) | Electric power efficiency (lm/W) | CIE x | y |
| Example 2 | 4.0 | 7.3 | 5.7 | 0.14 | 0.05 |
| Example 3 | 3.8 | 6.9 | 5.7 | 0.14 | 0.05 |
| Comparative Example 1 | 5.2 | 3.3 | 2.0 | 0.14 | 0.05 |
| Comparative Example 2 | 4.4 | 5.4 | 3.9 | 0.14 | 0.06 |

As shown in Table 1, it is understood that the organic light emitting diode according to Example 2 had excellent luminous efficiency and electric power efficiency under low driving voltage, compared to that of Comparative Example 1.

It is also confirmed that the organic light emitting diode according to Example 3 had excellent luminous efficiency and electric power efficiency under low driving voltage, compared to that of Comparative Example 2.

By way of summary and review, organic optoelectronic device may include, e.g., an organic light emitting diode, an organic solar cell, an organic photo conductor drum, and an organic transistor, and the like, which may require a hole injecting or transport material, an electron injecting or transport material, and/or a light emitting material. Particularly, an organic light emitting diode (OLED) has recently drawn attention due to an increasing demand for a flat panel display. In general, organic light emission refers to conversion of electrical energy into photo-energy.

Such an organic light emitting diode may convert electrical energy into light by applying current to an organic light emitting material. It may have a structure in which a functional organic material layer is interposed between an anode and a cathode. The organic material layer includes a multi-layer including different materials, for example a hole injection layer (HIL), a hole transport layer (HTL), an emission layer, an electron transport layer (ETL), and an electron injection layer (EIL), in order to improve efficiency and stability of an organic light emitting diode.

In such an organic light emitting diode, when a voltage is applied between an anode and a cathode, holes from the anode and electrons from the cathode may be injected to an organic material layer and recombined to generate excitons having high energy. The generated excitons may generate light having certain wavelengths while shifting to a ground state.

A phosphorescent light emitting material may be used for a light emitting material of an organic light emitting diode in addition to the fluorescent light emitting material. Such a phosphorescent material may emit light by transporting the electrons from a ground state to an exited state, non-radiance transiting of a singlet exciton to a triplet exciton through intersystem crossing, and transiting a triplet exciton to a ground state to emit light.

As described above, in an organic light emitting diode, an organic material layer may include a light emitting material and a charge transport material, for example a hole injection material, a hole transport material, an electron transport material, an electron injection material, and the like. The light emitting material may be classified as blue, green, and red light emitting materials according to emitted colors, and yellow and orange light emitting materials to emit colors approaching natural colors.

When one material is used as a light emitting material, a maximum light emitting wavelength may be shifted to a long wavelength or color purity may decrease because of interactions between molecules, or device efficiency may decrease because of a light emitting quenching effect. Therefore, a host/dopant system may be included as a light emitting material in order to improve color purity and increase luminous efficiency and stability through energy transfer.

In order to implement excellent performance of an organic light emitting diode, a material constituting an organic material layer, for example a hole injection material, a hole transport material, a light emitting material, an electron transport material, an electron injection material, and a light emitting material such as a host and/or a dopant, should be stable and have good efficiency. Such a material may also be required for other organic optoelectronic devices.

The low molecular organic light emitting diode may be manufactured as a thin film in a vacuum deposition method and may have good efficiency and life-span performance. A polymer organic light emitting diode may be manufactured in an Inkjet or spin coating method and may have an advantage of low initial cost and being large-sized.

Both low molecular organic light emitting diodes and polymer organic light emitting diodes may have an advantage of self-light emitting, high speed response, wide viewing angle, ultra-thin, high image quality, durability, large driving temperature range, and the like. In particular, they may have a good visibility due to self-light emitting characteristic compared with a conventional LCD (liquid crystal display) and may have an advantage of decreasing thickness and weight of LCD up to a third, because they do not need a backlight. In addition, the response speed of a microsecond unit, which may be about 1,000 times faster than LCD, may allow for the realization of an improved motion picture without after-image. Based on these advantages, organic light emitting diodes may have about 80 times efficiency and more than about 100 times life-span.

Displays incorporating organic light emitting diodes may be made relatively large, e.g., as a 40-inch organic light emitting diode panel. It may be beneficial to luminous efficiency and life-span in order for the displays to be larger. Herein, their luminous efficiency needs smooth combination between holes and electrons in an emission layer. However, an organic material may have slower electron mobility than hole mobility, and thus it may have a drawback of inefficient combination between holes and electrons. Accordingly, it may be beneficial to increase electron injection and mobility from a cathode and simultaneously reduce and/or substantially prevent movement of holes.

In order to improve life-span, it may be beneficial to reduce and/or prevent a material crystallization caused by Joule heat generated during device operating. Accordingly, it may be advantageous for an organic compound to have excellent electron injection and mobility, and high electrochemical stability.

The compound for an organic optoelectronic device according to described embodiments may provide advantageous properties. The compound may be used in an organic optoelectronic device, and may allow the organic optoelectronic device to have excellent life-span, efficiency, electrochemical stability, thermal stability, and high luminous efficiency at a low driving voltage. The compound may act as light emitting, or electron injection and/or transport material, and also may act as a light emitting host along with an appropriate dopant, or as a dopant in an appropriate host.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:
1. A compound for an organic optoelectronic device, the compound being represented by Chemical Formula 6:

[Chemical Formula 6]

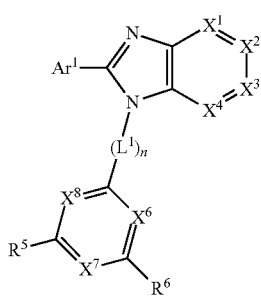

wherein, in Chemical Formula 6,
$X^1$ is —N— or —$CR^1$—,
$X^2$ is —N— or —$CR^2$—,
$X^3$ is —N— or —$CR^3$—,
$X^4$ is —N— or —$CR^4$—,
$R^1$ to $R^4$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, and
$Ar^1$ includes a benzimidazole group or a benzoxazole group, and $L^1$ is a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n is an integer from 0 to 2, and $X^6$ to $X^8$ are each independently —N— or —CR'—, R' is hydrogen or deuterium, at least one of $X^6$ to $X^8$ is —N—, and $R^5$ and $R^6$ are each independently a substituted or unsubstituted phenyl group, a substituted or unsubstituted naphthyl group, a substituted or unsubstituted anthracenyl group, a substituted or unsubstituted phenanthrenyl group, a substituted or unsubstituted triphenylenyl group, a substituted or unsubstituted pyrenyl group, a substituted or unsubstituted chrysenyl group, or a combination thereof.

2. The compound as claimed in claim 1, wherein:

n is an integer from 1 to 2, and $L^1$ is a substituted or unsubstituted ethenylene, a substituted or unsubstituted ethynylene, a substituted or unsubstituted phenylene, a substituted or unsubstituted biphenylene, a substituted or unsubstituted naphthalene, a substituted or unsubstituted pyridinylene, a substituted or unsubstituted pyrimidinylene, or a substituted or unsubstituted triazinylene.

3. The compound as claimed in claim 1, wherein the organic optoelectronic device is selected from the group of an organic photoelectric device, an organic light emitting diode, an organic solar cell, an organic transistor, an organic photo-conductor drum, and an organic memory device.

4. A compound for an organic optoelectronic device, the compound being represented by one of Chemical Formulae A73 to A90:

[Chemical Formula A73]

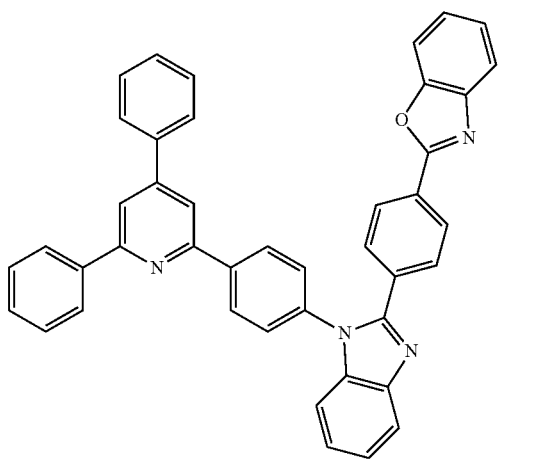

[Chemical Formula A74]
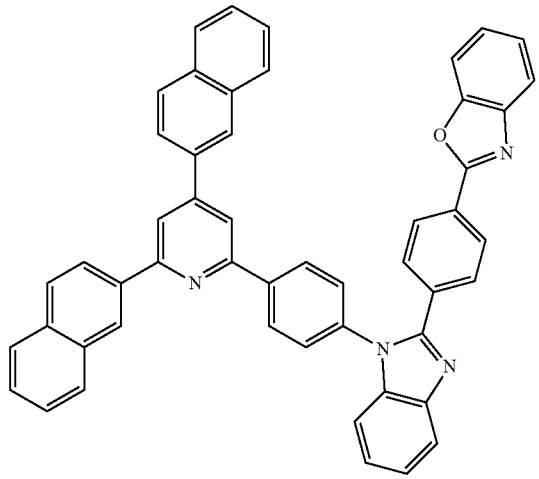
[Chemical Formula A75]
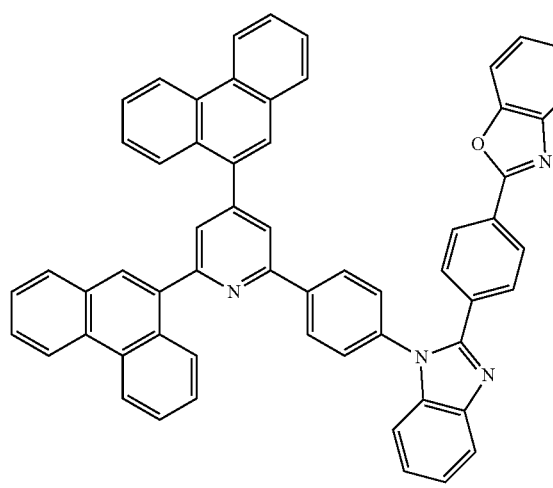
[Chemical Formula A76]
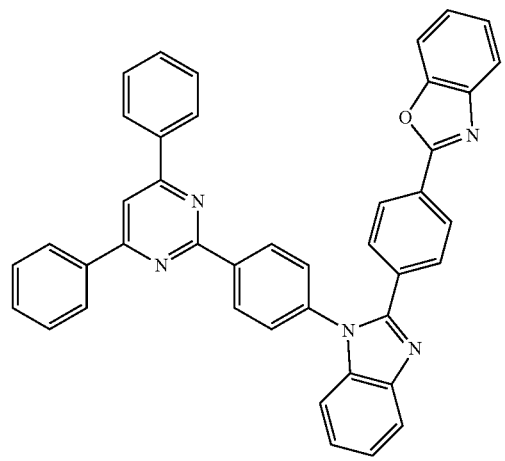
[Chemical Formula A77]
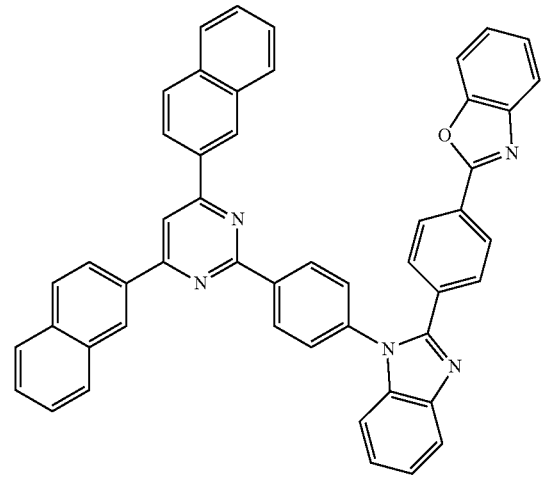
[Chemical Formula A78]
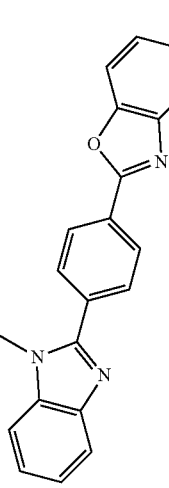
[Chemical Formula A79]
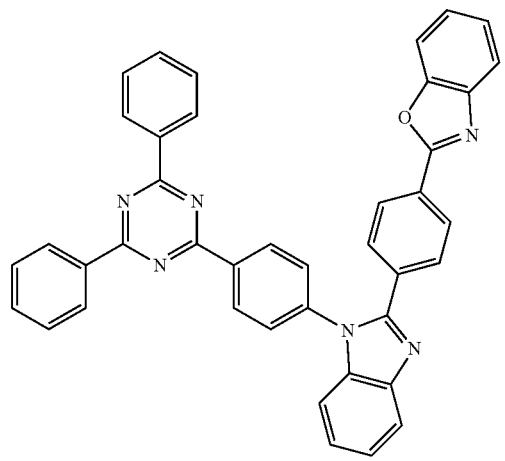

[Chemical Formula A80]
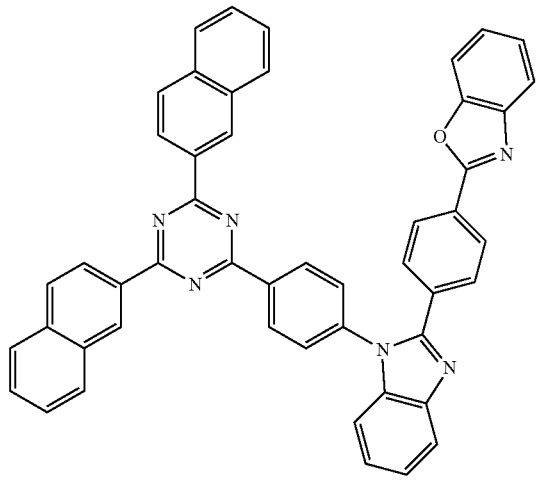
[Chemical Formula A81]
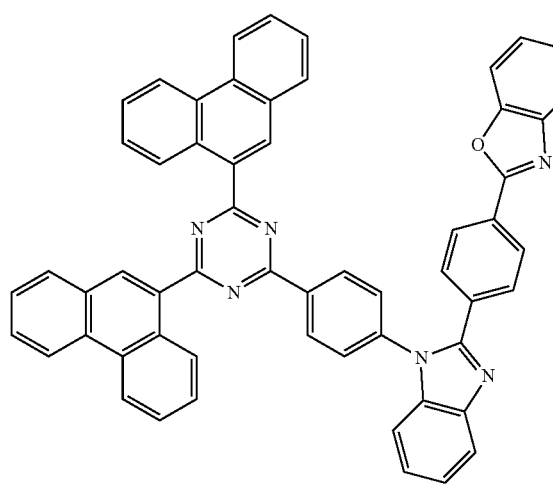
[Chemical Formula A82]
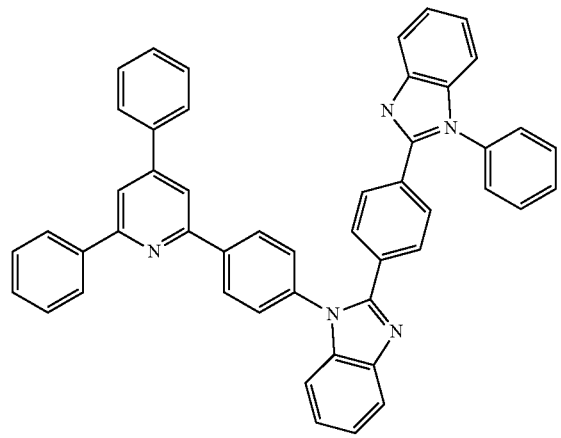
[Chemical Formula A83]
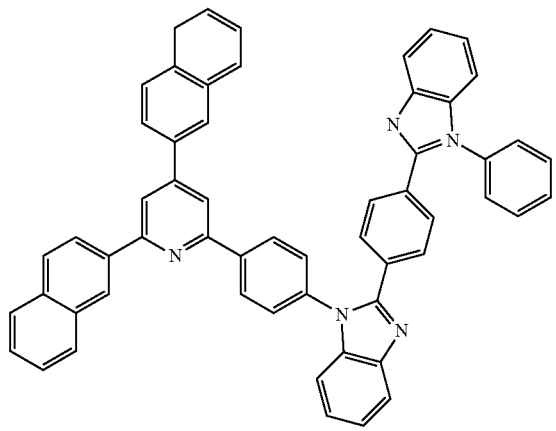
[Chemical Formula A84]
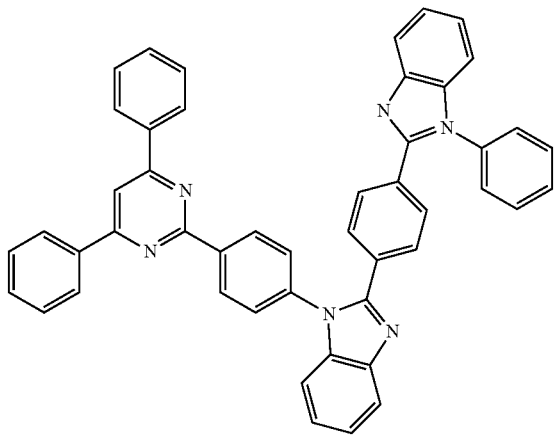
[Chemical Formula A85]

[Chemical Formula A86]

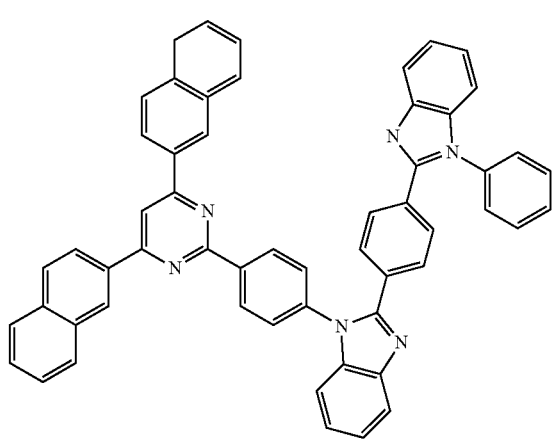

[Chemical Formula A87]

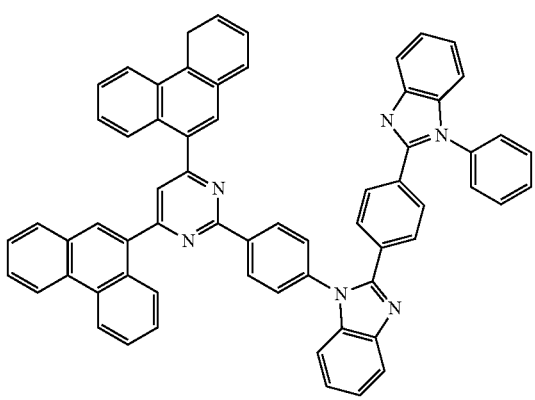

[Chemical Formula A88]

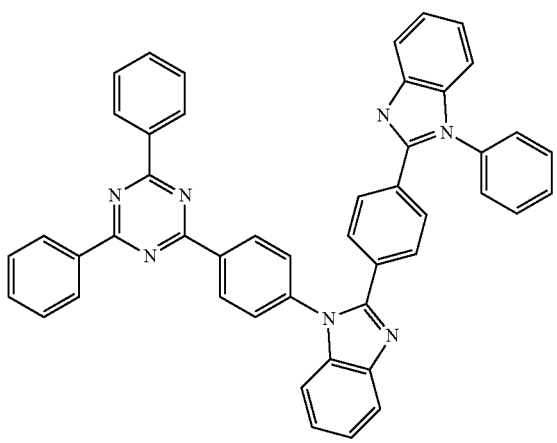

[Chemical Formula A89]

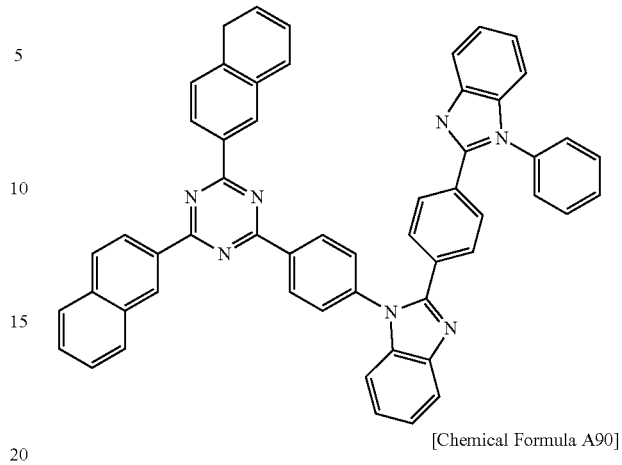

[Chemical Formula A90]

5. An organic light emitting diode, comprising:
an anode, a cathode, and at least one organic thin layer between the anode and cathode,
wherein the at least one organic thin layer includes the compound as claimed in claim 4.

6. The organic light emitting diode as claimed in claim 5, wherein the at least one organic thin layer is selected from the group of an emission layer, a hole transport layer, a hole injection layer, an electron transport layer, an electron injection layer, a hole blocking layer, and a combination thereof.

7. The organic light emitting diode as claimed in claim 5, wherein the at least one organic thin layer is an electron transport layer or an electron injection layer.

8. The organic light emitting diode as claimed in claim 5, wherein the at least one organic thin layer is an emission layer.

9. The organic light emitting diode as claimed in claim 5, wherein the at least one organic thin layer is an emission layer, and the compound is a phosphorescent host material or a fluorescent host material in the emission layer.

10. The organic light emitting diode as claimed in claim 5, wherein the at least one organic thin layer is an emission layer, and the compound is a fluorescent blue dopant material in the emission layer.

11. A display device comprising the organic light emitting diode as claimed in claim 5.

* * * * *